(12) United States Patent
Yonekura et al.

(10) Patent No.: US 9,417,253 B2
(45) Date of Patent: Aug. 16, 2016

(54) SPECIMEN PROCESSING SYSTEM AND SPECIMEN CONTAINER CLASSIFYING APPARATUS

(75) Inventors: Yasuo Yonekura, Kobe (JP); Yuichiro Ohmae, Kobe (JP); Tokihiro Kosaka, Kakogawa (JP); Takaaki Nagai, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 362 days.

(21) Appl. No.: 12/589,848

(22) Filed: Oct. 28, 2009

(65) Prior Publication Data

US 2010/0111767 A1    May 6, 2010

(30) Foreign Application Priority Data

Oct. 30, 2008  (JP) .................................. 2008-280579
Oct. 30, 2008  (JP) .................................. 2008-280580

(51) Int. Cl.
  *G01N 35/02*   (2006.01)
  *G01N 35/04*   (2006.01)
  *G01N 35/00*   (2006.01)

(52) U.S. Cl.
  CPC ........ *G01N 35/026* (2013.01); *G01N 35/00732* (2013.01)

(58) Field of Classification Search
  CPC .................... G01N 35/00732; G01N 35/026
  See application file for complete search history.

(56) References Cited

U.S. PATENT DOCUMENTS

| | | | |
|---|---|---|---|
| 5,209,903 A | 5/1993 | Kanamori et al. | |
| 5,985,215 A * | 11/1999 | Sakazume et al. | ............. 422/67 |
| 7,314,596 B2 | 1/2008 | Itoh | |
| 2004/0005245 A1 * | 1/2004 | Watson et al. | .................. 422/65 |
| 2008/0071503 A1 * | 3/2008 | Fujita et al. | ................... 702/188 |

FOREIGN PATENT DOCUMENTS

| | | |
|---|---|---|
| JP | 11-304812 | 11/1999 |
| JP | 2000-046835 A | 2/2000 |
| JP | 2002-090374 A | 3/2002 |
| JP | 2003-083991 A | 3/2003 |
| JP | 2003-315348 A | 11/2003 |
| JP | 2005-227206 A | 8/2005 |

* cited by examiner

*Primary Examiner* — P. Kathryn Wright
(74) *Attorney, Agent, or Firm* — Brinks Gilson & Lione

(57) ABSTRACT

A specimen processing system comprising: a specimen measuring section for measuring specimens accommodated in specimen containers; a transport section for transporting specimen containers to the specimen measuring section; a specimen container collect section for collecting specimen containers; an obtainer for obtaining shape information on specimen containers or state information on specimens accommodated in specimen containers; a supply judger configured for determining whether specimen containers are to be supplied to the specimen measuring section on the basis of the result obtained by the obtainer; and a delivery section for delivering specimen containers, which are determined to be supplied to the specimen measuring section by the supply judger, toward the transport section, and delivering specimen containers, which are determined not to be supplied to the specimen measuring section by the supply judger, toward the specimen container collect section, is disclosed. A specimen container classifying apparatus is also disclosed.

9 Claims, 38 Drawing Sheets

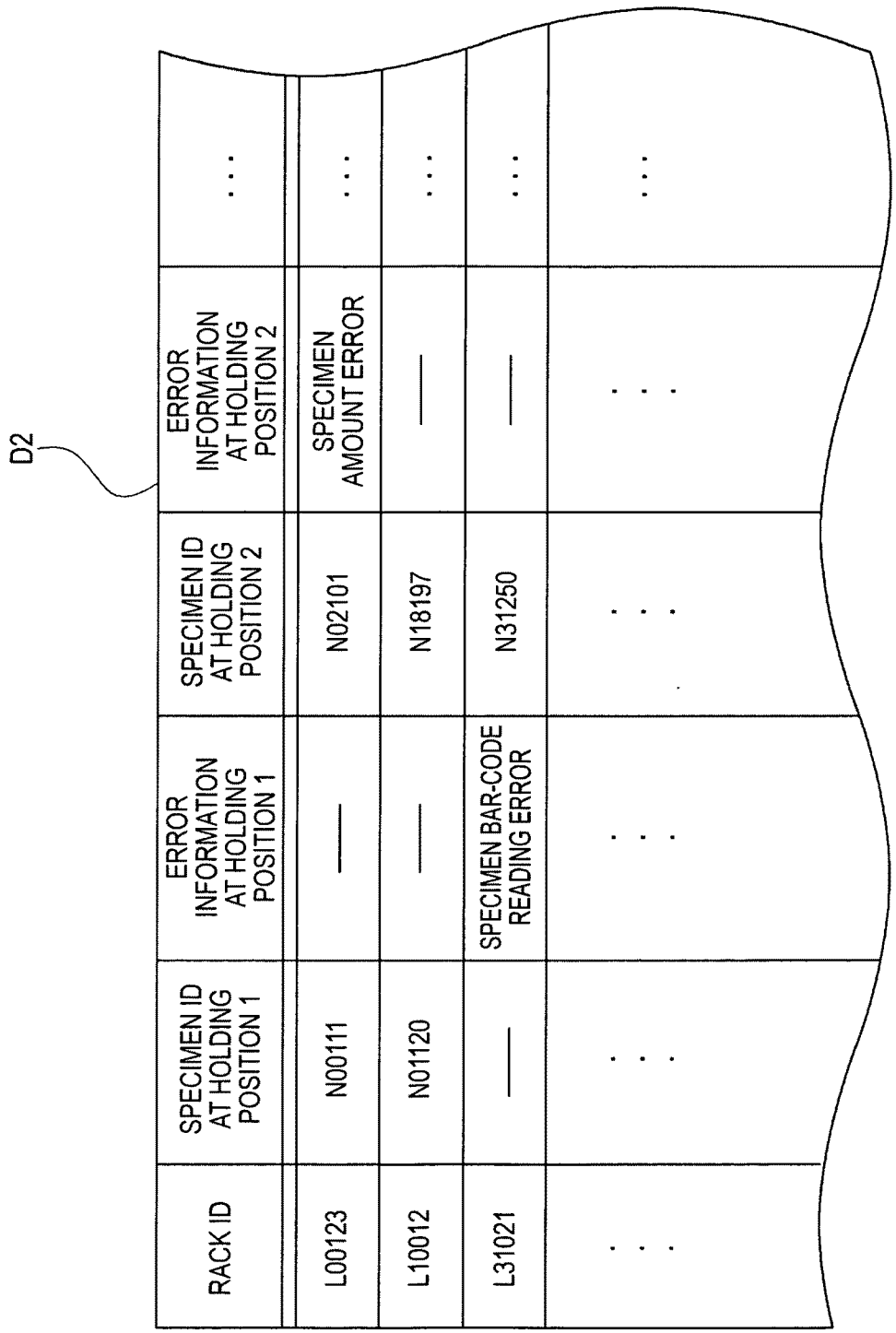

115

SPECIMEN PROCESSING SYSTEM AND SPECIMEN CONTAINER CLASSIFYING APPARATUS

RELATED APPLICATIONS

This application claims priority under 35 U.S.C. §119 to Japanese Patent Application Nos. JP2008-280579 and JP2008-280580 both filed on Oct. 30, 2008, the entire contents of which are hereby incorporated by reference.

FIELD OF THE INVENTION

The present invention relates to a specimen processing system for transporting a specimen to a specimen measuring section for measuring the specimen, and a specimen container classifying apparatus for classifying specimen containers.

BACKGROUND

Conventionally, there are known specimen processing systems, which includes plural specimen processing apparatuses such as a specimen analyzing apparatus and a smear preparing apparatus and a transport apparatus for transporting specimens so as to supply the specimen to the specimen processing apparatuses, where the specimens are transported to the specimen processing apparatuses by the transport apparatus and the transported specimens are processed by the specimen processing apparatuses.

JP-A-11-304812 discloses a specimen processing system which includes a rack supply area for supplying racks which are used for accommodating specimens, a transport line for transporting the racks from the rack supply area, a rack storing section for storing the racks transported on the transport line and plural specimen processing apparatuses arranged along the transport line. The specimen processing system described in JP-A-11-304812 is provided with an identification information reading apparatus for reading identification information adhered to a specimen on a rack before transportation to the plural specimen processing apparatuses, a control section for determining whether the identification information is identified by the identification information reading apparatus, a particular rack recovery area for recovering a rack before transportation to the plural specimen processing apparatuses and a rack moving apparatus for moving a rack which cannot be identified by the determination of the control section to the particular rack collect area.

However, in the analysis processing system described in JP-A-11-304812, even if in a rack there is a specimen container having a shape which is not suitable for the specimen measurement of the system or a specimen container accommodating a specimen which cannot be measured because the amount of the specimen is small or the specimen as blood is coagulated, the rack is supplied to the specimen processing apparatus. When such a specimen container is supplied to the specimen processing apparatus, the operation of the specimen processing apparatus is stopped and a problem thus occurs in that the operation of the entire system stops.

In addition, in the specimen processing system described in JP-A-11-304812, a rack which cannot be identified by the determination of the control section can be collected to the particular rack collect area. However, it is necessary to place the recovered rack in the rack supply area again in order to re-put the collected rack into the specimen processing system. Regarding all the specimens accommodated in the rack placed in the rack supply area in this manner, the identification information thereof is re-read by the identification information reading apparatus. Accordingly, a problem occurs in that the next identification information reading operation cannot be started if the re-reading of the identification information on the rack requiring the re-reading has not been completed, and the reading of the identification information on a rack which can be identified and the conveying of the rack to the transport section are delayed by the reading of the identification information on the rack requiring the re-reading.

SUMMARY OF THE INVENTION

The scope of the present invention is defined solely by the appended claims, and is not affected to any degree by the statements within this summary.

A first aspect of the present invention is a specimen processing system comprising: a specimen measuring section configured for measuring specimens accommodated in specimen containers; a transport section configured for transporting specimen containers to the specimen measuring section; a specimen container collect section configured for collecting specimen containers; an obtainer configured for obtaining shape information on specimen containers or state information on specimens accommodated in specimen containers; a supply judger configured for determining whether specimen containers are to be supplied to the specimen measuring section on the basis of the result obtained by the obtainer; and a delivery section configured for delivering specimen containers, which are determined to be supplied to the specimen measuring section by the supply judger, toward the transport section, and delivering specimen containers, which are determined not to be supplied to the specimen measuring section by the supply judger, toward the specimen container collect section.

A second aspect of the present invention is a specimen processing system comprising: a specimen measuring section configured for measuring specimens accommodated in specimen containers; a transport section configured for transporting specimen containers to the specimen measuring section; a specimen container collect section configured for collecting specimen containers; a delivery section configured for delivering specimen containers toward the transport section and the specimen container collect section; and a controller configured for performing operations, comprising: obtaining shape information on specimen containers or state information on specimens accommodated in specimen containers; determining whether specimen containers are to be supplied to the specimen measuring section on the basis of the obtained result; and controlling the delivery section so as to deliver specimen containers, which are determined to be supplied to the specimen measuring section, toward the transport section, and controlling the delivery section so as to deliver specimen containers, which are determined not to be supplied to the specimen measuring section, toward the specimen container collect section.

A third aspect of the present invention is a specimen container classifying apparatus comprising: a specimen container collect section configured for collecting specimen containers; an obtainer configured for obtaining shape information on specimen containers or state information on specimens accommodated in specimen containers; a supply judger configured for determining whether specimen containers are to be supplied to a specimen measuring section configured to measure specimens on the basis of the result obtained by the obtainer; and a delivery section configured for delivering specimen containers, which are determined to be supplied to the specimen measuring section by the supply judger, toward a transport section for transporting specimen containers to the measuring section, and deliver specimen containers, which are determined not to be supplied to the specimen measuring section by the supply judger, toward the specimen container collect section.

A fourth aspect of the present invention is a specimen processing system comprising: a specimen measuring section configured for measuring specimens accommodated in specimen containers; a specimen setting section configured for setting specimen containers, including a specimen specifying information recording section in which specimen specifying information for specifying a specimen is recorded; a first reader configured for reading the specimen specifying information from the specimen specifying information recording section of the specimen container set in the specimen setting section; a transport section configured for transporting specimen containers to the specimen measuring section; a specimen container collect section configured for collecting specimen containers; a delivery section configured for delivering toward the transport section specimen containers in which an abnormality has not occurred in the reading of specimen specifying information as a result of reading by the first reading section, and deliver toward the specimen collect section specimen containers in which an abnormality has occurred in the reading of specimen specifying information as a result of the reading by the first reading section; and a second reader configured for reading the specimen specifying information from the specimen specifying information recording section of the specimen container collected by the specimen container collect section.

A fifth aspect of the present invention is a specimen container classifying apparatus comprising: a specimen setting section configured for setting specimen containers, including a specimen specifying information recording section in which specimen specifying information for specifying a specimen is recorded; a first reader configured for reading the specimen specifying information from the specimen specifying information recording section of the specimen container set in the specimen setting section; a specimen container collect section configured for collecting specimen containers; a delivery section configured for delivering specimen containers, in which an abnormality has not occurred in the reading of specimen specifying information as a result of reading by the first reader, toward a transport section for transporting specimen containers to a specimen measuring section for measuring specimens, and deliver specimen containers, in which an abnormality has occurred in the reading of specimen specifying information as a result of the reading by the first reader, toward the specimen collect section; and a second reader configured for reading the specimen specifying information from the specimen specifying information recording section of the specimen container collected by the specimen container collect section.

BRIEF DESCRIPTION OF THE DRAWINGS

FIG. 17 is a schematic diagram showing the structure of stored rack information;

DETAILED DESCRIPTION OF THE PREFERRED EMBODIMENTS

The preferred embodiments of the present invention will be described hereinafter with reference to the drawings.

This embodiment is a specimen processing apparatus sorting specimens into the specimens to be provided for the specimen measurement and the specimens which are not to be provided for the specimen measurement.

[Configuration of Specimen Processing System]

Figure 1:
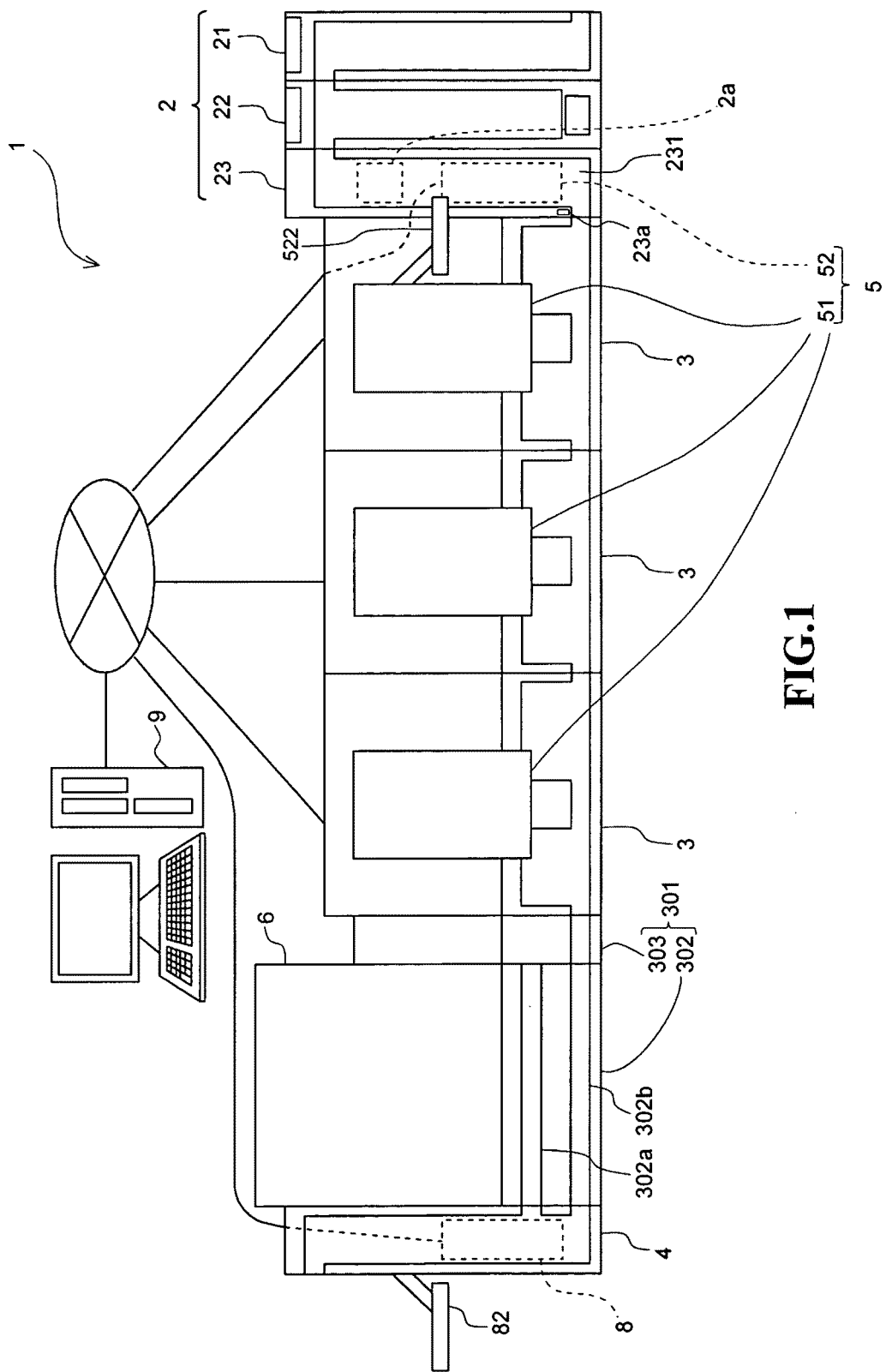
FIG. 1 is a schematic plan view showing the entire configuration of a specimen processing system according to an embodiment.

FIG. 1 is a schematic plan view showing the entire configuration of a specimen processing system according to this embodiment. As shown in FIG. 1, a specimen processing system 1 includes a specimen putting apparatus 2, specimen transport apparatuses 3 and 301, a specimen accommodating apparatus 4, a blood cell analyzing apparatus 5, a smear preparing apparatus 6, and a system control apparatus 8. The specimen processing system 1 according to this embodiment is connected to a host computer 9 via a communication network so as to communicate therewith.

<Configuration of Specimen Putting Apparatus 2>

The specimen putting apparatus 2 includes a specimen setting section 21, a specimen checking unit 22 and a specimen feeding unit 23. The specimen putting apparatus 2 can place plural specimen containers accommodated in a sample rack. In addition, the specimen putting apparatus 2 includes a control section 2a composed of a CPU and a memory and the control section 2a can control the operation mechanisms which are the specimen setting section 21, the specimen checking unit 22 and the specimen feeding unit 23. Moreover, the specimen putting apparatus 2 is connected to the system control apparatus 8 via a communication network so as to perform data communication with the system control apparatus 8.

Figure 2:
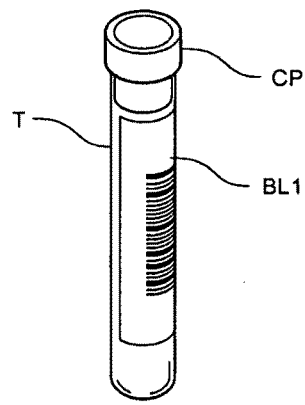
FIG. 2 is a perspective view showing the appearance of a specimen container.
Figure 3:
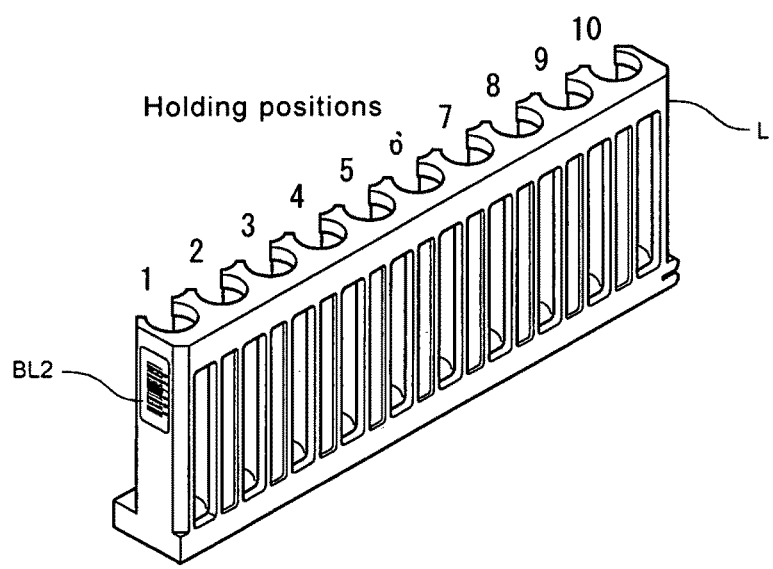
FIG. 3 is a perspective view showing the appearance of a sample rack.

FIG. 2 is a perspective view showing the appearance of a specimen container and FIG. 3 is a perspective view showing the appearance of a sample rack. As shown in FIG. 2, a tube-shaped specimen container T is open at a top end thereof. The specimen container T contains a blood specimen collected from a patient and the opening at the top end is sealed by a cap section CP. The specimen container T is made of translucent glass or synthetic resin and the blood specimen therein can be visually confirmed. A bar-code label BL1 is adhered to a side face of the specimen container T and a bar-code indicating a specimen ID is printed on the bar-code label BL1. A sample rack L can hold ten specimen containers T in parallel. In the sample rack L, the specimen containers T are held in a vertical state (erect state). A bar-code label BL2 is adhered to a side face of the sample rack L and a bar-code indicating a rack ID is printed on the bar-code label BL2.

Figure 4:
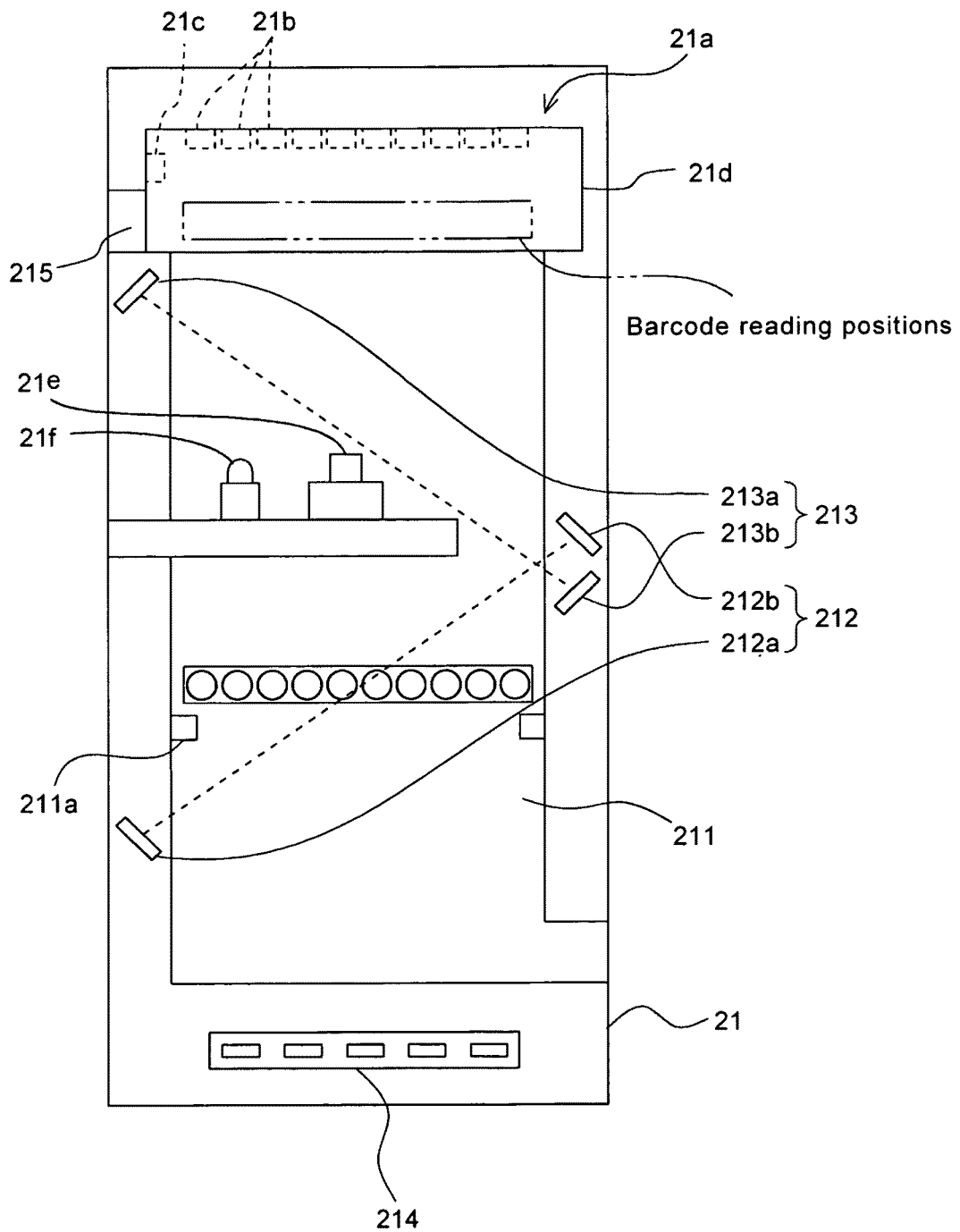
FIG. 4 is a plan view showing the configuration of a specimen setting section.

FIG. 4 is a plan view showing the configuration of the specimen setting section 21. As shown in FIG. 4, the specimen setting section 21 has a concave rack placing section 211 for placing the sample rack L accommodating the specimen containers T. The rack placing section 211 has a rectangular shape and can simultaneously hold the plural sample racks L. The sample racks L are placed in the rack placing section 211 so that the specimen containers T line up in a transverse direction. The rack placing section 211 is provided with sensors 212 and 213 for detecting the sample rack L and an engaging section 211a for moving the sample rack L. The sensors 212 and 213 are optical sensors. The sensor 212 includes a light-emitting section 212a and a light-receiving section 212b, and the sensor 213 includes a light-emitting section 213a and a light-receiving section 213b. The light-emitting section 212a is positioned at the left-front side of the rack placing section 211 and the light-receiving section 212b is positioned at the right-center side of the rack placing section 211. In addition, the light-emitting section 213a is positioned at the left-rear side of the rack placing section 211 and the light-receiving section 213b is positioned at the right-center side of the rack placing section 211. The light-emitting section 212a is disposed so as to emit light diagonally in a backward right direction and the light-receiving section 212b is disposed so as to receive the light over the rack placing section 211. In addition, the light-emitting section 213a is disposed so as to emit light diagonally in a forward right direction and the light-receiving section 213b is disposed so as to receive the light over the rack placing section 211. Accordingly, by the sample rack L being placed in the rack placing section 211, the light emitted from the light-emitting section 212a or 213a is interrupted and thus there is a fall in the light-receiving level of the light-receiving section 212b or 213b. Therefore, the sample rack L is detected by the rack sensor 212 or 213. The sample rack L detected by the rack sensor 212 or 213 is engaged with the engaging section 211a and the engaging section 211a is moved in a front-back direction while being engaged with the sample rack L so as to move the sample rack L on the rack placing section 211.

The specimen setting section 21 includes a bar-code reading section 21a at the inner side of the rack placing section 211. The bar-code reading section 21a includes a specimen bar-code reader 21b for simultaneously reading the specimen bar-codes of the plural specimen containers T accommodated in the sample rack L and a rack bar-code reader 21c for reading the rack bar-code of the sample rack L. Moreover, the bar-code reading section 21a includes a horizontal rotation mechanism 21d for simultaneous horizontal rotation of the plural specimen containers T directly above a bar-code reading position at the most inner side of the rack placing section 211. The sample rack L put into the rack placing section 211 is moved in a direction toward the inner side from the front side, that is, backward on the rack placing section 211, to reach the bar-code reading position. After that, while the specimen container T accommodated in the sample rack L is horizontally rotated by the horizontal rotation mechanism 21$d$, the specimen ID is read from the bar-code label BL1 by the specimen bar-code reader 21$b$. In addition, the rack ID is read from the bar-code label BL2 of the sample rack L by the rack bar-code reader 21$c$. The read rack ID and specimen ID are transmitted to the system control apparatus 8.

When an error occurs in the reading of the specimen bar-code, the control section 2$a$ of the specimen putting apparatus 2 transmits specimen-barcode reading error information corresponding to the holding position of the specimen to the system control apparatus 8. When an error occurs in the reading of the rack bar-code, the control section 2$a$ transmits a rack sequential number sequentially assigned to the put sample rack L to the system control apparatus 8 in place of the rack ID.

A CCD camera 21$e$ for detecting the shape of a specimen container is provided in front of the bar-code reading position of the specimen setting section 21. A white LED 21$f$ is disposed at a predetermined position with respect to the camera 21$e$ and the specimen container T is illuminated by the white LED 21$f$. The white LED 21$f$ emits light toward the sample rack L positioned at the bar-code reading position and is disposed so that the reflected light does not directly enter the camera 21$e$. Accordingly, the reflected light does not directly hit the camera 21$e$ and it is possible to prevent so-called halation occurring due to overexposure.

The CCD camera 21$e$ and the white LED 21$f$ can be vertically moved by a vertical driving mechanism (not shown). When the sample rack L is moved on the rack placing section 211, the CCD camera 21$e$ and the white LED 21$f$ are lifted by the vertical driving mechanism up to a position which does not interfere with the movement of the sample rack L. When the sample rack L is positioned at the bar-code reading position, the CCD camera 21$e$ and the white LED 21$f$ are dropped so as to be positioned in front of the sample rack L and the entire sample rack L is imaged by the CCD camera 21$e$.

Further, the specimen setting section 21 is disposed on the right side of the specimen checking unit 22 (see FIG. 1 for reference). The sample rack L at the bar-code reading position, in which the rack bar-code and the specimen bar-code have been read, is conveyed to the specimen checking unit 22 from a rack delivery port 215 provided on the left side of the bar-code reading position.

As shown in FIG. 4, the specimen setting section 21 is provided with an operating panel 214. A user operates the operating panel 214 so as to issue an analysis start instruction or an analysis completion instruction to the specimen processing system 1.

Figure 5:
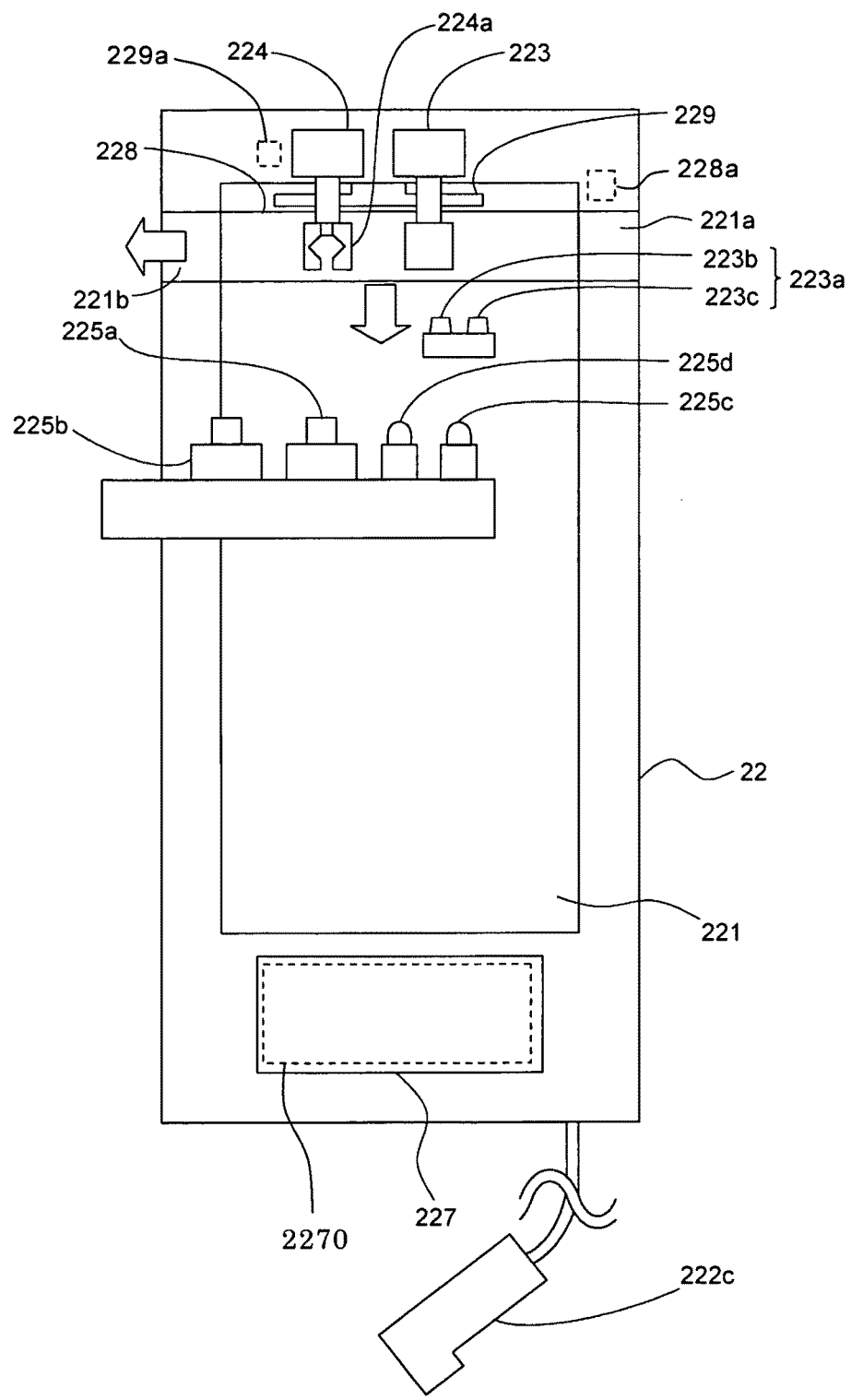
FIG. 5 is a plan view showing the configuration of a specimen checking unit.

FIG. 5 is a plan view showing the configuration of the specimen checking unit 22. As shown in FIG. 5, the specimen checking unit 22 includes a specimen container collect section 221, which has a quadrangular shape when viewed from above, capable of accommodating the plural sample racks L. Further, the specimen checking unit 22 includes a handy bar-code reader 222$c$ which is manually used by a user, a horizontal rotation mechanism 223 for horizontally rotating the specimen container T, an optical sensor 223$a$ for detecting the presence or absence of the bar-code label BL1 of the specimen container T, a specimen container tilting mechanism 224 for taking out the specimen container T from the sample rack L and tilting the specimen container T, two cameras 225$a$ and 225$b$ for imaging the specimen container T and a liquid crystal display section 227. The liquid crystal display section 227 is a touch panel type display and an input device 227$a$ is incorporated therein.

The specimen container collect section 221 is a rectangular recessed portion when viewed from above. A rack feed port 221$a$ for feeding the sample rack L from the specimen setting section 21 is provided in a right wall section at the inner end of the specimen container collect section 221. In addition, a rack delivery port 221$b$ for delivering the sample rack L to the specimen feeding unit 23 is provided in a left wall section at the inner end of the specimen container collect section 221. A transport belt 228 for transporting the sample rack L is provided between the rack feed port 221$a$ and the rack delivery port 221$b$. The transport belt 228 is an annular belt and is driven by a stepping motor 228$a$ so as to transport the sample rack L placed on the transport belt 228 to the left in the drawing. Moreover, a rack feed bar 229 is provided at the further inner side of the transport belt 228. The rack feed bar 229 is driven by a stepping motor 228$a$ so as to push forward the sample rack L on the transport belt 228. The sample rack L delivered to the front by the rack feed bar 229 is retained by the specimen container collect section 221. Thus, the transport belt 228, the stepping motor 228$a$, the rack feed bar 229, and the stepping motor 229$a$ functions as a delivery section which is capable of delivering specimen containers toward the specimen transport apparatus 3 and toward the specimen container collect section 221.

Figure 6:
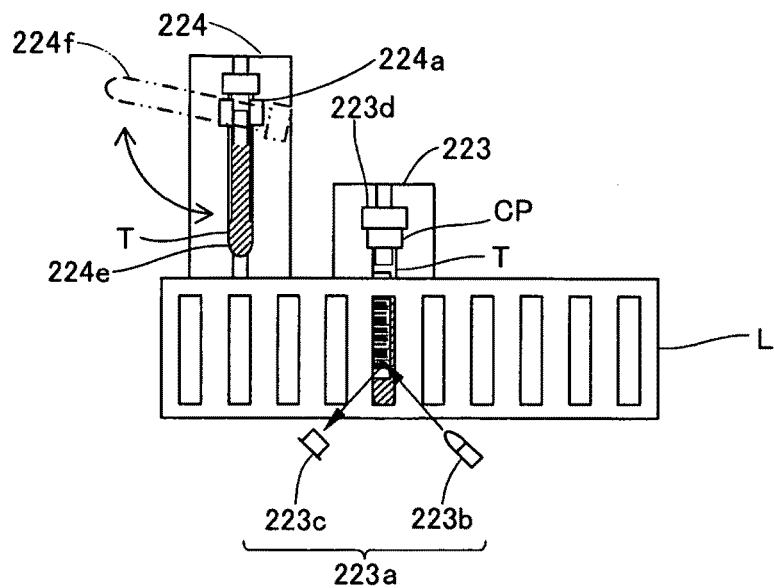
FIG. 6 is a front view schematically showing the configuration of a part of the specimen checking unit.

FIG. 6 is a front view schematically showing the configuration of a part of the specimen checking unit 22. As shown in FIG. 6, the horizontal rotation mechanism 223 has a contacting section 223$d$ which is brought into contact with the top end of the specimen container T on the sample rack L, and the contacting section 223$d$ is configured to be horizontally rotated by a motor. When the contacting section 223$d$ is horizontally rotated while brought into contact with the cap section CP of the specimen container T, the specimen container T is horizontally rotated in the sample rack L. In addition, the optical sensor 223$a$ is disposed in front of the horizontal rotation mechanism 223. The optical sensor 223$a$ is composed of a light-emitting element 223$b$ and a light-receiving element 223$c$. While the specimen container T is horizontally rotated by the horizontal rotation mechanism 223, the specimen container T is irradiated with light from the light-emitting element 223$b$ and the light reflected is received by the light-receiving element 223$c$. When the bar-code label is disposed on the face reflecting the light of the light-emitting element 223$b$, a light-receiving level of the light-receiving element 223$c$ exceeds a predetermined value, and when the bar-code label is not disposed on the face reflecting the light of the light-emitting element 223$b$, the light-receiving level is equal to or less than the predetermined value. The control section 2$a$ checks the light-receiving level of the light-receiving element 223$c$ of the optical sensor 223$a$ while horizontally rotating the specimen container T, and stops the horizontal rotation operation of the horizontal rotation mechanism 223 at a position where the light-receiving level is equal to or less than the predetermined value. Accordingly, an angle of the specimen container T is adjusted so that the face on which the bar-code label BL1 is not disposed faces the front side.

Furthermore, the optical sensor 223$a$ can be vertically moved by a vertical driving mechanism (not shown). The optical sensor 223$a$ is disposed in front of the sample rack L when the sample rack L is on the transport path of the specimen container collect section 221. When the sample rack L is moved to the front side of the specimen container collect section 221, the optical sensor 223a is lifted by the vertical driving mechanism up to a position which does not interfere with the movement of the sample rack L.

Figure 7:
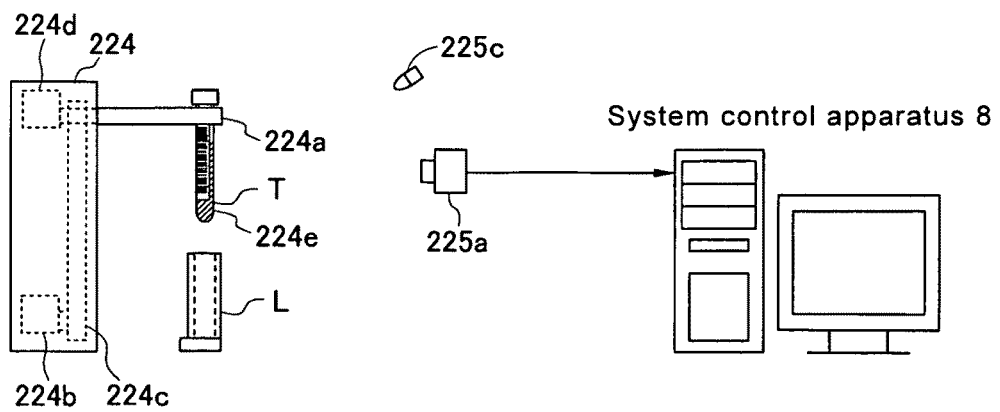
FIG. 7 is a side view showing the schematic configuration of a specimen container tilting mechanism.

On the transport path of the specimen container collect section 221, the sample rack L is intermittently moved to the left in a pitch feeding manner in which the gap between the neighboring specimen containers T is set as one pitch. The above-described specimen container tilting mechanism 224 is provided so as to be positioned on the left side of the horizontal rotation mechanism 223 by a predetermined pitch. FIG. 7 is a side view showing the schematic configuration of the specimen container tilting mechanism 224. The specimen container tilting mechanism 224 includes a grasping section 224a for grasping the vicinity of the top end of the specimen container from both the right and left sides, a motor 224b, and a belt 224c for connecting a rotation shaft of the motor 224b with the grasping section 224a, and the grasping section 224a can be vertically moved by the rotation of the motor 224b. Furthermore, the grasping section 224a is connected to a rotation shaft of a motor 224d and the grasping section 224a can be rotated around a center axis extending in a front-back direction by the rotation of the motor 224d.

The specimen container T, which is rotated by the horizontal rotation mechanism 223 so that the bar-code label BL1 is not disposed on the front face, reaches the position of the specimen container tilting mechanism 224 by moving the sample rack L to the left. Herein, when the grasping section 224a of the specimen container tilting mechanism 224 grasps the vicinity of the top end of the specimen container T and is lifted in such a state, the specimen container T is taken out from the sample rack L. When the specimen container T is completely separated from the sample rack L and reaches a first imaging position 224e, the lifting operation of the grasping section 224a is stopped. The camera 225a is disposed in front of the specimen container T positioned at the first imaging position 224e. A white LED 225c is disposed at a predetermined position with respect to the camera 225a and the specimen container T is illuminated by the white LED 225c.

Figure 8:
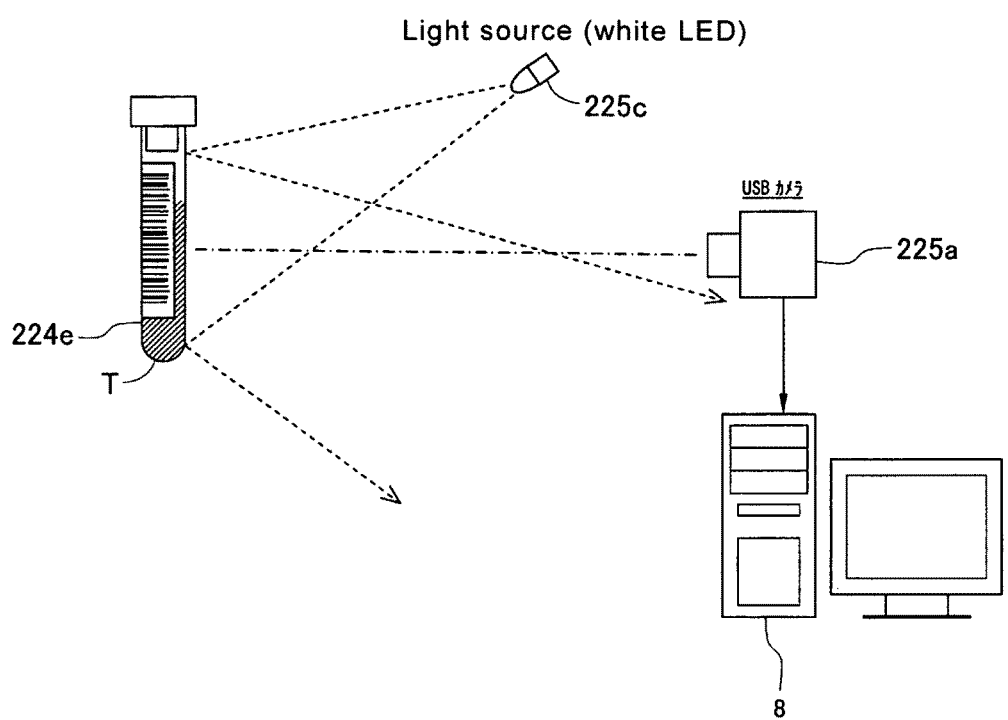
FIG. 8 is a schematic diagram for illustrating a positional relationship between a camera, a white LED and a specimen container in the specimen checking unit according to the embodiment, and a direction of the light emitted from the white LED.

FIG. 8 is a schematic diagram for illustrating a positional relationship between the camera 225a, the white LED 225c and the specimen container T, and a direction of the light emitted from the white LED. As shown in FIG. 8, the white LED 225c is disposed, so that the light is emitted toward the specimen container T positioned at the first imaging position 224e and the light reflected from the specimen container T does not directly enter the camera 225a positioned in front of the specimen container T. Accordingly, the camera 225a is not directly exposed to the reflected light and so-called halation due to overexposure can be prevented.

The specimen container T grasped at the first imaging position 224e by the grasping section 224a is imaged by the camera 225a while being in an erect state (vertical state), and the image data obtained in this manner is transmitted to the system control apparatus 8. After that, the grasping section 224a is vertically rotated by the motor 224d to tilt the specimen container T. As shown by the two-dot chain line in FIG. 6, the grasping section 224a is turned by a predetermined angle so that a bottom portion of the specimen container T reaches a second imaging position 224f positioned higher than the cap section CP. The camera 225b (see FIG. 5 for reference) is disposed in front of the specimen container T positioned at the second imaging position 224f. A white LED 225d (see FIG. 5 for reference) is disposed at a predetermined position with respect to the camera 225b and the specimen container T is illuminated by the white LED 225d. A relative positional relationship between the white LED 225d and the camera 225b is the same as a relative positional relationship between the white LED 225c and the camera 225a. That is, the white LED 225d is disposed, so that the light is emitted toward the specimen container T positioned at the second imaging position 224f, and the light reflected from the specimen container T does not directly enter the camera 225b positioned in front of the specimen container T.

The specimen container T grasped at the second imaging position 224f by the grasping section 224a is imaged by the camera 225a while being tilted as described above, and the image data obtained in this manner is transmitted to the system control apparatus 8. The sample rack L in which all the specimen containers T have been imaged is delivered from the rack delivery port 221b by the transport belt 228.

The bar-code reader 222c is provided with a light-emitting section and a light-receiving section (line sensor) (not shown), and is connected to the main body of the specimen checking unit 22 by a flexible cable for transmitting an electric signal. The bar-code reader 222c is operated when a user manually re-reads a bar-code which cannot be read by the bar-code reading section 21a.

The specimen feeding unit 23 disposed on the left side of the specimen checking unit 22 includes a rack re-putting section 231 in which the plural sample racks L are placed (see FIG. 1 for reference). The rack re-putting section 231 has the same rectangular parallelepiped shape as the rack placing section 211 of the specimen setting section 21, when viewed from above. There is no right wall section at the inner side of the rack re-putting section 231 and this forms a rack feed port. Through the rack feed port, the sample rack L is fed to the specimen feeding unit 23 from the specimen checking unit 22. In addition, there is also no left wall section at the front side (front-face side) of the rack re-putting section 231 of the specimen feeding unit 23 and this serves as a rack delivery port. The sample rack L fed from the rack feed port is moved to the front by the rack re-putting section 231 so as to reach the most forward position and is then delivered to the left from the rack delivery port. Moreover, the specimen feeding unit 23 is provided with a bar-code reader 23a for reading a rack bar-code. By using the bar-code reader, the rack ID of the sample rack L transported to the rack re-putting section 231 is read, and before the sample rack L is transported to the following specimen transport apparatus 3, convey request data including the rack ID is transmitted to the system control apparatus 8.

<Configuration of Specimen Transport Apparatus 3>

Next, the configuration of the specimen transport apparatus 3 will be described. As shown in FIG. 1, the specimen processing system 1 includes 3 specimen transport apparatuses 3. The specimen transport apparatuses 3, 3 and 3 are each disposed in front of three measuring units 51, 51 and 51 of the blood cell analyzing apparatuses 5. Neighboring specimen transport apparatuses 3 and 3 are connected to each other so as to send and receive a sample rack L between each other. The rightmost specimen transport apparatus 3 is connected to the above-described specimen putting apparatus 2 so as to introduce the sample rack L conveyed from the specimen putting apparatus 2 thereto. The leftmost specimen transport apparatus 3 is connected to the specimen transport apparatus 301 to convey the sample rack L to the specimen transport apparatus 301.

Figure 9:
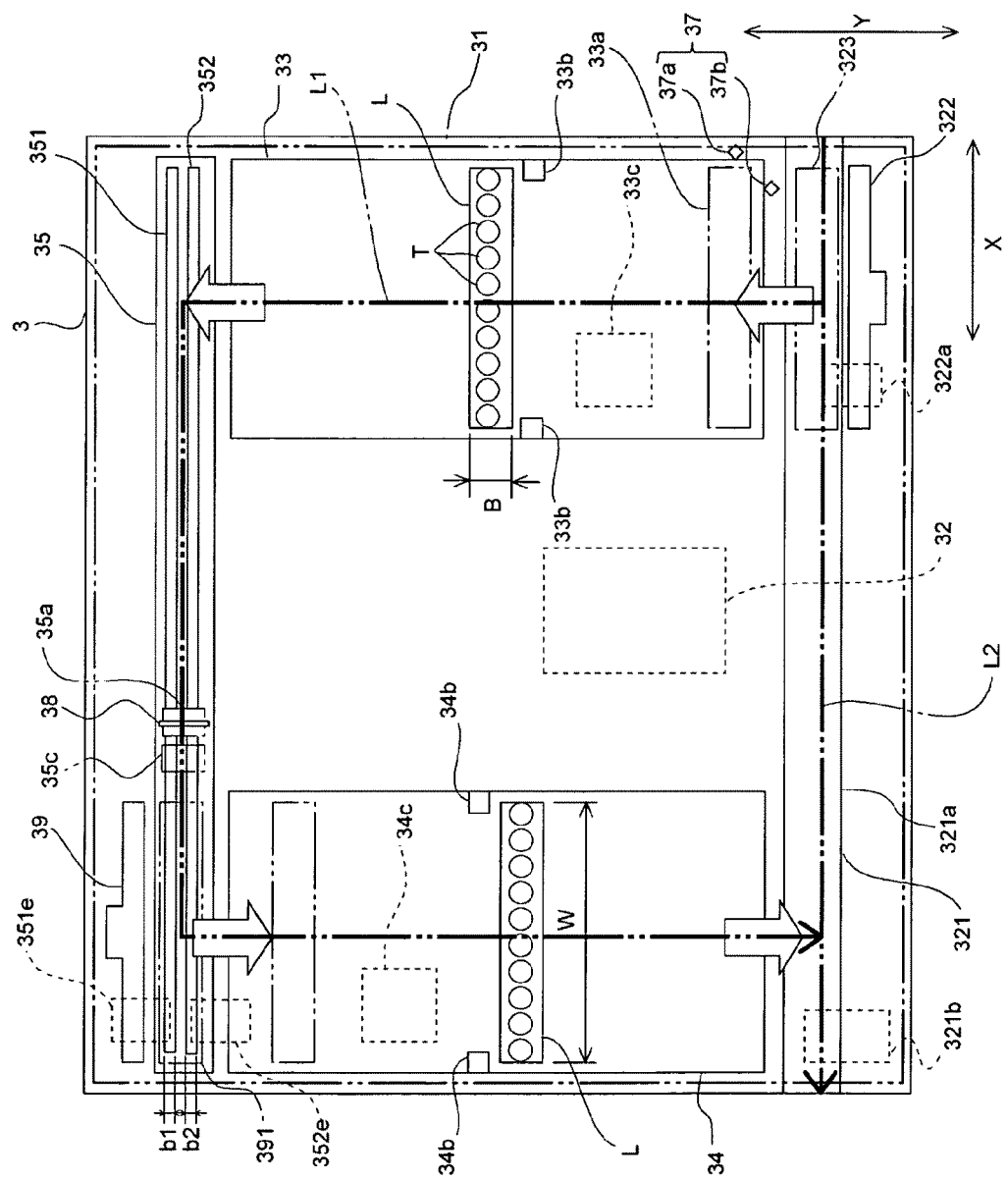
FIG. 9 is a plan view showing the configuration of a specimen transport apparatus.

FIG. 9 is a plan view showing the configuration of the specimen transport apparatus 3. As shown in FIG. 9, the specimen transport apparatus 3 includes a transport mechanism 31 for transporting a specimen and a control section 32 for controlling the transport mechanism 31. The transport mechanism 31 includes a before-analysis rack holding section 33 capable of temporarily holding the plural sample racks L holding the specimen containers T accommodating the specimens before the analysis is performed, an after-analysis rack holding section 34 capable of temporarily holding the plural sample racks L holding the specimen containers T in which the specimen is aspirated by the measuring unit 51, a rack transport section 35 for horizontally moving the sample rack L in a straight line in a direction of the arrow X in the drawing so as to supply the specimen to the measuring unit 51 and transporting the sample rack L received from the before-analysis rack holding section 33 to the after-analysis rack holding section 34, and a rack transport section 321 for conveying the sample rack L from the apparatus (specimen putting apparatus 2 or specimen transport apparatus 3) on the upstream side of the transport and conveying the sample rack L to the apparatus (specimen transport apparatus 3 or 301) on the downstream side of the transport without supplying the specimen accommodated in the sample rack L to the measuring unit 51.

The before-analysis rack holding section 33 has a quadrangular shape when viewed from above, and its width is slightly larger than the width of the sample rack L. The before-analysis rack holding section 33 is formed to be lower by one stage than the surrounding surface, and on an upper face thereof, the sample racks L before analysis are placed. The before-analysis rack holding section 33 is connected to the rack transport section 321, and the sample rack L is sent from the rack transport section 321 by a rack delivery section 322 to be described later. A rack sensor 37 is installed near the before-analysis rack holding section 33, and a rack detection position 33a at which the sample rack L is detected by the rack sensor 37 is provided on the before-analysis rack holding section 33. The rack sensor 37 is an optical sensor and includes a light-emitting section 37a and a light-receiving section 37b. The light-emitting section 37a is provided adjacent to the rack detection position 33a and the light-receiving section 37b is provided in front of the rack detection position 33a. The light-emitting section 37a is disposed so as to emit light diagonally in a forward direction and the light-receiving section 37b is disposed so as to receive the light. Accordingly, the sample rack L sent from the rack transport section 321 is positioned at the rack detection position 33a and the light emitted from the light-emitting section 37a is thus blocked by the sample rack L. Therefore, there is a fall in the light-receiving level of the light-receiving section 37b and the sample rack L is thus detected by the rack sensor 37. Further, rack sending sections 33b are provided in both faces of the before-analysis rack holding section 33 so as to be protruded inward. When the sample rack L is detected by the rack sensor 37, the rack sending sections 33b protrude so as to be engaged with the sample rack L. In this state, the rack sending sections 33b are moved backward (moved in a direction to be close to the rack transport section 35) and thus the sample rack L is moved backward. The rack sending sections 33b are configured to be driven by a stepping motor 33c provided below the before-analysis rack holding section 33.

As shown in FIG. 9, the rack transport section 35 can move the sample rack L, which is moved by the before-analysis rack holding section 33, in the X direction. On the path of the transport of the sample rack L by the rack transport section 35, there are a specimen container detection position 35a where the specimen container is detected by a specimen container sensor 38 and a specimen supply position 35c for supplying the specimen to the measuring unit 51 of the blood cell analyzing apparatus 5. The rack transport section 35 is configured to transport the sample rack L via the specimen container detection position 35a so that the specimen is transported to the specimen supply position 35c. The specimen supply position 35c is positioned on the downstream side in the transport direction so as to be separated from the specimen container detection position 35a by the distance corresponding to one specimen. When the specimen is transported to the specimen supply position 35c by the rack transport section 35, a band section of the measuring unit 51 of the blood cell analyzing apparatus 5 to be described later grasps the specimen container T for the specimen and takes out the specimen container T from the sample rack L so as to aspirate the specimen from the specimen container T, and thus the specimen is supplied to the measuring unit 51. After transporting the specimen container to the specimen supply position 35c, the rack transport section 35 stands by to transport the sample rack L while the supply of the specimen is completed and the specimen container T is returned to the sample rack L.

Figure 10:
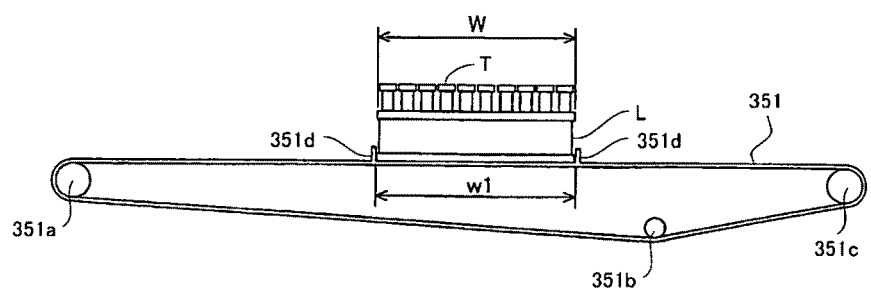
FIG. 10 is a front view showing the configuration of a first belt of the specimen transport apparatus.
Figure 11:
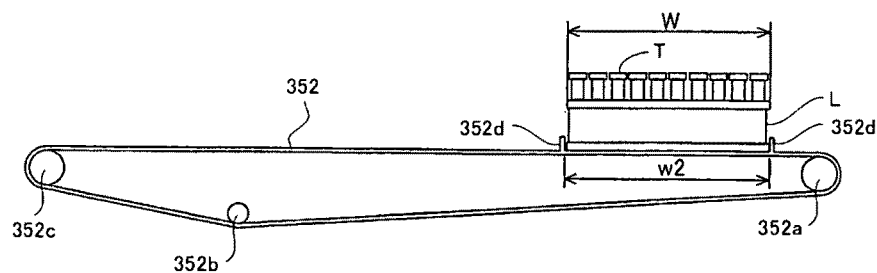
FIG. 11 is a front view showing the configuration of a second belt of the specimen transport apparatus.

In addition, the rack transport section 35 has two independently operable belts, that is, a first belt 351 and a second belt 352. Widths b1 and b2 in a direction of the arrow Y of the first belt 351 and the second belt 352 are equal to or smaller than half of a width B in the direction of the arrow Y of the sample rack L. The first belt 351 and the second belt 352 are disposed in parallel so as not to protrude from the width B of the sample rack L when the rack transport section 35 transports the sample rack L. FIG. 10 is a front view showing the configuration of the first belt 351 and FIG. 11 is a front view showing the configuration of the second belt 352. As shown in FIGS. 10 and 11, the first belt 351 and the second belt 352 are annularly formed. The first belt 351 is disposed so as to surround rollers 351a to 351c and the second belt 352 is disposed so as to surround rollers 352a to 352c. In a peripheral section of the first belt 351, two protrusions 351d are provided so as to have an inner width w1 slightly larger (for example, 1 mm) than a width W in the X direction of the sample rack L, and similarly, in a peripheral section of the second belt 352, two protrusions 352d are provided so as to have the same inner width w2 as the inner width w1. The first belt 351 is configured so that the sample rack L held inside of the two protrusions 351d is moved in the direction of the arrow X by being moved along the peripheries of the rollers 351a to 351c by a stepping motor 351e (see FIG. 9 for reference). The second belt 352 is configured so that the sample rack L held inside of the two protrusions 352d is moved in the direction of the arrow X by being moved along the peripheries of the rollers 352a to 352c by a stepping motor 352e (see FIG. 9 for reference). In addition, the first belt 351 and the second belt 352 are configured so as to move the sample rack L independently of each other.

The specimen container sensor 38 is a contact sensor and has a curtain-like contact piece, a light-emitting element emitting light and a light-receiving element (not shown). The specimen container sensor is configured so that the contact piece is bent when brought into contact with a substance to be detected which is a detection object and the light emitted from the light-emitting element is thus reflected by the contact piece and enters the light-receiving element. Accordingly, while the specimen container T as a detection object accommodated in the sample rack L passes under the specimen container sensor 38, the contact piece is bent by the specimen container T and the specimen container T can be detected.

A rack delivery section 39 is disposed so as to be opposed to the after-analysis rack holding section 34 to be described later with the rack transport section 35 interposed therebetween. The rack delivery section 39 is configured to be horizontally moved in a straight line in the direction of the arrow Y by a driving force of a stepping motor 39a. Accordingly, when the sample rack L is transported to a position 391

(hereinafter, referred to as "after-analysis rack delivery position") between the after-analysis rack holding section 34 and the rack delivery section 39, by moving the rack delivery section 39 toward the after-analysis rack holding section 34, the sample rack L is pushed so as to be moved to the inside of the after-analysis rack holding section 34. In this manner, the sample rack L in which the analysis is completed is delivered to the after-analysis rack holding section 34 from the rack transport section 35.

The rack transport section 321 extends in the direction of the arrow X in the drawing and can horizontally move the sample rack L in a straight line in the direction of the arrow X. The rack transport section 321 has an annular belt 321a and a stepping motor 321b and is configured so as to rotate the belt 321a in the direction of the arrow X by a driving force of the stepping motor 321b. Accordingly, the sample rack L placed on the belt 321a can be moved in the X direction. In addition, the rack delivery section 322 is disposed in front of the before-analysis rack holding section 33 so as to be opposed to the before-analysis rack holding section 33 with the rack transport section 321 interposed therebetween. The rack delivery section 322 is configured to be horizontally moved in a straight line in the direction of the arrow Y by a driving force of a stepping motor 322a. Accordingly, when the sample rack L is transported to a position 323 (hereinafter, referred to as "before-analysis rack delivery position") between the before-analysis rack holding section 33 and the rack delivery section 322, by moving the rack delivery section 322 toward the before-analysis rack holding section 33, the sample rack L is pushed so as to be moved to the rack detection position 33a in the before-analysis rack holding section 33.

The after-analysis rack holding section 34 has a quadrangular shape when viewed from above, and its width is slightly larger than the width of the sample rack L. The after-analysis rack holding section 34 is formed to be lower by one stage than the surrounding surface, and on an upper face thereof, the sample racks L in which the analysis is completed are placed. The after-analysis rack holding section 34 is connected to the rack transport section 35, and as described above, the sample rack L is sent from the rack transport section 35 by the rack delivery section 39. Rack sending sections 34b are provided in both faces of the after-analysis rack holding section 34 so as to protrude inward. When the sample rack L is conveyed by the rack delivery section 39, the rack sending sections 34b protrude so as to be engaged with the sample rack L. In this state, the rack sending sections are moved forward (moved in a direction to be close to the rack transport section 321) and thus the sample rack L is moved forward. The rack sending sections 34b are configured to be driven by a stepping motor 34c provided below the after-analysis rack holding section 34.

Due to such a configuration, a measuring line L1, which is used as a transport line for the sample rack L passing through the specimen supply position 35c, and a skip line L2, which is used as a transport line for conveying the sample rack L not passing through the specimen supply position 35c to the apparatus on the downstream side, are formed in the transport mechanism 31.

The transport mechanism 31 having the above-described configuration is controlled by the control section 32. The control section 32 is composed of a CPU, a ROM, a RAM and the like (not shown) and a control program of the transport mechanism 31, which is stored in the ROM, can be executed by the CPU. The control section 32 includes an Ethernet (registered trade name) interface and is connected to an information processing unit 52 and the system control apparatus 8 via a LAN so as to communicate therewith.

Due to the above-described configuration, the specimen transport apparatus 3 transports the sample rack L, which is transported from the specimen putting apparatus 2, to the before-analysis rack delivery position 323 by using the rack transport section 321, moves the sample rack to the before-analysis rack holding section 33 by using the rack delivery section 322, delivers the sample rack L to the rack transport section 35 from the before-analysis rack holding section 33, and also transports the sample rack by using the rack transport section 35, and thus the specimen can be supplied to the measuring unit 51 of the blood cell analyzing apparatus 5. The sample rack L, which accommodates the specimens for which the aspiration have been completed, is moved to the after-analysis rack delivery position 391 by the rack transport section 35 and is delivered to the after-analysis rack holding section 34 by the rack delivery section 39. The sample rack L held in the after-analysis rack holding section 34 is moved to the rack transport section 321 and is conveyed to the following apparatus (specimen transport apparatus 3 or 301) by the rack transport section 321. When the sample rack L, which accommodates the specimens to be processed by the measuring unit 51 or the smear preparing apparatus 6 on the downstream side of the transport or the specimens in which the analysis is completed, is received by the specimen transport apparatus 3 from the preceding apparatus, the sample rack L is transported in the direction of the arrow X by the rack transport section 321 and is conveyed to the following specimen transport apparatus 3.

<Configuration of Specimen Transport Apparatus 301>

As shown in FIG. 1, the specimen transport apparatus 301 is disposed in front of the smear preparing apparatus 6. The right end of the specimen transport apparatus 301 is connected to the specimen transport apparatus 3 positioned on the downmost-stream side of the transport (left side in the drawing) among the three specimen transport apparatuses 3, 3 and 3. The left end of the specimen transport apparatus 301 is connected to the specimen accommodating apparatus 4.

The specimen transport apparatus 301 includes a conveyor 302 and a rack slider 303. The conveyor 302 is provided with two rack transport paths 302a and 302b extending in a horizontal direction. The rack transport path 302a which is close to the smear preparing apparatus 6 is a measuring line for transporting the sample rack L accommodating the specimen to be supplied to the smear preparing apparatus 6. The rack transport path 302b which is separated from the smear preparing apparatus 6 is a skip line for transporting the sample rack L not accommodating the specimen to be supplied to the smear preparing apparatus 6. The conveyor 302 includes a CPU, a memory and a control section (not shown) for controlling the operating mechanisms.

The rack slider 303 is disposed on the right side of the conveyor 302, and sorts and puts the sample racks L to the measuring line 302a and the skip line 302b of the conveyor 302.

<Configuration of Specimen Accommodating Apparatus 4>

The specimen accommodating apparatus 4 is configured so as to place the plural sample racks L. The specimen accommodating apparatus 4 receives from the specimen transport apparatus 301 the sample rack L in which the analysis or the smear preparation is completed, and accommodates the sample rack L.

<Configuration of Blood Cell Analyzing Apparatus 5>

The blood cell analyzing apparatus 5, which is used as an optical flow cytometry type multiple blood cell analyzing apparatus, obtains the fluorescent intensity, the side-scattered light intensity and the like of blood cells included in a blood specimen, classifies the blood cells included in the specimen on the basis of the above intensities, and counts the number of blood cells for each type. Moreover, the blood cell analyzing apparatus 5 creates a scattergram in which the classified blood cells are color-coded for each type, and displays the scattergram. The blood cell analyzing apparatus 5 includes a measuring unit 51 for measuring a blood specimen and an information processing unit 52 for processing measuring data output from the measuring unit 51 and displaying an analysis result of the blood specimen.

As shown in FIG. 1, the blood cell analyzing apparatus 5 includes the three measuring units 51, 51 and 51 and one information processing unit 52. The information processing unit 52 is connected to the three measuring units 51, 51 and 51 so as to communicate therewith and can control the operations of the three measuring units 51, 51 and 51. The information processing unit 52 is also connected to the three specimen transport apparatuses 3, 3 and 3, which are respectively disposed in front of the three measuring units 51, 51 and 51, so as to communicate therewith.

Figure 12:
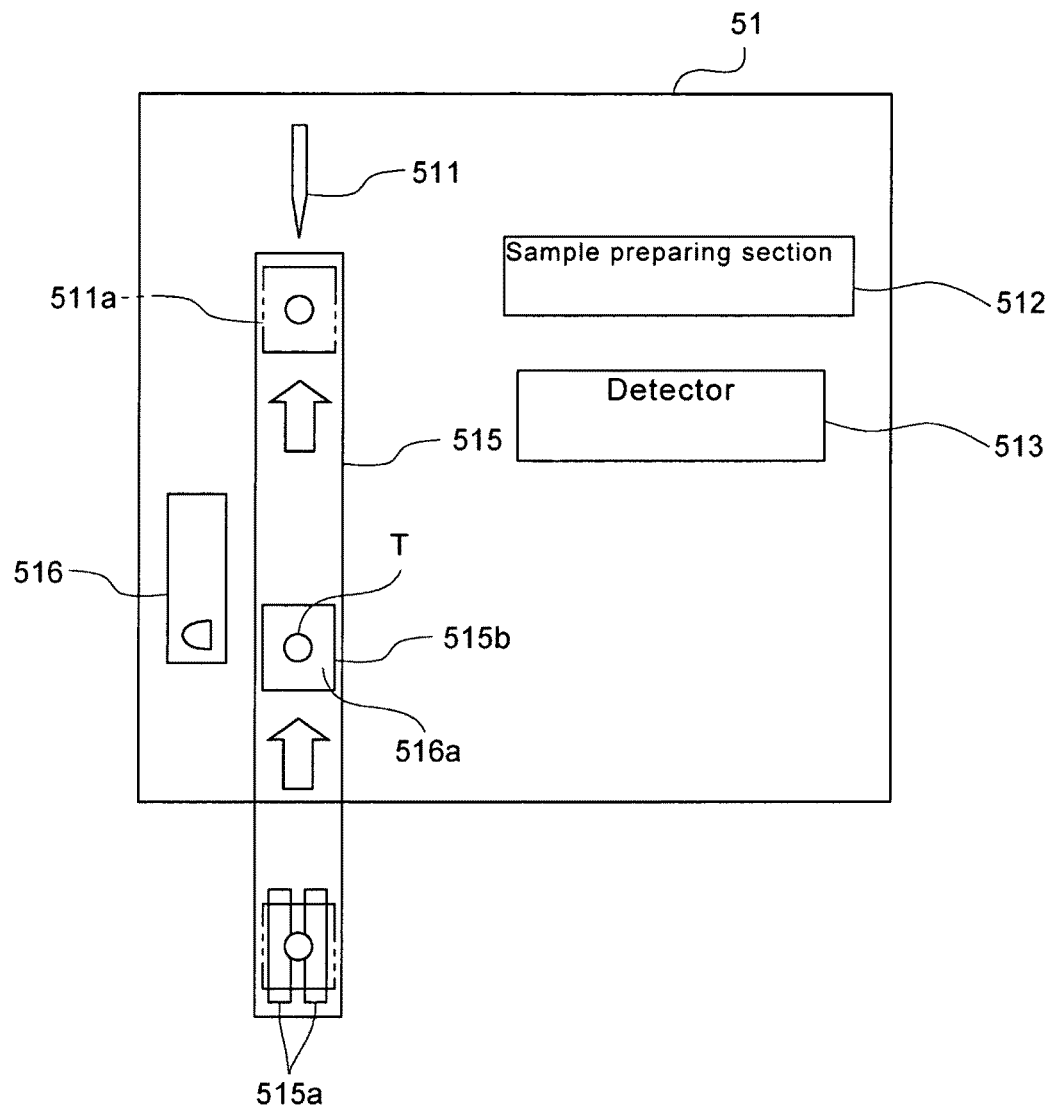
FIG. 12 is a block diagram showing the configuration of a measuring unit of a specimen analyzing apparatus.

The three measuring units 51, 51 and 51 have the same configuration. FIG. 12 is a block diagram showing the configuration of the measuring unit 51. As shown in FIG. 12, the measuring unit 51 includes a specimen aspirating section 511 for aspirating blood as a specimen from the specimen container (blood collection tube) T, a sample preparing section 512 for preparing a measurement sample which is used in the measurement from the blood aspirated by the specimen aspirating section 511 and a detecting section 513 for detecting a blood cell from the measurement sample prepared by the sample preparing section 512. Moreover, the measuring unit 51 further has a taking port (not shown) for taking the specimen container T accommodated in the sample rack L transported by the rack transport section 35 of the specimen transport apparatus 3 into the measuring unit 51, and a specimen container transport section 515 for taking the specimen container T from the sample rack L into the measuring unit 51 and transporting the specimen container T to an aspiration position where the aspiration is performed by the specimen aspirating section 511.

An aspiration tube (not shown) is provided at the tip end of the specimen aspirating section 511. The specimen aspirating section 511 can be vertically moved and is configured to be moved downward so that the aspiration tube penetrates into the cap section CP of the specimen container T transported to the aspiration position so as to aspirate the blood in the specimen container.

The sample preparing section 512 includes plural reaction chambers (not shown). Further, the sample preparing section 512 is connected to a reagent container (not shown) and can supply reagents such as a smearing reagent, a hemolytic agent and a diluent to the reaction chamber. The sample preparing section 512 is also connected to an aspiration tube of the specimen aspirating section 511 and can supply the blood specimen aspirated by the aspiration tube to the reaction chamber. The sample preparing section 512 mixes and stirs the specimen and the reagent in the reaction chamber to prepare a sample (measurement sample) for the measurement by the detecting section 513.

The detecting section 513 can detect red blood cells (RBC) and platelets (PLT) by a sheath flow DC detection method. In detecting RBCs and PLTs by the sheath flow DC detection method, a measurement sample is measured in which a specimen and a diluent are mixed, and measuring data obtained in this manner is analyzed by the information processing unit 52 so as to measure the RBCs and PLTs. In addition, the detecting section 513 is configured to detect hemoglobin (HGB) by a SLS-hemoglobin method and detect white blood cells (WBC), neutrophils (NEUT), lymphocytes (LYMPH), eosinophils (EO), basophil (BASO) and monocytes (MONO) by a flow cytometry method using semiconductor lasers. In the detecting section 513, the detection of WBCs unaccompanied by 5 classifications of white blood cells, that is, the detection of WBCs unaccompanied by the detection of NEUTs, LYMPHs, EOs, BASOs and MONOs is different in detection method from the detection of WBCs accompanied by 5 classifications of white blood cells. In the detection of WBCs unaccompanied by 5 classifications of white blood cells, a measurement sample is measured in which a specimen, a hemolytic agent and a diluent are mixed, and measuring data obtained in this manner is analyzed by the information processing unit 52 so as to measure WBCs. In the detection of WBCs accompanied by 5 classifications of white blood cells, a measurement sample is measured in which a smearing reagent, a hemolytic agent and a diluent are mixed, and measuring data obtained in this manner is analyzed by the information processing unit 52 so as to measure NEUTs, LYMPHs, EOs, BASOs, MONOs and WBCs.

The specimen container transport section 515 includes a hand section 515a capable of grasping the specimen container T. The hand section 515a includes a pair of grasping members opposed to each other and can allow the grasping members to be close to each other or separated from each other. The specimen container T can be held by allowing the grasping members with the specimen container T interposed therebetween to be close to each other. Further, the specimen container transport section 515 can move the hand section 515a in a vertical direction and in a front-back direction (Y direction) and can oscillate the hand section 515a. Accordingly, by holding the specimen container T accommodated in the sample rack L and positioned at the supply position 35c with the hand section 515a and moving the hand section 515a upward, the specimen container T is pulled out of the sample rack L, and by oscillating the hand section 515a, the specimen in the specimen container T can be stirred.

In addition, the specimen container transport section 515 includes a specimen container setting section 515b having a hole to which the specimen container T can be inserted. The specimen container T grasped by the above-described hand section 515a is moved after the completion of stirring and the grasped specimen container T is inserted to the hole of the specimen container setting section 515b. Then, by allowing the grasping members to be separated from each other, the specimen container T is released from the hand section 515a and the specimen container T is set in the specimen container setting section 515b. The specimen container setting section 515b can be horizontally moved in the Y direction by the power of a stepping motor (not shown). A bar-code reading section 516 is provided in the measuring unit 51. The specimen container setting section 515b can be moved to a bar-code reading position 516a near the bar-code reading section 516 and an aspiration position 511a where the aspiration is performed by the specimen aspirating section 511. When the specimen container setting section 515b is moved to the bar-code reading position 516a, the set specimen container T is horizontally rotated by a rotation mechanism (not shown) and the specimen bar-code is read by the bar-code reading section 516. Accordingly, even when the bar-code label BL1 of the specimen container T is positioned on the opposite side with respect to the bar-code reading section 516, the bar-code label BL1 can face the bar-code reading section 516 by rotating the specimen container T and the bar-code reading section 516 can read the specimen bar-code. When the specimen container setting section 515b is moved to the aspiration position, the specimen is aspirated from the set specimen container T by the specimen aspirating section 511.

Figure 13:
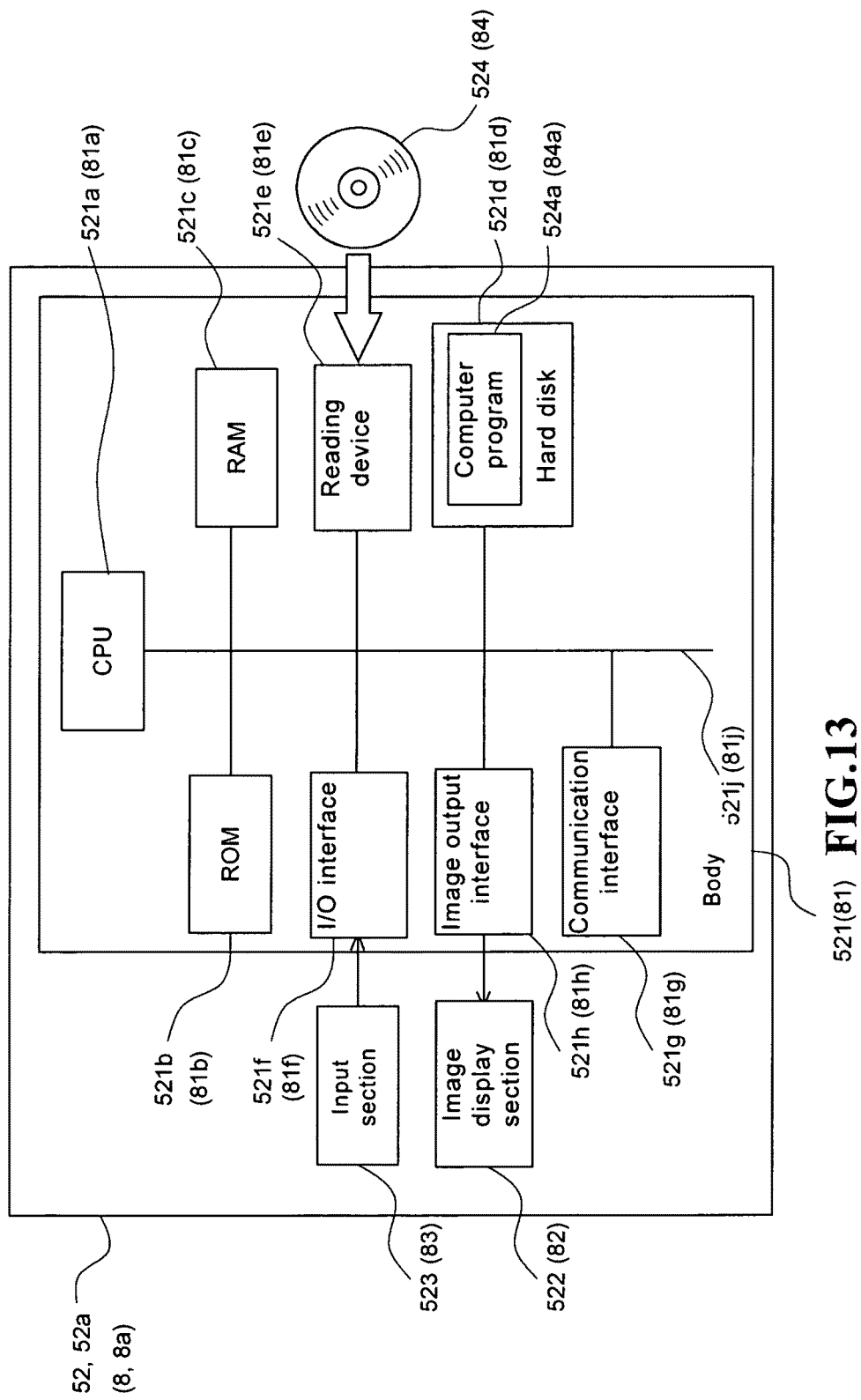
FIG. 13 is a block diagram showing the configuration of an information processing unit of the specimen analyzing apparatus.

Next, the configuration of the information processing unit 52 will be described. The information processing unit 52 is composed of a computer. FIG. 13 is a block diagram showing the configuration of the information processing unit 52. The information processing unit 52 is realized by a computer 52a. As shown in FIG. 13, the computer 52a includes a main body 521, an image display section 522 and an input section 523. The main body 521 includes a CPU 521a, a ROM 521b, a RAM 521c, a hard disk 521d, a reading device 521e, an I/O interface 521f, a communication interface 521g and an image output interface 521h. The CPU 521a, ROM 521b, RAM 521c, hard disk 521d, reading device 521e, I/O interface 521f, communication interface 521g and image output interface 521h are connected to each other by a bus 521j.

The CPU 521a can execute a computer program loaded to the RAM 521c. The CPU 521a executes a computer program 524a for analyzing a specimen and controlling the measuring unit 51, which will be described later, so that the computer 52a functions as the information processing unit 52.

The ROM 521b is composed of a mask ROM, a PROM, an EPROM, an EEPROM or the like and the computer program which is executed by the CPU 521a and data which is used for the computer program are recorded in the ROM.

The RAM 521c is composed of a SRAM, a DRAM or the like. The RAM 521c is used to read the computer program 524a recorded in the hard disk 521d. Moreover, the RAM is used as an operating area of the CPU 521a when the CPU 521a executes a computer program.

In the hard disk 521d, various computer programs for being executed by the CPU 521a, such as an operating system and an application program, and data which are used to execute the computer programs are installed. The computer program 524a to be described later is also installed in the hard disk 521d.

The reading device 521e is composed of a flexible disk drive, a CD-ROM drive, a DVD-ROM drive or the like and can read the computer program or data recorded in a portable recording medium 524. In the portable recording medium 524, the computer program 524a for prompting the computer to function as the information processing unit 52 is stored. The computer 52a can read the computer program 524a from the portable recording medium 524 and install the computer program 524a in the hard disk 521d.

The computer program 524a is provided by the portable recording medium 524 and can be also provided from an external device, which is connected to the computer 52a by an electric communication line (which may be wired or wireless) so as to communicate therewith, through the electric communication line. For example, the computer program 524a is stored in a hard disk of a server computer on the internet and the computer 52a accesses the server computer so as to download the computer program and install the computer program in the hard disk 521d.

Furthermore, in the hard disk 521d, for example, a multitasking operating system such as Windows (registered trade name), which is made and distributed by Microsoft corporation in America, is installed. In the following description, the computer program 524a according to this embodiment operates on the above operating system.

The I/O interface 521f is composed of, for example, a serial interface such as USB, IEEE1394 or RS-232C, a parallel interface such as SCSI, IDE or IEEE 1284, and an analog interface including a D/A converter and an A/D converter. The input section 523 composed of a keyboard and a mouse is connected to the I/O interface 521f and a user uses the input section 523 so as to input data to the computer 52a. In addition, the I/O interface 521f is connected to the three measuring units 51, 51 and 51 so as to send and receive data to and from the respective three measuring units 51, 51 and 51.

The communication interface 521g is an Ethernet (registered trade name) interface. The communication interface 521g is connected to the system control apparatus 8 via a LAN. Via the communication interface 521g, the computer 52a can send and receive data to and from the system control apparatus 8 connected to the LAN by using a predetermined communication protocol. In addition, the communication interface 521g is connected to the host computer 9 and each of the specimen transport apparatus 3, 3, and 3 via the LAN so as to communicate therewith.

The image output interface 521h is connected to the image display section 522 composed of a LCD or a CRT so as to output a picture signal corresponding to the image data provided from the CPU 521a to the image display section 522. The image display section 522 displays an image (screen) in accordance with an input picture signal.

<Configuration of Smear Preparing Apparatus 6>

The smear preparing apparatus 6 aspirates a blood specimen so as to deliver it onto a slide glass by drops, spreads and dries the blood specimen on the slide glass, and supplies a stain solution to the slide glass so as to stain the blood on the slide glass. In this manner, the smear preparing apparatus prepares a smear.

Figure 14:
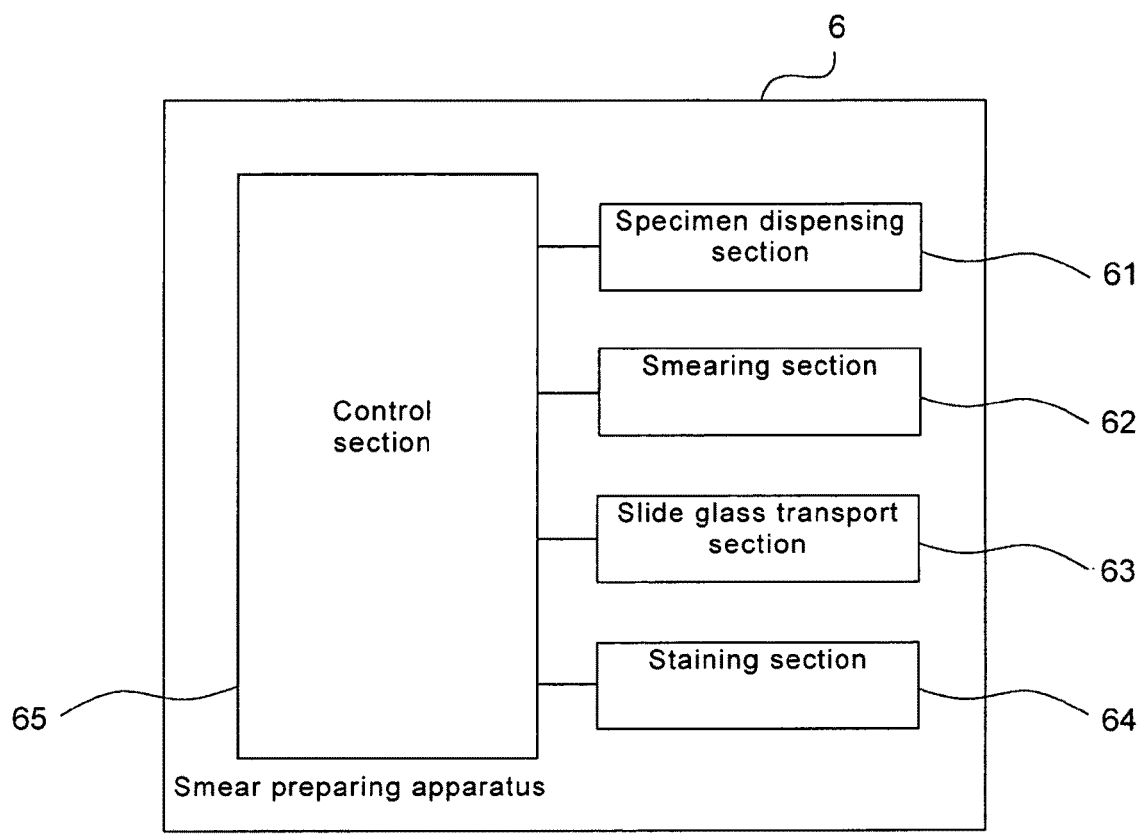
FIG. 14 is a block diagram showing the schematic configuration of a smear preparing apparatus.

FIG. 14 is a block diagram showing the schematic configuration of the smear preparing apparatus 6. As shown in FIG. 14, the smear preparing apparatus 6 includes a specimen dispensing section 61, a smearing section 62, a slide glass transport section 63, a staining section 64 and a control section 65.

The specimen dispensing section 61 includes an aspiration tube (not shown) and the aspiration tube is stuck into the cap section CP of a specimen container T in the sample rack L transported on the measuring line 31a of the specimen transport apparatus 3 so as to aspirate a blood specimen from the specimen container T. The specimen dispensing section 61 is configured to drop the aspirated blood specimen onto a slide glass. The smearing section 62 is configured to smear and dry the blood specimen dropped onto the slide glass and perform printing on the slide glass.

The slide glass transport section 63 is provided to accommodate the slide glass on which the blood specimen is smeared by the smearing section 62 in a cassette (not shown) and to transport the cassette. The staining section 64 supplies a stain solution to the slide glass in the cassette transported to a staining position by the slide glass transport section 63. The control section 65 controls the specimen dispensing section 61, the smearing section 62, the slide glass transport section 63 and the staining section 64 in accordance with a smear preparing instruction issued from the specimen transport apparatus 3 so as to perform the above smear preparing operation.

<Configuration of System Control Apparatus 8>

The system control apparatus 8 is composed of a computer and controls the entire specimen processing system 1. The system control apparatus 8 receives the number of the sample rack L from the specimen putting apparatus 2 and determines the transport destination of the sample rack L.

The system control apparatus 8 is realized by a computer 8a. As shown in FIG. 13, the computer 8a includes a main body 81, an image display section 82 and an input section 83. The main body 81 includes a CPU 81a, a ROM 81b, a RAM 81c, a hard disk 81d, a reading device 81e, an I/O interface 81f, a communication interface 81g and an image output interface 81*h*. The CPU 81*a*, ROM 81*b*, RAM 81*c*, hard disk 81*d*, reading device 81*e*, I/O interface 81*f*, communication interface 81*g* and image output interface 81*h* are connected to each other by a bus 81*j*.

In the hard disk 81*d*, various computer programs for being executed by the CPU 81*a*, such as an operating system and an application program, and data which are used to execute the computer programs are installed. A system control program 84*a* to be described later is also installed in the hard disk 81*d*.

The reading device 81*e* is composed of a flexible disk drive, a CD-ROM drive, a DVD-ROM drive or the like and can read the computer program or data recorded in a portable recording medium 84. In the portable recording medium 84, the system control program 84*a* for prompting the computer to function as the system control apparatus 8 is stored. The computer 8*a* can read the system control program 84*a* from the portable recording medium 84 so as to install the system control program 84*a* in the hard disk 81*d*.

The I/O interface 81*f* is composed of, for example, a serial interface such as USB, IEEE 1394 or RS-232C, a parallel interface such as SCSI, IDE or IEEE1284, and an analog interface including a D/A converter and an A/D converter. The input section 83 composed of a keyboard and a mouse is connected to the I/O interface 81*f* and a user uses the input section 83 so as to input data to the computer 52*a*.

The communication interface 81*g* is an Ethernet (registered trade name) interface. The communication interface 81*g* is connected to the specimen putting apparatus 2, the specimen transport apparatus 3, the specimen accommodating apparatus 4, the information processing unit 52 and the host computer 9 via a LAN. Via the communication interface 81*g*, the computer 8*a* can send and receive data to and from the above respective apparatuses connected to the LAN by using a predetermined communication protocol.

Since the other configurations of the system control apparatus 8 are the same as the configurations of the above-described information processing unit 52, a description thereof will be omitted.

<Configuration of Host Computer 9>

The host computer 9 is composed of a computer and includes a CPU, a ROM, a RAM, a hard disk, a communication interface and the like. The communication interface is connected to the above-described LAN so as to communicate with the system control apparatus 8 and the information processing unit 52 of the blood cell analyzing apparatus 5. In the hard disk, measuring orders are stored. The measuring orders include specimen IDs and information on measuring items of objects. When receiving request data for a measuring order including a specimen ID from another apparatus, the host computer 9 reads measuring data corresponding to the specimen ID from the hard disk and transmits the measuring data to the apparatus as a request source. Since the other configurations of the host computer 9 are the same as the configurations of the above-described other computers, a description thereof will be omitted.

Hereinafter, an operation of the specimen processing system 1 according to this embodiment will be described.

<Operation of Specimen Putting Apparatus 2>

Specimen Sorting Operation

Figure 15A:
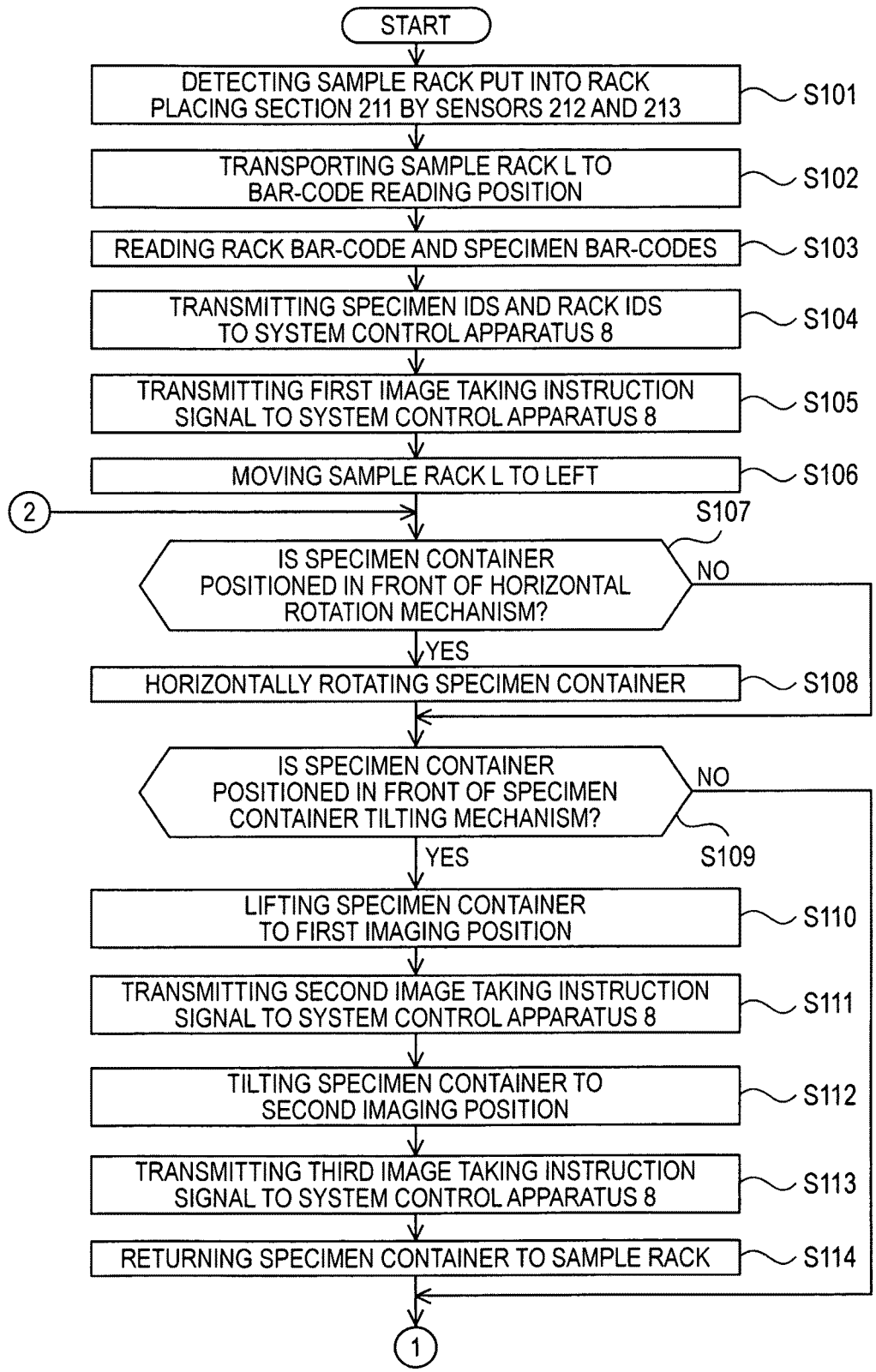
FIG. 15A is a flowchart (first half) showing the flow of a specimen sorting operation of a specimen putting apparatus.
Figure 15B:
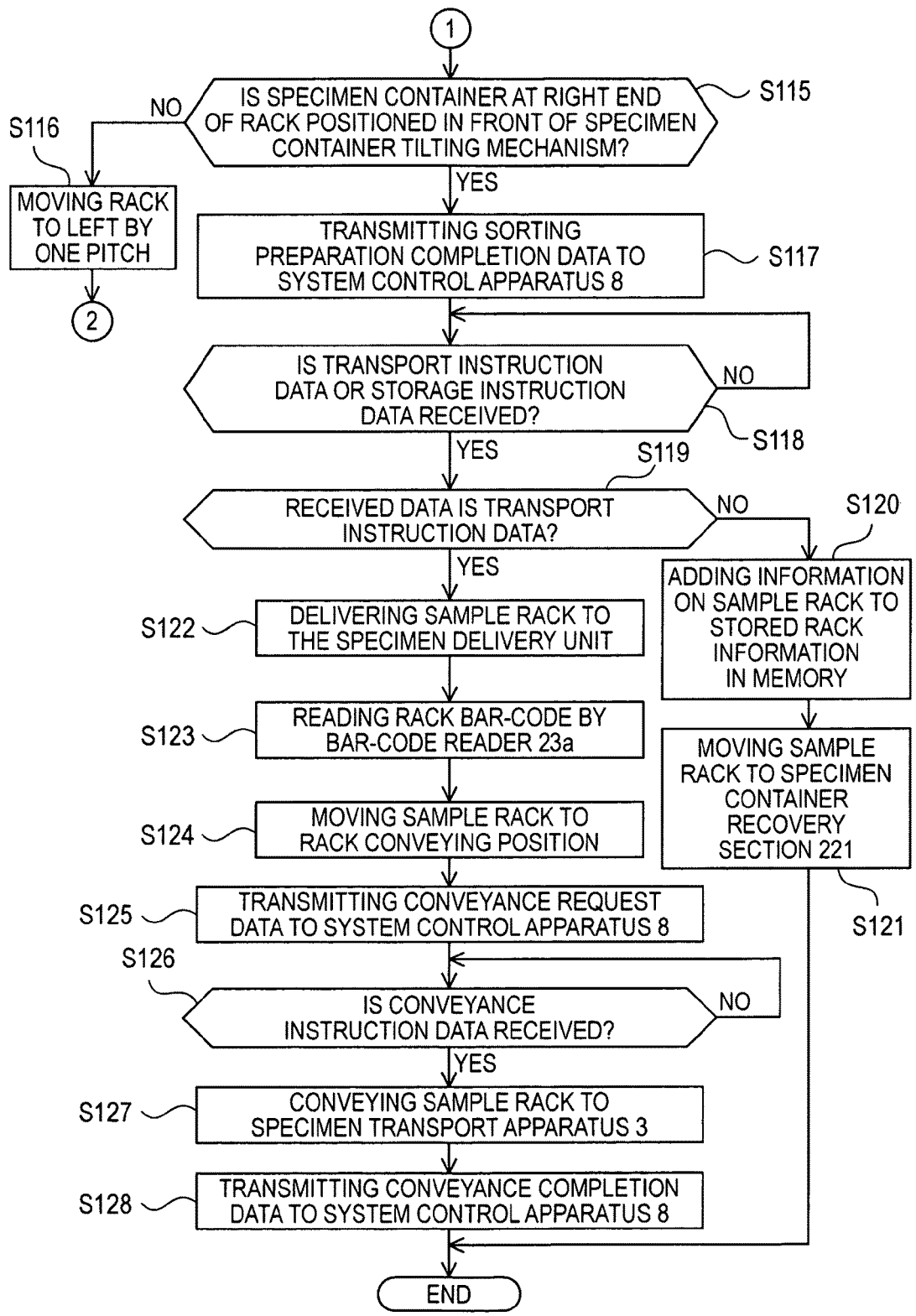
FIG. 15B is a flowchart (second half) showing the flow of the specimen sorting operation of the specimen putting apparatus.

When a specimen is put into the specimen processing system 1, the specimen putting apparatus 2 sorts the sample rack L as to whether it is a rack to be transported to the measuring unit 51 or not. FIGS. 15A and 15B are flowcharts showing the flow of the specimen sorting operation of the specimen putting apparatus 2. A user places the sample rack L accommodating the specimen containers T on the rack placing section 211 of the specimen setting section 21 and operates the operating panel 214 of the specimen setting section 21 so as to issue an analysis start instruction to the specimen processing system 1. The control section 2*a* of the specimen putting apparatus 2 detects the sample rack L put into the rack placing section 211 by the sensors 212 and 213 when receiving the analysis start instruction (Step S101). When an event occurs in which the sensors 212 and 213 detect the sample rack L, the control section 2*a* starts the movement of the sample rack L. The sample rack L placed on the rack placing section 211 of the specimen setting section 21 is moved backward on the rack placing section 211 and reaches the bar-code reading position (Step S102).

Next, the control section 2*a* reads the specimen IDs of the specimens accommodated in the sample rack L and the rack ID of the sample rack L by the bar-code readers 21*b* and 21*c* (Step S103). At this time, each of the specimen containers T is horizontally rotated by the horizontal rotation mechanism 21*d* while being held in the sample rack L, and the specimen bar-code is read when the bar-code label BL1 faces the bar-code reader 21*b*. In addition, the control section 2*a* transmits the read specimen IDs and rack IDs to the system control apparatus 8 (Step S104). In the data transmitted in Step S104, holding positions (1 to 10) of the specimen containers T in the sample rack L correspond to the specimen IDs of the held specimen containers. When the specimen ID cannot be obtained due to a failure to read the specimen bar-code, data is transmitted indicating the reading failure of the specimen bar-code associated with the holding position.

Further, the control section 2*a* lowers the CCD camera 21*e* and the white LED 21*f*, which have been retreated upward so as not to interfere with the movement of the sample rack L on the rack placing section 211, so as to transmit a first image taking instruction signal to the system control apparatus 8 (Step S105). As described later, the system control apparatus 8 takes an image captured by the camera 21*e* when receiving the first image taking instruction signal, and then performs image processing on the image and detects the shape of the specimen container accommodated in the sample rack L. Then, the control section 2*a* moves the sample rack L to the left so as to deliver the sample rack L to the specimen checking unit 22.

The control section 2*a* moves the sample rack L, which is introduced into the specimen checking unit 22, to the left for every pitch by the transport belt 228 of the specimen container collect section 221 (Step S106). The control section 2*a* determines whether the specimen container T is positioned in front of the horizontal rotation mechanism 223 (Step S107). This process is performed by referring to, for example, a light-receiving level of the light-receiving element 223*c* of the optical sensor 223*a*. When the specimen container T is not positioned in front of the horizontal rotation mechanism 223 (No in Step S107), the control section 2*a* performs a process of Step S109. On the other hand, when the specimen container T is positioned in front of the horizontal rotation mechanism 223 (Yes in Step S107), the control section 2*a* drives the horizontal rotation mechanism 223 so as to horizontally rotate the specimen container T to thereby turn the bar-code label BL1 to the front (Step S108). In this process, the control section 2*a* compares a light-receiving level of the light-receiving element 223*c* of the optical sensor 223*a* with a predetermined value while bringing the contacting section 223*d* into contact with the cap section CP of the specimen container T and rotating the contacting section, and horizontally rotates the specimen container T until the light-receiving level is equal to or more than the predetermined value. In this manner, the bar-code label BL1 is turned to the front.

Subsequently, the controller 2a determines whether the specimen container T is disposed in front of the specimen container tilting mechanism 224 (Step S109). This process is performed by, for example, determining how many times the specimen container T disposed in front of the horizontal rotation mechanism 223 has been subjected to pitch feeding. When the specimen container T is not disposed in front of the specimen container tilting mechanism 224 (No in Step S109), the controller 2a performs a process of Step S115. When the specimen container T is disposed in front of the specimen container tilting mechanism 224 (Yes in Step S109), the controller 2a grasps the specimen container T by the grasping section 224a so as to lift the specimen container to the first imaging position on the upper side (Step S110), and transmits a second image taking instruction signal to the system control apparatus 8 (Step S111). As described later, the system control apparatus 8 takes an image captured by the camera 225a when receiving the second image taking instruction signal, and then performs image processing on the image and detects the blood volume in the specimen container T.

Next, the controller 2a vertically turns the grasping section 224a by a predetermined angle so as to tilt the specimen container T to the second imaging position (Step S112) and transmits a third image taking instruction signal to the system control apparatus 8 (Step S113). As described later, the system control apparatus 8 takes an image captured by the camera 225b when receiving the third image taking instruction signal, and then performs image processing on the image and determines the presence or absence of blood coagulation in the specimen container T.

Next, the controller 2a turns the grasping section 224a in the counter direction to return the specimen container T to the vertical state again, and moves the grasping section 224a downward so as to accommodate the specimen container T in the sample rack L (Step S114).

Herein, in order to simplify the description, the processes of Steps S107 to S108 and the processes of Steps S109 to S114 have been described so as to be sequentially performed. However, actually, the processes are performed in parallel. That is, for example, while one specimen container T stored in the sample rack L is horizontally rotated, a different specimen container T is pulled from the sample rack L of the specimen containers T.

The controller 2a determines whether all the specimen containers T stored in the sample rack L have been subjected to the above processes, or more precisely, whether a specimen container accommodating section at the right end of the sample rack L is positioned in front of the specimen container tilting mechanism 224 (Step S115). When the right end of the sample rack L is not yet positioned in front of the specimen container tilting mechanism 224 (No in Step S115), the controller moves the sample rack L to the left by one pitch (Step S116) and returns the process to Step S107.

When the right end of the sample rack L is positioned in front of the specimen container tilting mechanism 224 (Yes in Step S115), the control section 2a transmits sorting preparation completion data to the system control apparatus 8 (Step S117) and then stands by to receive transport instruction data or storage instruction data (No in Step S118). The transport instruction data is transmitted from the system control apparatus 8 when the sample rack L accommodates only the specimens to be provided for the blood cell analysis of the blood cell analyzing apparatus 5, and the storage instruction data is transmitted from the system control apparatus 8 when the sample rack L accommodates a specimen which is not to be provided for the blood cell analysis of the blood cell analyzing apparatus 5.

Figure 16:
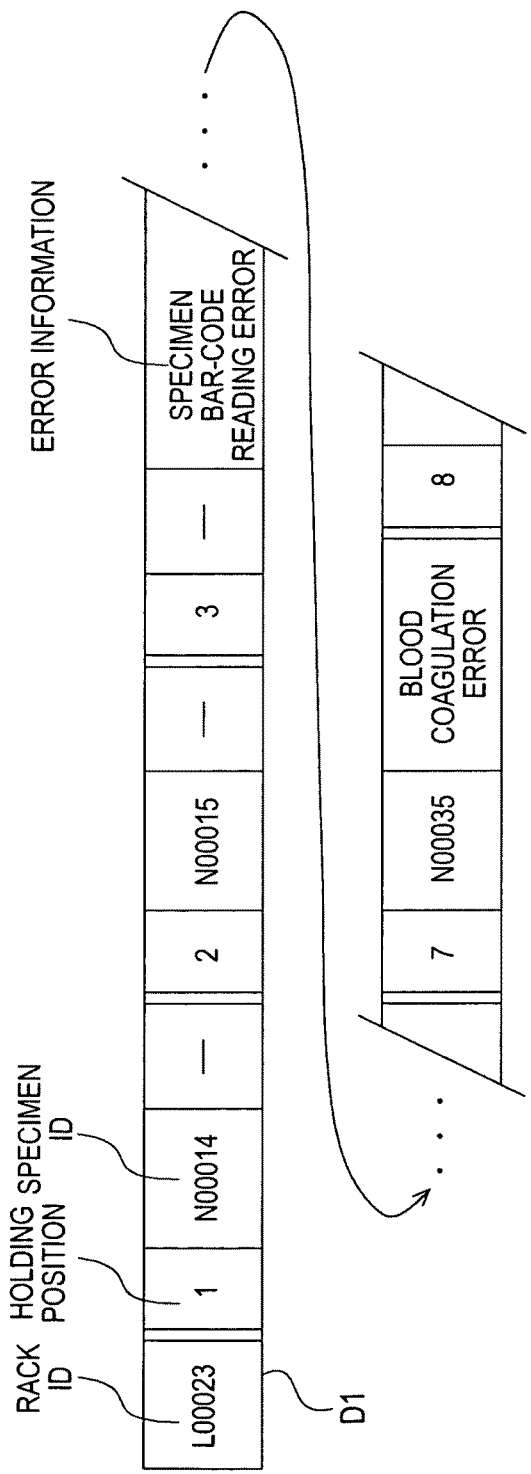
FIG. 16 is a schematic diagram showing the structure of storage instruction data.

When receiving the transport instruction data or the storage instruction data (Yes in Step S118), the control section 2a determines the received data is the storage instruction data (Step S119). FIG. 16 is a schematic diagram showing the structure of the storage instruction data. Storage instruction data D1 includes the rack ID of the sample rack L, the holding positions (1 to 10) of the specimen containers T in the sample rack L, the specimen IDs of the specimen containers T and error information (abnormal code) indicating the contents of abnormality. The holding position, the specimen ID and the error information of the specimen container T correspond to each other, and the holding position, the specimen ID and the error information of the specimen container T in which an error has occurred can be specified.

In Step S119, when the received data is the storage instruction data (No in Step S119), the control section 2a adds the information on the sample rack L to the stored rack information in the memory of the control section 2a on the basis of the storage instruction data (Step S120). FIG. 17 is a schematic diagram showing the structure of the stored rack information. As shown in the drawing, stored rack information D2 includes the rack IDs, the specimen IDs of the holding positions and the error information of the holding positions. The specimen ID and the error information correspond to each other, and it is possible to specify which specimen has which kind of error. In such stored rack information D2, the information relating to all the sample racks L accommodated in the specimen container collect section 221 is included. After that, the control section 2a moves the sample rack L to the specimen container collect section 221 by using the rack delivery section 229 (Step S121) and completes the process.

In Step S119, when the received data is the transport instruction data (Yes in Step S119), the control section 2a further moves the sample rack L to the left so as to deliver the sample rack L to the specimen feeding unit 23 (Step S122). The control section 2a reads the rack bar-code of the sample rack L by using the bar-code reader 23a (Step S123) and moves the sample rack L to the rack conveying position for conveying the sample rack L to the following specimen transport apparatus 3 (Step S124). Then, the control section 2a transmits conveyance request data including the rack ID of the sample rack L to the system control apparatus 8 (Step S125) and stands by to receive conveyance instruction data to be transmitted from the system control apparatus 8 (No in Step S126). When receiving the conveyance instruction data from the system control apparatus 8 (Yes in Step S126), the specimen putting apparatus 2 conveys the sample rack L to the adjacent specimen transport apparatus 3 (Step S127) and transmits conveyance completion data to the system control apparatus 8 (Step S128). After that, the control section 2a completes the process.

Retreated Rack Information Display Operation

Figure 18A:
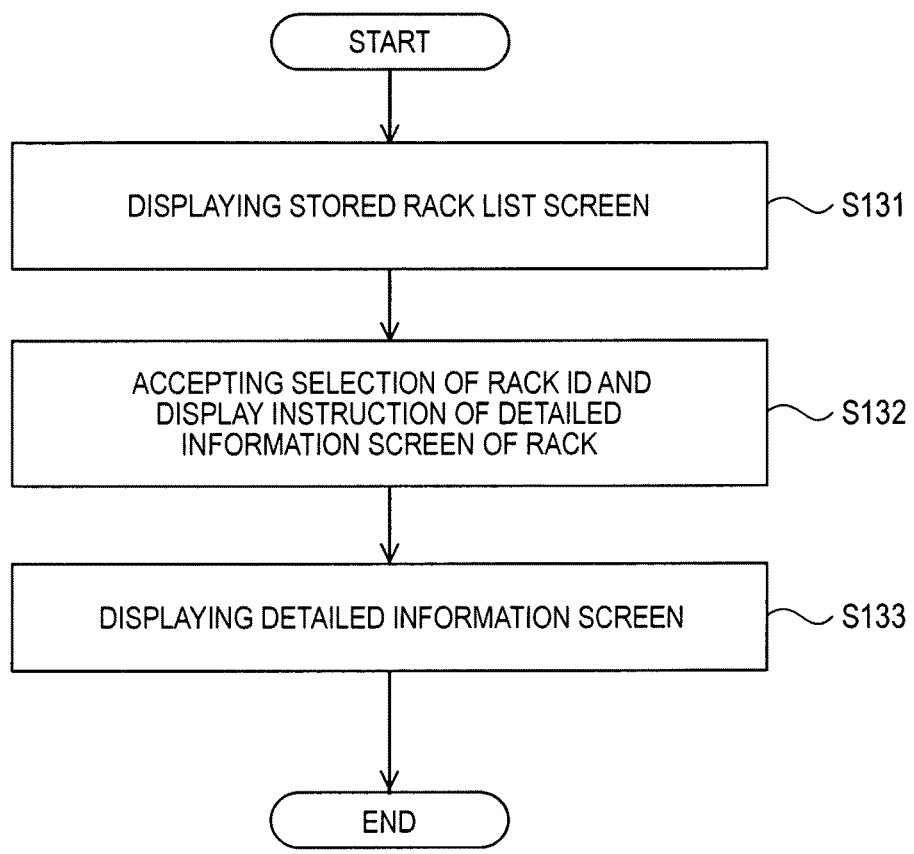
FIG. 18A is a flowchart showing the flow of a retreated rack information display operation of the specimen putting apparatus.

The information relating to the sample rack L, which is retreated to the specimen container collect section 221 of the specimen checking unit 22 as described above, is displayed on the liquid crystal display section 227 of the specimen checking unit 22. FIG. 18A is a flowchart showing the flow of the retreated rack information display operation. When the storage instruction data D1 is transmitted from the system control apparatus 8, the stored rack information D2 of the control section 2a is updated and the sample rack L is moved to the specimen container collect section 221, the control section 2a displays a stored rack list screen on the liquid crystal display section 227 on the basis of the stored rack information D2 (Step S131).

Figure 19:
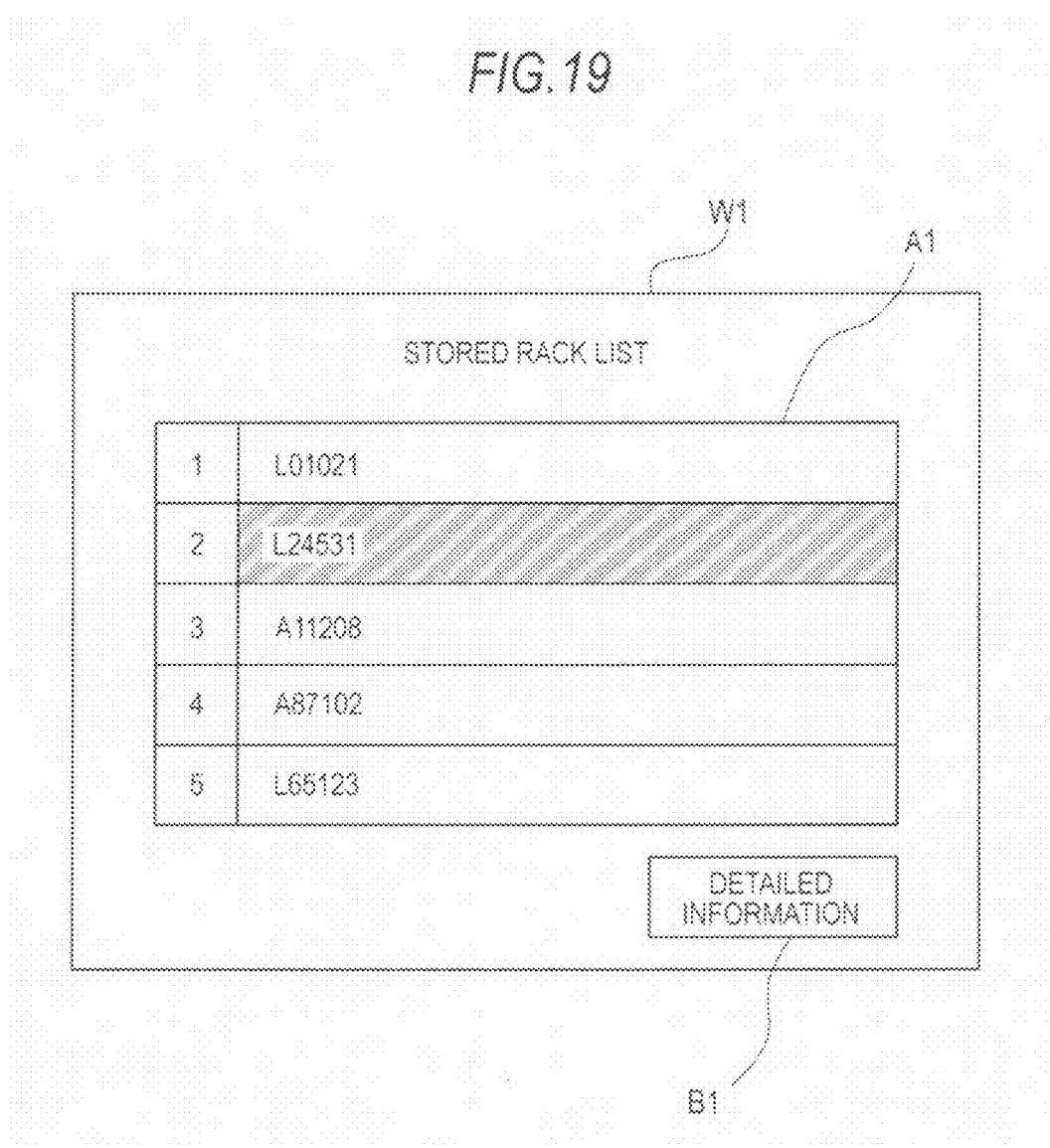
FIG. 19 is a diagram showing an example of a stored rack list screen.

FIG. 19 is a diagram showing an example of the stored rack list screen. As shown in the drawing, in a stored rack list screen W1, a list display area A1 is provided in which the rack IDs of the sample racks L in which an abnormality has been detected are displayed as a list. In the list display area A1, an operator touches each rack ID with a finger so as to select the rack ID. The selected rack ID is displayed with a color different from that of the rack IDs which are not selected. In addition, in the stored rack list screen W1, a display switching button B1 is provided for switching the screen display into a detailed information screen of the rack ID selected in the list display area A1. When accepting the selection of the rack ID from the operator and a display instruction of the detailed information screen of the sample rack L (Step S132), the control section 2a displays the detailed information screen on the liquid crystal display section 227 (Step S133). The operator may not operate the touch panel so as to select the rack ID and input the display instruction of the detailed information screen, but may read the rack bar-code of the sample rack L by the handy bar-code reader 222c so as to input the read rack ID to the control section 2a to thereby display the detailed information screen of the sample rack L. After displaying the detailed information screen, the control section 2a completes the process.

Figure 20:
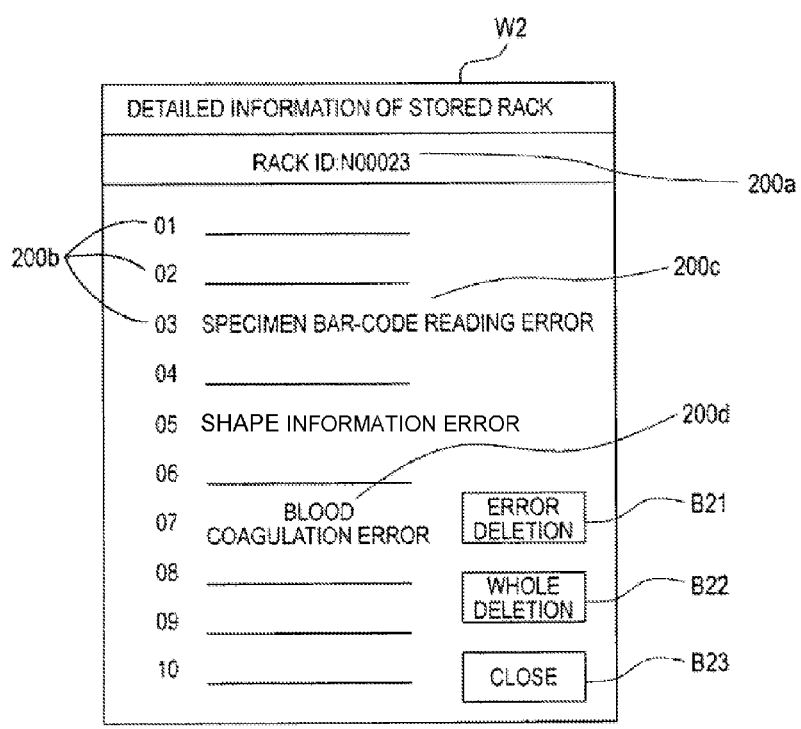
FIG. 20 is a diagram showing an example of a detailed information screen of a sample rack.

FIG. 20 is a diagram showing an example of the detailed information screen of the sample rack L. As shown in the drawing, a detailed information screen W2 includes a rack ID 200a, holding position numbers 200b in the sample rack and error information 200c and 200d corresponding to the holding positions. The error information 200c is information indicating the failure in specimen bar-code reading and the error information 200d is information indicating the coagulated blood. Furthermore, the detailed information screen W2 is provided with a first delete button B21 for deleting the information on the sample rack L, a second delete button B22 for deleting the selected error information and a close button B23 for instructing the completion of the display of this screen. In the detailed information screen W2, desired error information can be selected through the touch panel operation of the operator. In a state in which the error information is selected in this manner, the operator selects the second delete button B22 and thus can input an instruction to delete the error information. Moreover, by selecting the specimen bar-code reading error, taking out the specimen container T in which the specimen bar-code reading has failed from the sample rack L, and re-reading the specimen bar-code with the handy bar-code reader 222c, the operator can solve the specimen bar-code reading error.

By confirming such a detailed information screen, the operator can take an appropriate action, such as taking out the specimen container T in which the blood is coagulated from the sample rack L and analyzing the blood specimen by using a manual method, or taking out the specimen container T in which the bar-code reading has failed, re-reading the specimen bar-code by using the handy bar-code reader 222c, returning the specimen container to its original holding position in the sample rack L and placing the sample rack L in the rack re-putting section 231 of the specimen feeding unit 23.

Figure 18B:
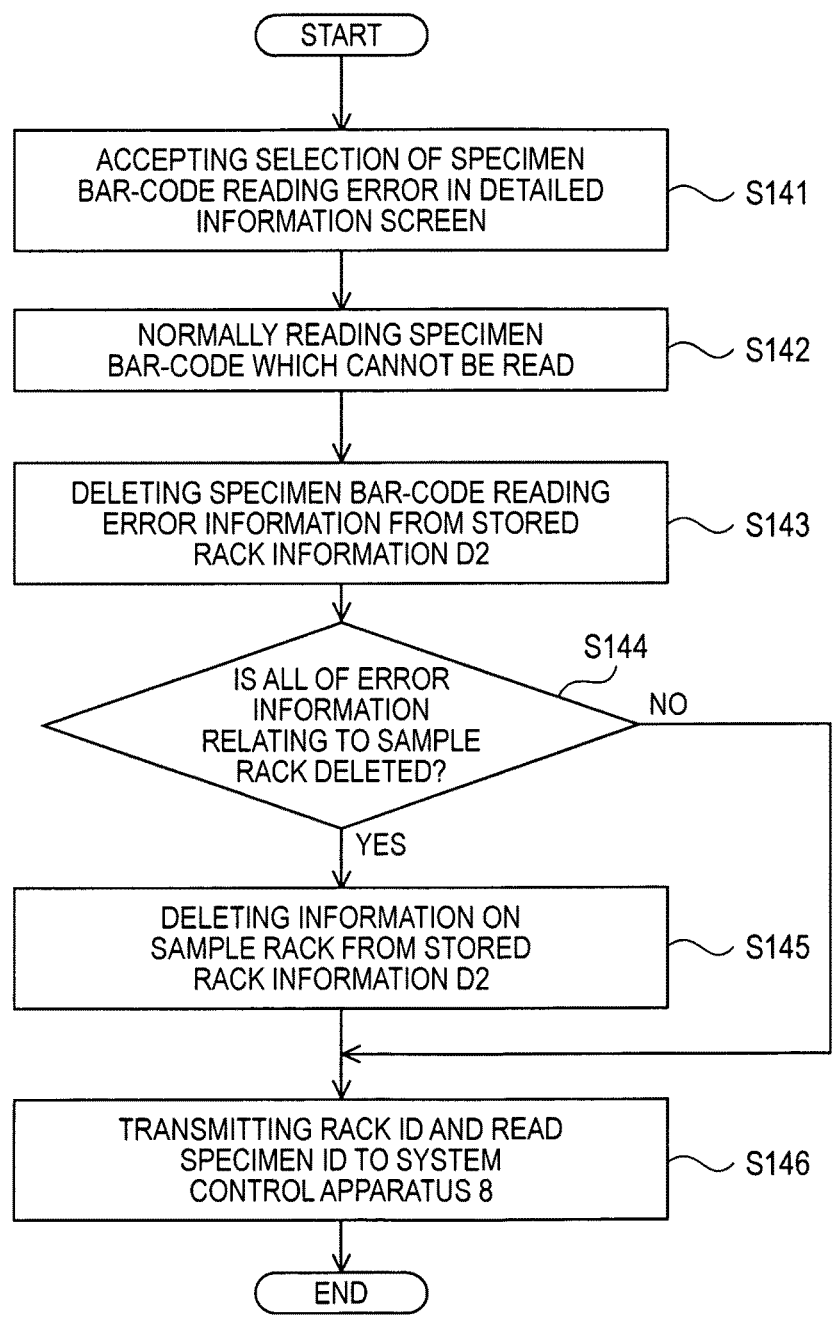
FIG. 18B is a flowchart showing the flow of a bar-code re-reading operation of the specimen putting apparatus.

FIG. 18B is a flowchart showing the flow of the bar-core re-reading operation. This operation is an operation when the operator re-reads the specimen bar-code, which cannot be read, by using the handy bar-code reader 222c in a state in which the detailed information screen is displayed. When an event occurs in which the selection of the specimen bar-code reading error by the operator is accepted (Step S141) and the specimen bar-code which cannot be read is normally read (Step S142), the specimen bar-code reading error information is deleted from the stored rack information D2 (Step S143). Next, the control section 2a determines whether all the error information relating to the sample rack L in the stored rack information D2 is deleted (Step S144). When all the error information relating to the sample rack L is deleted in the stored rack information D2 (Yes in Step S144), the control section 2a deletes the information on the sample rack L from the stored rack information D2 (Step S145) and performs a process of Step S146. On the other hand, when any error information relating to the sample rack L remains in the stored rack information D2 (No in Step S144), the control section 2a performs the process of Step S146.

In Step S146, the control section 2a transmits the rack ID of the sample rack and the read specimen ID to the system control apparatus 8 (Step S146). Then, the control section 2a completes the process. The system control apparatus 8 receiving the specimen ID makes an inquiry to the host computer 9 for a measuring order by using the specimen ID as a key, and deletes from the hard disk 81d the error information corresponding to the specimen ID.

Figure 18C:
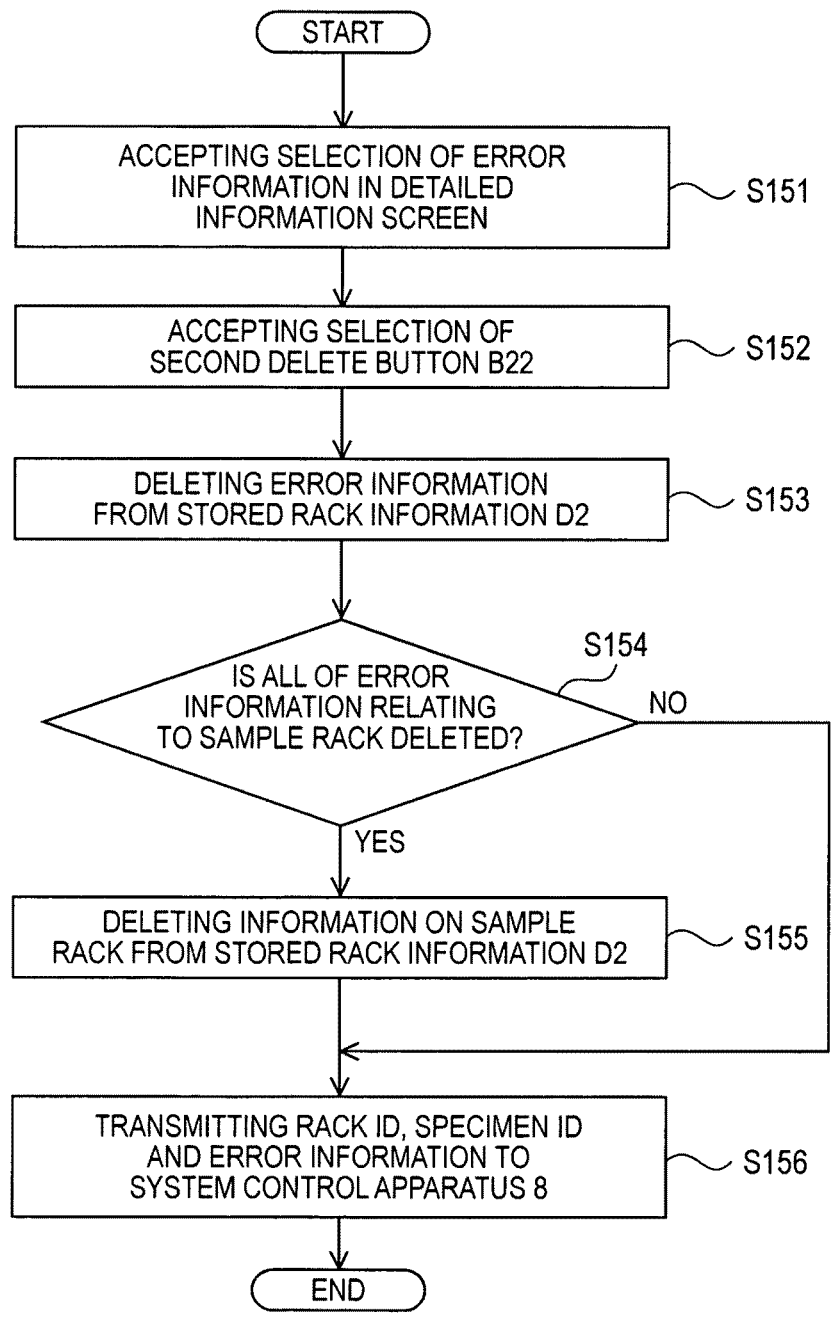
FIG. 18C is a flowchart showing the flow of an error information removing operation of the specimen putting apparatus.

FIG. 18C is a flowchart showing the flow of the error information removing operation. This operation is an operation when the operator selects the displayed error information and deletes the error information in a state in which the detailed information screen is displayed. For example, in some cases, the operator moves a coagulated specimen to another specimen container or removes a clot to make the specimen in which an error is detected measurable. In this case, the operator returns the specimen which is made measurable to its original position in the sample rack L and deletes the error information displayed in the detailed information screen so that the sample rack L can be re-put in the system. When an event occurs in which the selection of the error information in the detailed information screen by the operator is accepted (Step S151) and an instruction is received so as to delete the error information, that is, when an event occurs in which the selection of the second delete button B22 is accepted (Step S152), the error information is deleted from the stored rack information D2 (Step S153). Next, the control section 2a determines whether all the error information relating to the sample rack L in the stored rack information D2 is deleted (Step S154). When all the error information relating to the sample rack L is deleted in the stored rack information D2 (Yes in Step S154), the control section 2a deletes the information on the sample rack L from the stored rack information D2 (Step S155) and performs a process of Step S156. On the other hand, when any error information relating to the sample rack L remains in the stored rack information D2 (No in Step S154), the control section 2a performs the process of Step S156.

In Step S156, the control section 2a transmits the rack ID of the sample rack, the deleted error information and the specimen ID to the system control apparatus 8 (Step S156). Then, the control section 2a completes the process. The system control apparatus 8 receiving the data deletes the error information corresponding to the specimen ID from the hard disk 81d.

In this manner, the sample rack L is made to be re-put and can be then re-put into the rack re-putting section 231 of the specimen feeding unit 23. The sample rack L re-put into the rack re-putting section 231 is automatically conveyed to the specimen transport apparatus 3.

Figure 18D:
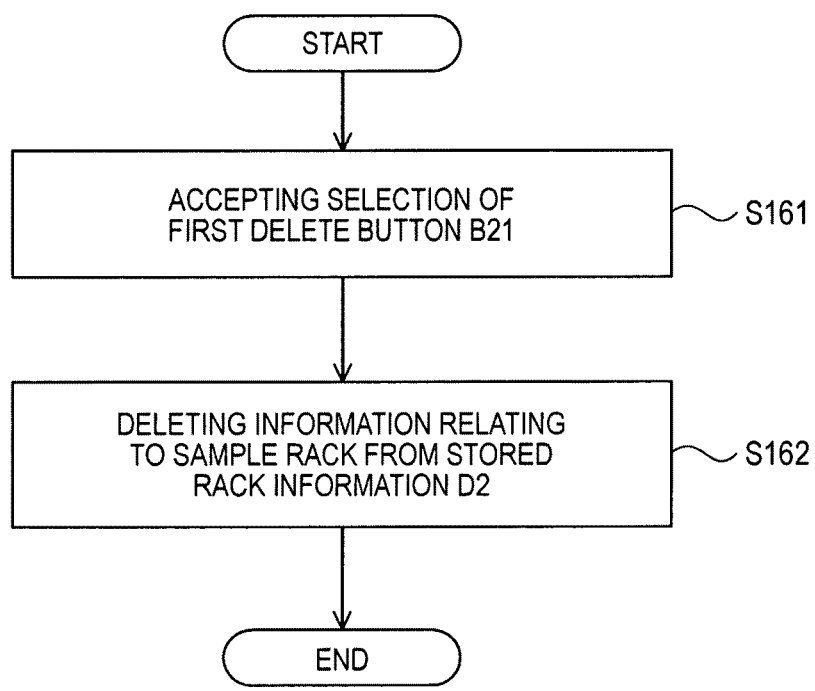
FIG. 18D is a flowchart showing the flow of a stored rack removing operation of the specimen putting apparatus.

FIG. 18D is a flowchart showing the flow of the stored rack removing operation. This operation is an operation when the operator removes the sample rack L from the specimen container collect section 221 so as to manually perform the examination, swap the bar-code label or place the sample rack L on the rack placing section 211 of the specimen setting section 21 again. When an event occurs in which the first delete button B21 is selected by the operator and an instruction is received to delete the information relating to the sample rack L from the stored rack information D2 in the control section 2a (Step S161), the control section 2a deletes the information relating to the sample rack L from the stored rack information D2 (Step S162) and completes the process. Then, the operator takes out the sample rack L from the specimen container collect section 221 and take the necessary action, such as manually examining the specimen which is coagulated or the specimen with an insufficient amount, swapping the bar-code which cannot be read, or re-putting into the rack placing section 211.

<Operation of System Control Apparatus 8>

Next, an operation of the system control apparatus 8 will be described.

Measuring Order Obtaining Operation

The system control apparatus 8 receives a specimen ID from the specimen putting apparatus 2 and makes an inquiry to the host computer 9 for a measuring order by using the specimen ID as a key. Herein, the measuring order is data indicating an instruction of an analysis item to be analyzed for the specimen, and includes attribute information on the specimen, such as the specimen ID, patient ID and the name of the patient, and information on the analysis item. Hereinafter, this operation will be described in detail.

Figure 21:
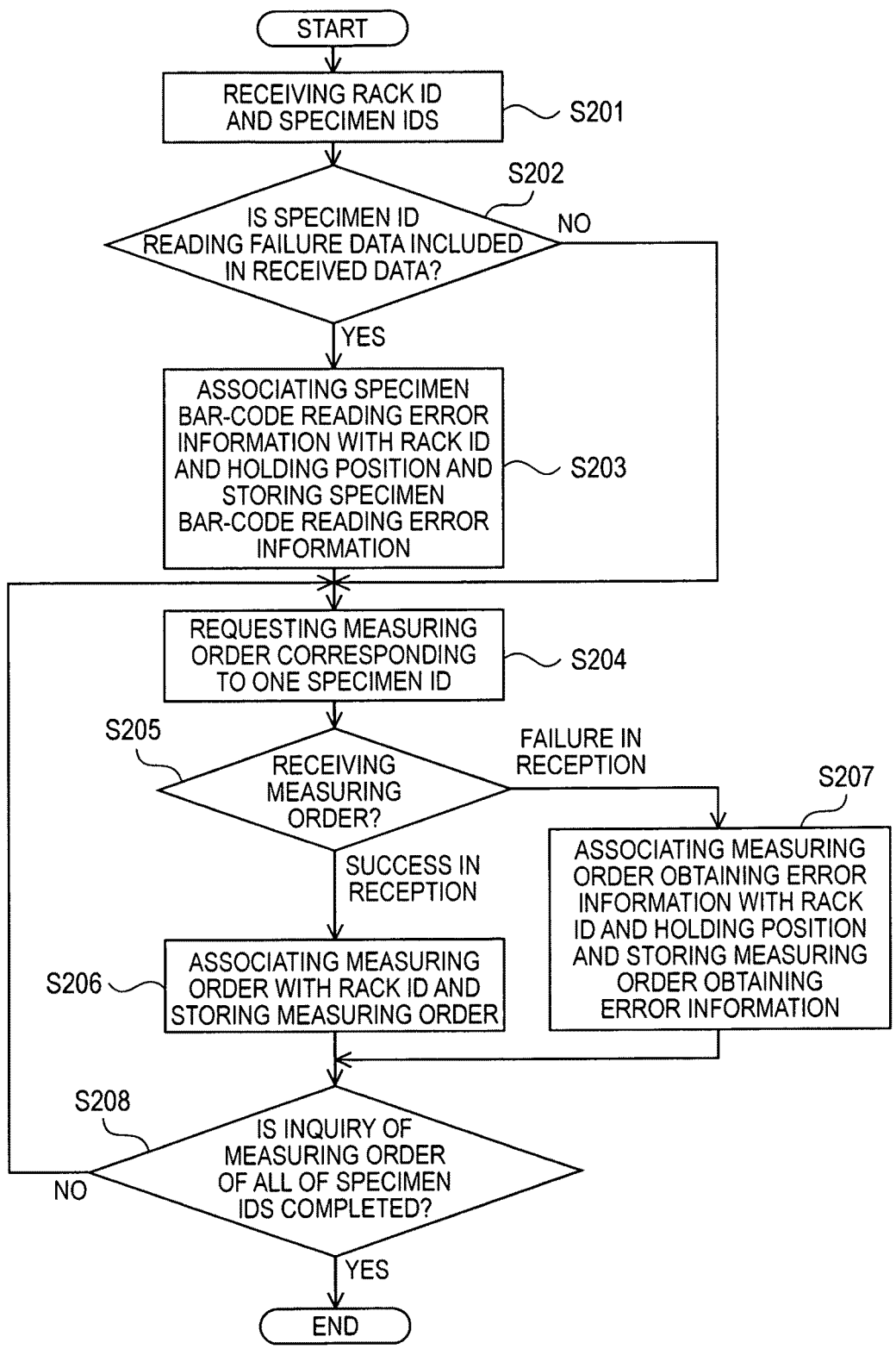
FIG. 21 is a flowchart showing the flow of a measuring order obtaining operation of a system control apparatus.

FIG. 21 is a flowchart showing the flow of the measuring order obtaining operation of the system control apparatus 8. As described above, the specimen putting apparatus 2 transmits the specimen IDs and rack ID read by the bar-code readers 21b and 21c to the system control apparatus 8. The rack ID and the specimen IDs are received by the communication interface 81g of the system control apparatus 8 (Step S201). In the CPU 81a, a process of Step S202 is invoked when an event occurs in which the rack ID and the specimen IDs are received.

In Step S202, the CPU 81a determines whether specimen ID reading failure data is included in the received data (Step S202). When the specimen ID reading failure data is included in the received data (Yes in Step S202), the CPU 81a stores in the hard disk 51d specimen bar-code reading error information, indicating that a specimen bar-code reading failure has occurred, which corresponds to the rack ID of the sample rack L (in the case of a rack ID reading failure, a rack sequential number sequentially assigned to the put sample rack L) and the holding position of the specimen container (Step S203), and performs a process of Step S204. On the other hand, when the specimen ID reading failure data is not included (No in Step S202), the CPU 81a performs the process of Step S204.

In Step S204, the CPU 81a transmits one of the received specimen IDs to the host computer 9 and requests a measuring order corresponding to the specimen ID from the host computer 9 (Step S204). The CPU 81a stands by to receive the measuring order (Step S205). When the system control apparatus 8 receives the measuring order transmitted from the host computer 9 ("success of reception" in Step S205), the CPU associates the received measuring order with the rack ID and stores the measuring order in the hard disk 81d (Step S206). On the other hand, when the measuring order corresponding to the specimen ID cannot be received (when the measuring order is not received within a predetermined reception period, or when information indicating that the corresponding measuring order does not exist is received from the host computer 9) ("failure of reception" in Step S205), the information indicating that the measuring order does not exist (measuring order obtaining error information) is associated with the rack ID and the holding position of the specimen container T and this information is stored (Step S207).

Next, the CPU 81a determines whether the specimen IDs corresponding to the rack ID, that is, the specimen IDs of all the specimens accommodated in the sample rack L with the rack ID have been subjected to an inquiry of measuring order (Step S208). When there is a specimen ID not subjected to the inquiry of measuring order (No in Step S208), the CPU returns the process to Step S204 and requests a measuring order corresponding to the specimen ID not yet subjected to the inquiry of measuring order from the host computer 9.

On the other hand, when all of the specimen IDs have been subjected to the inquiry of measuring order (Yes in Step S208), the CPU 81a completes the process.

Specimen Container Shape Detecting Operation

The system control apparatus 8 obtains an image of the specimen container T put into the specimen putting apparatus 2 so as to detect the shape of the specimen container on the basis of the image. Hereinafter, this operation will be described in detail.

Figure 22:
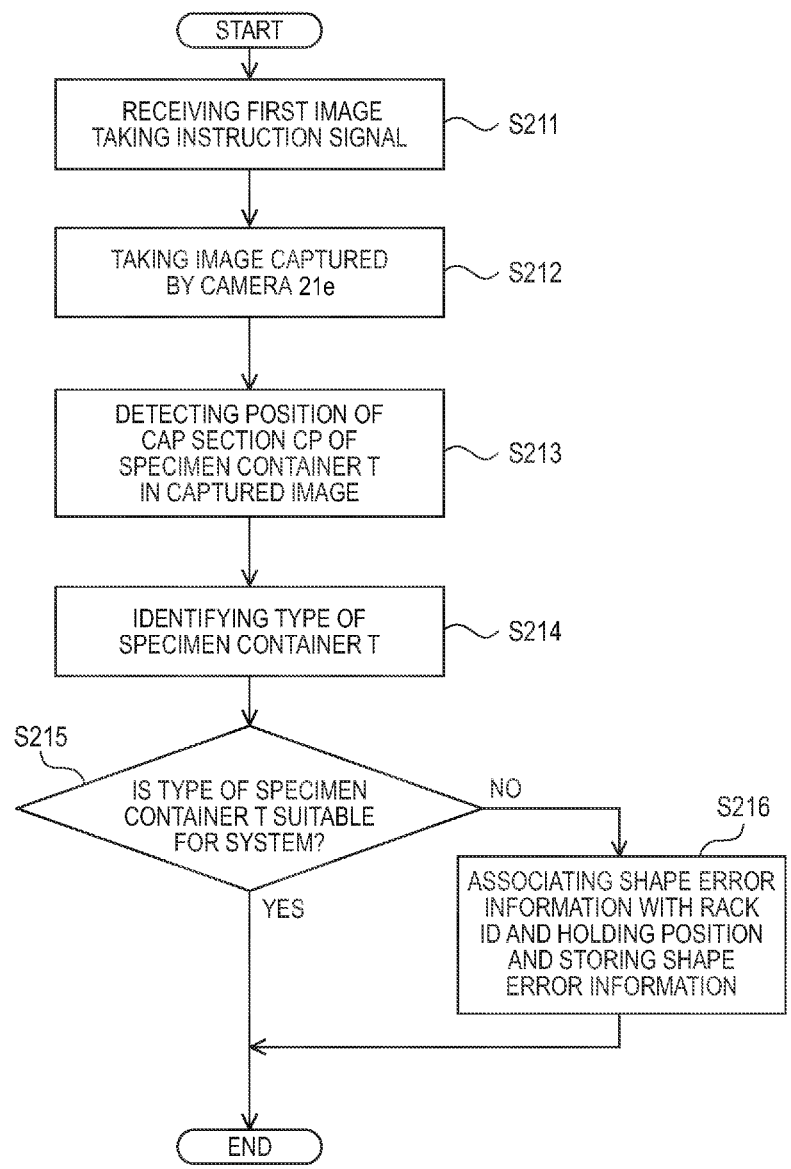
FIG. 22 is a flowchart showing the flow of a specimen container shape detecting process of the system control apparatus.

FIG. 22 is a flowchart showing the flow of the specimen container shape detecting operation of the system control apparatus 8. As shown in FIG. 22, in the CPU 81a of the system control apparatus 8, a process of Step S212 is invoked when an event occurs in which the system control apparatus 8 receives the first image taking instruction signal transmitted from the specimen putting apparatus 2 (Step S211).

In Step S212, the CPU 81a takes an image captured by the camera 21e at that time point (Step S212). The entire sample rack L is included in the captured image. Next, the CPU 81a detects the position of the cap section CP of each specimen container T in the taken, captured image (Step S213). This process will be described in detail. The cap section of a specimen container has a different color and a different shape in accordance with the type of the specimen container. Accordingly, in this process, the image captured by the camera 21e, which is a color image, is differentiated with respect to their R value, G value and B value. For example, in the case of the specimen container with a violet cap section, the differentiated R and B values in the peripheral portion of the cap section are larger (or smaller) than in another portion. In the case of the specimen container with a pink cap section, the differentiated R value in the peripheral portion of the cap section is larger (or smaller) than in another portion. Furthermore, since the cap section of the specimen container protrudes from the sample rack L, only an image of the part above the sample rack L becomes a processing object. Accordingly, it is possible to eliminate influences such as the color of the blood specimen transmitted from the specimen container. In this manner, the position of the cap section of the specimen container is detected by the differentiated R, G and B values. When the plural specimen containers T are accommodated in the sample rack L, plural cap sections are included in the image and the positions of the cap sections are detected in this process.

Next, the CPU 81a identifies the type of the specimen container on the basis of the color components of the pixels at the detected cap section position (Step S214). In order to perform this process, average R, G and B values of the pixels at the position of the cap section are obtained and the respective average values are compared with the information, which is stored in advance in the hard disk 51d, on the color components of the cap section for each type of specimen container. That is, for each type of specimen container, reference data on R, G and B values of the cap section is stored, and average R, G and B values obtained from the image are compared with the R, G and B values of the reference data. When both compared values are approximate to each other in a predetermined error range, it is judged that the type of the specimen container is that specific type. When the plural cap sections are imaged, each of the cap sections is subjected to the above-described process so as to specify the type of the specimen container.

Next, the CPU 81a performs a determining operation on the specimen containers of the sample rack L for determining whether the detected type of the specimen container is suitable for the specimen processing system 1 (Step S215). Herein, as the types of the specimen containers which are not suitable for the specimen processing system 1, there are included the specimen containers which have a size or shape failing to meet the configuration of the specimen container transport section 515 of the measuring unit 51 and in which the specimen cannot be aspirated by the measuring unit 51, and unknown types of specimen containers. In Step S215, when there is the specimen container which is determined as a type not suitable for the specimen processing system 1 (No in Step S215), the CPU 81a stores in the hard disk 51d shape error information, indicating that the shape of the specimen container is not suitable for the specimen processing system 1, which corresponds to the rack ID of the sample rack L and the holding position of the specimen container determined to be unsuitable (Step S216), and completes the process. On the other hand, when it is determined that all the types of the specimen containers are suitable for the specimen processing system 1 (Yes in Step S215), the CPU 81a completes the process.

Blood Volume Detecting Process

The system control apparatus 8 takes an image captured by the camera 225a and performs image processing on the captured image so as to detect the blood volume in the specimen container T.

Figure 23:
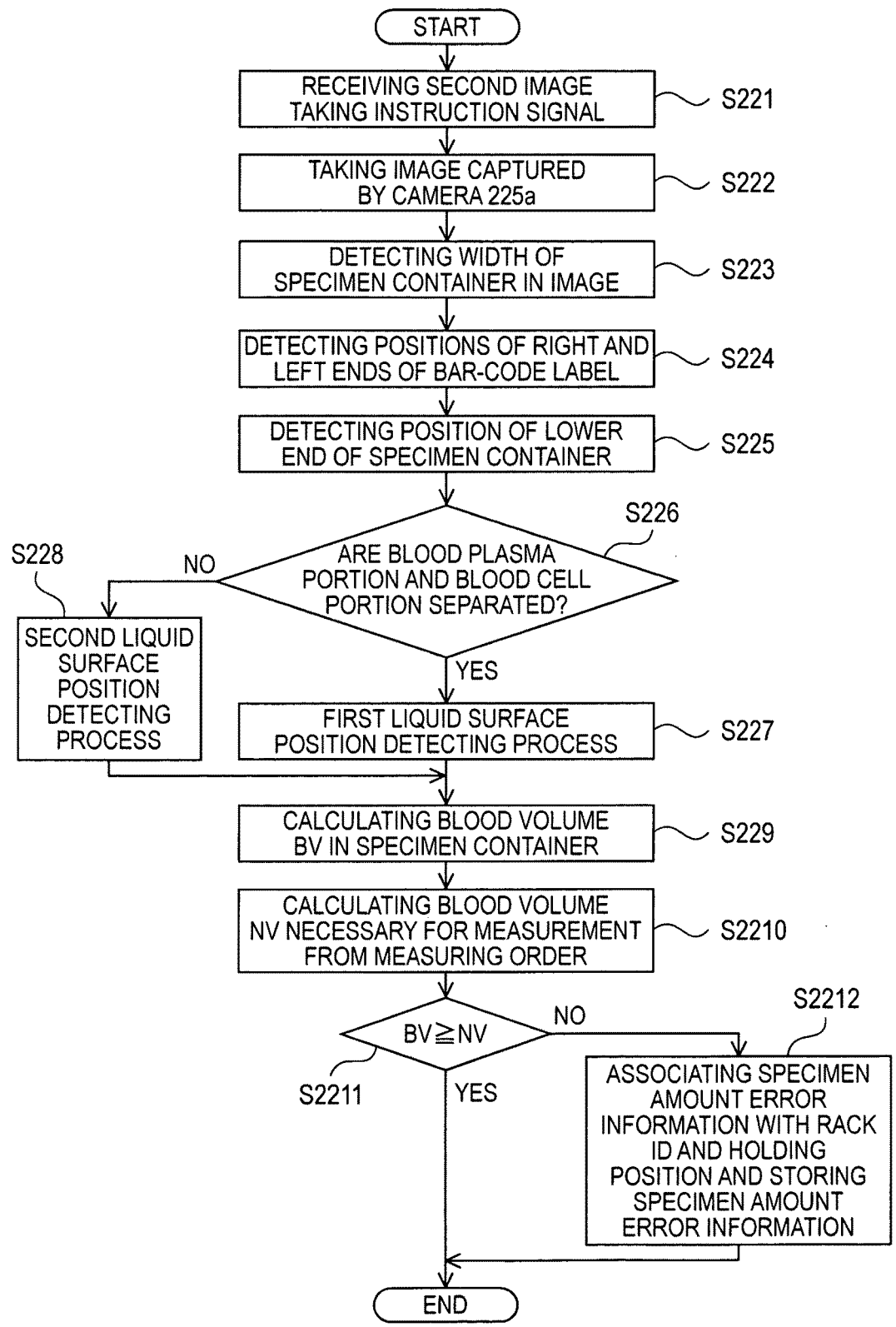
FIG. 23 is a flowchart showing the procedure of a blood volume detecting process of the system control apparatus.

FIG. 23 is a flowchart showing the procedure of the blood volume detecting process. As shown in FIG. 23, in the CPU 81a, a process of Step S222 is invoked when an event occurs in which the system control apparatus 8 receives the second image taking instruction signal transmitted from the specimen putting apparatus 2 (Step S221).

Figure 24:
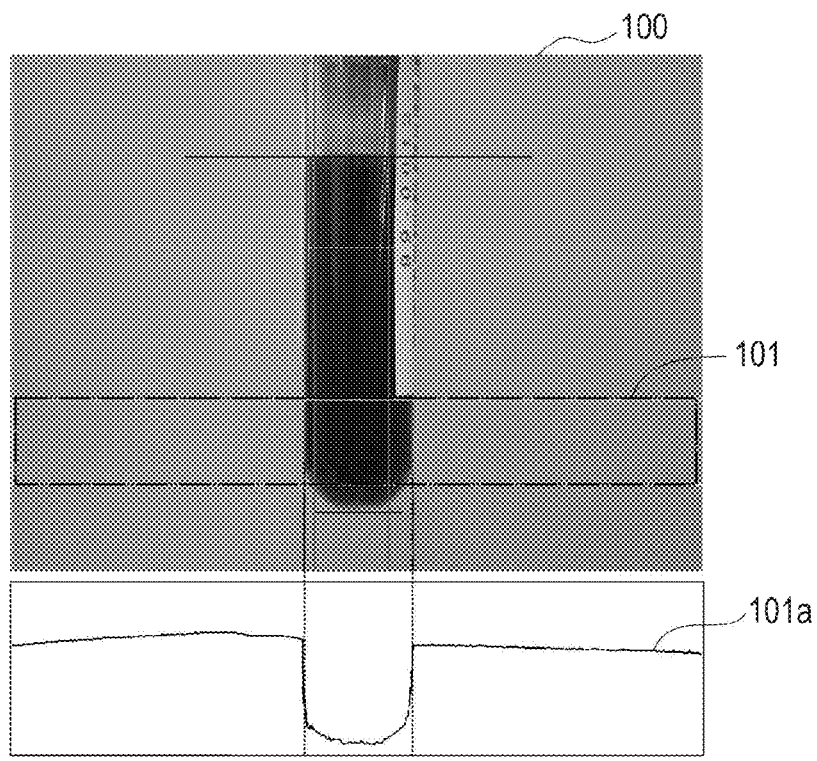
FIG. 24 is a schematic diagram for illustrating a process of detecting the width of a specimen container in an image.

In Step S222, the CPU 81a takes an image captured by the camera 225a at that time point (Step S222). Next, the CPU 81a detects the width of the specimen container T in the taken, captured image (Step S223). This process will be described in detail. FIG. 24 is a schematic diagram for illustrating the process of detecting the width of the specimen container T in the image. An image 100 is a color image and has luminance information of RGB of respective pixels. A processing area 101 for obtaining the width of the specimen container T in the image 100 is subjected to the following process by the CPU 81a. The processing area 101 is a predetermined area, which includes the vicinity of the bottom portion of the specimen container T and does not include the bar-code label BL1. For each X coordinate in the processing area 101, the CPU 81a accumulates B (blue) luminance values (hereinafter, referred to as "B value") of the pixels in a Y direction in the processing area 101. That is, an accumulation value (hereinafter, referred to as "B luminance accumulation value") of the B values of the pixels in a column of pixel groups at the left end included in the processing area 101 is calculated, and a B luminance accumulation value of a column of pixel groups on the right side thereof is calculated. This operation is repeated until reaching the right end of the processing area 101 while incrementing an X coordinate value.

In FIG. 24, a graph of the B luminance accumulation value obtained as described above in the processing area 101 is denoted by reference numeral 101a. The B luminance accumulation value related to the processing area 101 is high in a background and is low in the specimen container T. Accordingly, the CPU 81a differentiates the B luminance accumulation value in an X direction and detects a portion in which the B luminance accumulation value is sharply lowered and a portion in which the B luminance accumulation value sharply increases. In this manner, the width of the specimen container T is detected.

Figure 25:
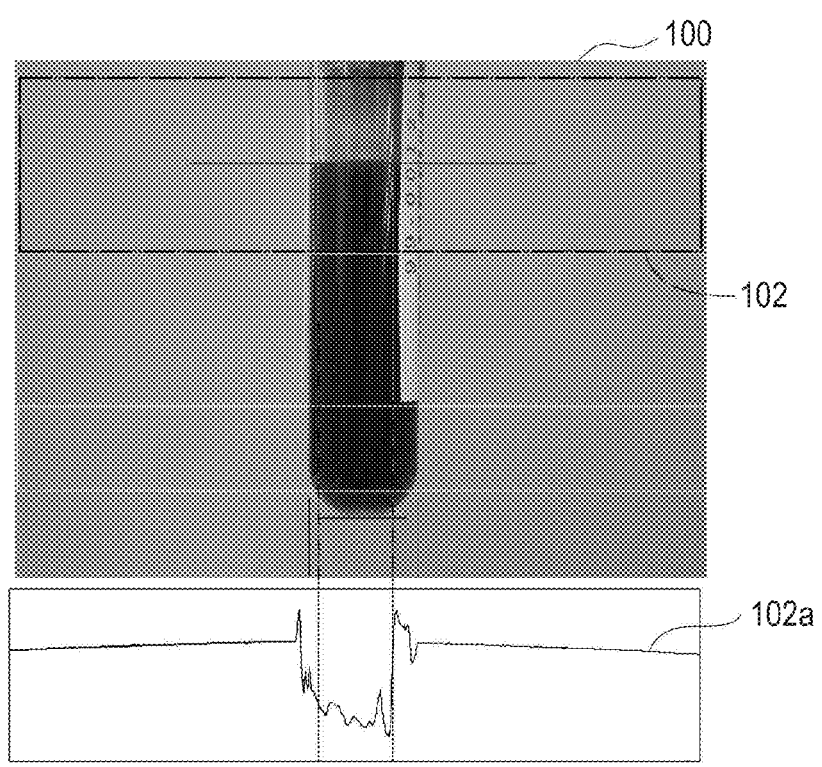
FIG. 25 is a schematic diagram for illustrating a process of detecting the positions of the right and left ends of a bar-code label in the image.

Next, the CPU 81a detects the positions of the right and left ends of the bar-code label BL1 in the image (Step S224). This process will be described in detail. FIG. 25 is a schematic diagram for illustrating the process of detecting the positions of the right and left ends of the bar-code label BL1 in the image. A processing area 102 for detecting the positions of the right and left ends of the bar-code label BL1 in the image 100 is subjected to the following process by the CPU 81a. The processing area 102 is a predetermined area, which is an upper portion in the image and includes the bar-code label. For each X coordinate value in the processing area 102, the CPU 81a calculates a B luminance accumulation value. In the drawing, a graph of the B luminance accumulation value in the processing area 102 is denoted by reference numeral 102a. As shown by the graph 102a, the B luminance accumulation value related to the bar-code label is higher than the B luminance accumulation values related to the background and the specimen container. Accordingly, the CPU 81a scans the B luminance accumulation value from the left to the right and detects a position, where the B luminance accumulation value is high and then is sharply lowered, as the position of the left end of the bar-code label. Then, the CPU scans the B luminance accumulation value from the right to the left and detects a position, where the B luminance accumulation value is high and then is sharply lowered, as the position of the right end of the bar-code label.

Figure 26:
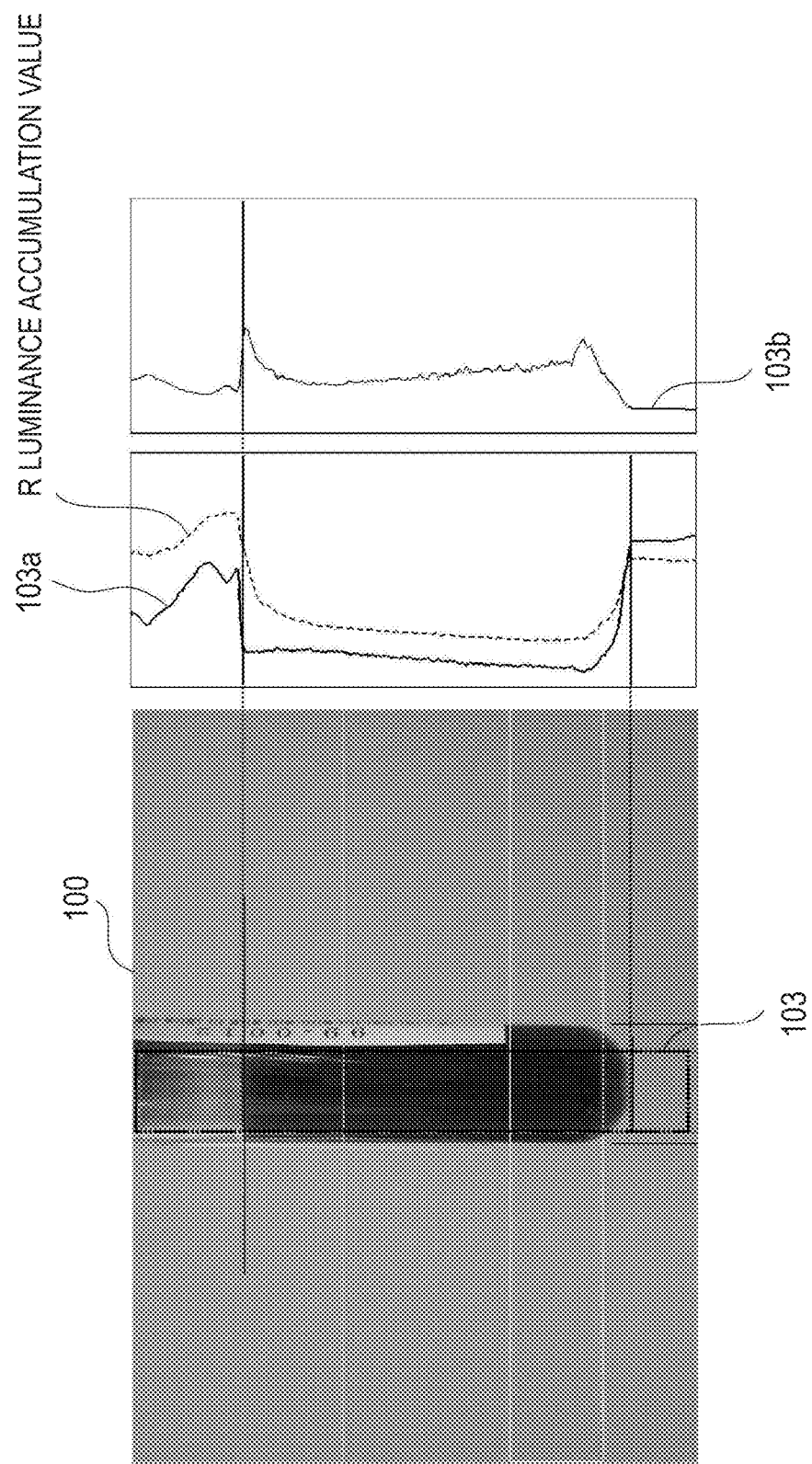
FIG. 26 is a schematic diagram for illustrating a process of detecting the position of the lower end of a specimen container in the image.

Next, the CPU 81a detects the position of the lower end of the specimen container in the image (Step S225). This process will be described in detail. FIG. 26 is a schematic diagram for illustrating the process of detecting the position of the lower end of the specimen container in the image. First, the CPU 81a determines a processing area 103 for detecting the position of the lower end of the specimen container and the position of a liquid surface of the blood specimen in the image 100. The processing area 103 is an area at the slightly inner side from an area surrounded by the positions of the right and left ends of the bar-code label detected in Step S224. This is because, the bar-code label does not exist in the area between the right and left ends of the bar-code label.

For each Y coordinate value in the processing area 103, the CPU 81a calculates a B luminance accumulation value by accumulating B values in an X direction, and calculates an R luminance accumulation value by accumulating R values. In addition, for each Y coordinate, the CPU 81a calculates a value (hereinafter, referred to as "R/B accumulation luminance ratio") which is obtained by dividing the R luminance accumulation value by the B luminance accumulation value. In the drawing, a graph of the B luminance accumulation value in the processing area 103 is denoted by reference numeral 103a and a graph of R/B in the processing area 103 is denoted by reference numeral 103b. As shown by the graph 103a, the B luminance accumulation value of the blood specimen in the specimen container is lower than the B luminance accumulation values of the background and a portion in which the blood specimen in the specimen container does not exist. Moreover, in the blood specimen, the R/B accumulation luminance ratio is higher than in the other portion. Accordingly, the CPU 81a differentiates the B luminance accumulation value in a Y direction, and detects as the position of the lower end of the specimen container a position where the B luminance accumulation value is sharply lowered in a direction toward the upper side from the lower end of the processing area 103.

Next, the CPU 81*a* determines whether a blood plasma portion and a blood cell portion are separated in the blood specimen (Step S226). In this process, it is determined that the blood plasma portion and the blood cell portion are separated, when the B luminance accumulation value and the R luminance accumulation value of the processing area 103 are scanned from the position of the lower end of the specimen container to the upper side and only the R luminance accumulation value is large.

When the blood plasma portion and the blood cell portion are separated (Yes in Step S226), the CPU 81*a* performs a first liquid surface position detecting process of detecting the position of the liquid surface of the blood specimen (Step S227). When the blood plasma portion and the blood cell portion are not separated (No in Step S226), the CPU performs a second liquid surface position detecting process of detecting the position of the liquid surface of the blood specimen (Step S228). In the first liquid surface position detecting process, a position, where the B luminance accumulation value becomes sharply larger in a direction toward the upper side from the blood specimen and the R/B accumulation luminance ratio is equal to or less than a predetermined value, is detected as the position of the liquid surface. In the second liquid surface position detecting process, a position, where the B luminance accumulation value becomes sharply larger in a direction toward the upper side from the blood specimen, is detected as the position of the liquid surface.

Next, the CPU 81*a* calculates the blood volume in the specimen container T (Step S229). In this process, the CPU 81*a* calculates a blood volume BV by the following expressions (1) and (2).

$$R=(k \cdot W-2T)/2 \quad (1)$$

$$BV=\pi R^2 \times (k \cdot H-R)+2\pi R^3/3 \quad (2)$$

R denotes a radius of an inner face of a specimen container, k denotes a coefficient determined by the scale of a captured image, W denotes the width of a specimen container, T denotes the thickness of a specimen container and H denotes the height (the difference between the position of a liquid surface and the position of the lower end of a specimen container) of a blood specimen. When calculating the blood volume BV, the CPU 81*a* calculates a blood volume NV necessary for the measurement from the measuring order corresponding to the specimen ID of the blood specimen as an object of image process (Step S2210) and determines whether the blood volume BV is equal to or more than the necessary blood volume NV, that is, whether the measurement of the specimen can be performed (Step S2211). In Step S2211, when it is determined that the blood volume BV is less than the necessary blood volume NV (No in Step S2211), the CPU 81*a* stores in the hard disk 51*d* specimen amount error information, indicating that an insufficient amount of the specimen for measurement is in the specimen container, which corresponds to the rack ID of the sample rack L and the holding position of the specimen container in the sample rack L (Step S2212), and completes the process. On the other hand, when the blood volume BV is equal to or more than the necessary blood volume NV (Yes in Step S2211), the CPU 81*a* completes the process.

Blood Coagulation Determining Process

The system control apparatus 8 takes an image captured by the camera 225*b* and performs image processing on the captured image so as to determine whether the blood specimen in the specimen container T is coagulated.

Figure 27:
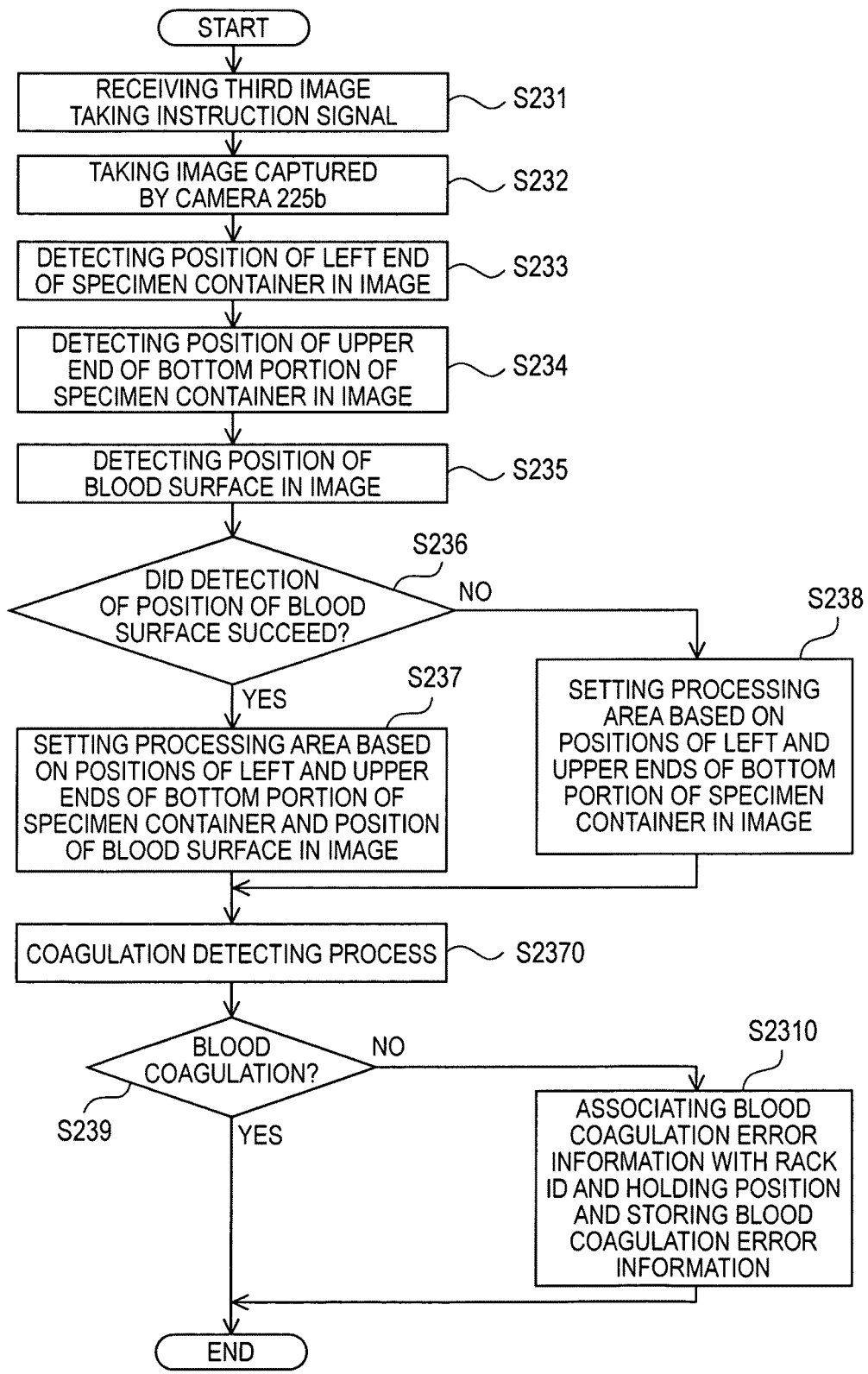
FIG. 27 is a flowchart showing the procedure of a blood coagulation determining process of the system control apparatus.

FIG. 27 is a flowchart showing the procedure of the blood coagulation determining process. As shown in FIG. 27, in the CPU 81*a*, a process of Step S232 is invoked when an event occurs in which the system control apparatus 8 receives the third image taking instruction signal transmitted from the specimen putting apparatus 2 (Step S231).

Figure 28:
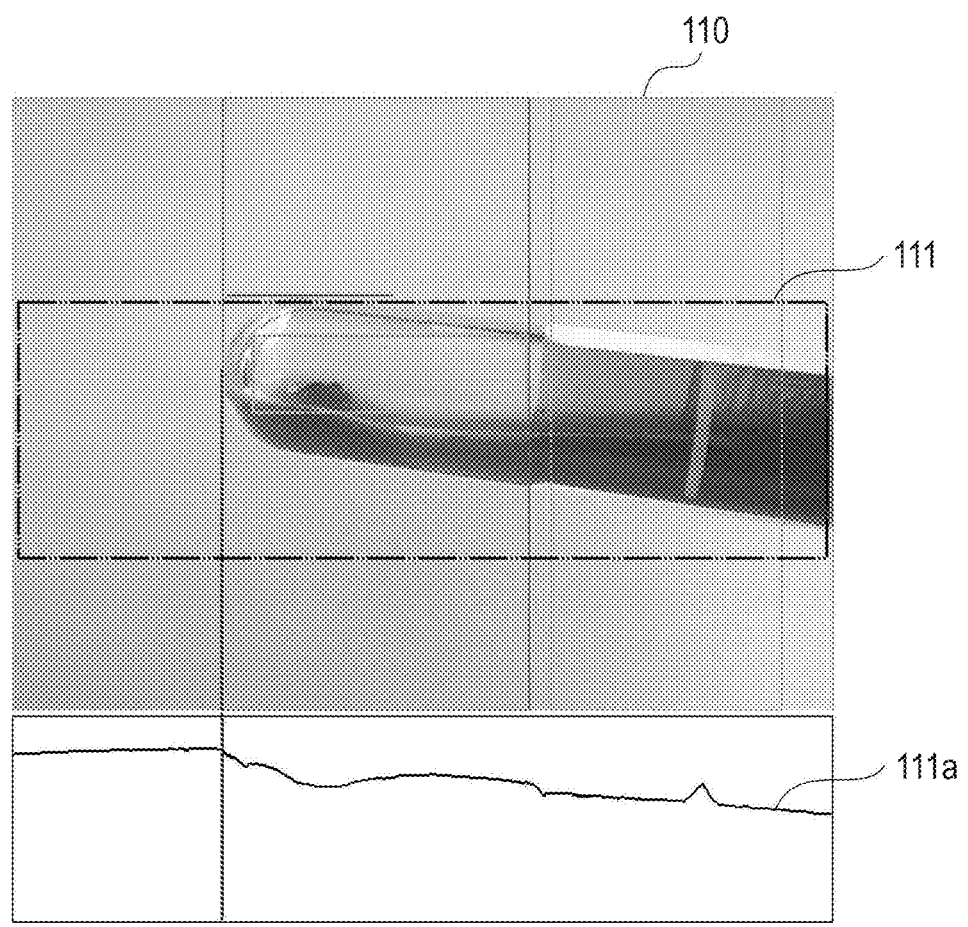
FIG. 28 is a schematic diagram for illustrating a process of detecting the position of the left end of a specimen container in an image.

In Step S232, the CPU 81*a* takes an image captured by the camera 225*b* at that time point (Step S232). Next, the CPU 81*a* detects the position of the left end of the specimen container T in the taken, captured image (Step S233). This process will be described in detail. FIG. 28 is a schematic diagram for illustrating the process of detecting the position of the left end of the specimen container T. An image 110 is a color image and has luminance information of RGB of respective pixels. A processing area 111 for obtaining the position of the left end of the specimen container T in the image 110 is subjected to the following process by the CPU 81*a*. The processing area 111 is a predetermined area, which includes the vicinity of the bottom portion of the specimen container T. For each X coordinate, the CPU 81*a* calculates a B luminance accumulation value in a Y direction in the processing area 111. In the drawing, a graph of the B luminance accumulation value in the processing area 111 is denoted by reference numeral 111*a*. As shown by the graph 111*a*, the B luminance accumulation value related to the specimen container is lower than the B luminance accumulation value related to a background. Accordingly, the CPU 81*a* differentiates the B luminance accumulation value in an X direction and detects a position, where the B luminance accumulation value scanned from the left to the right is lowered, as the position of the left end of the specimen container.

Figure 29:
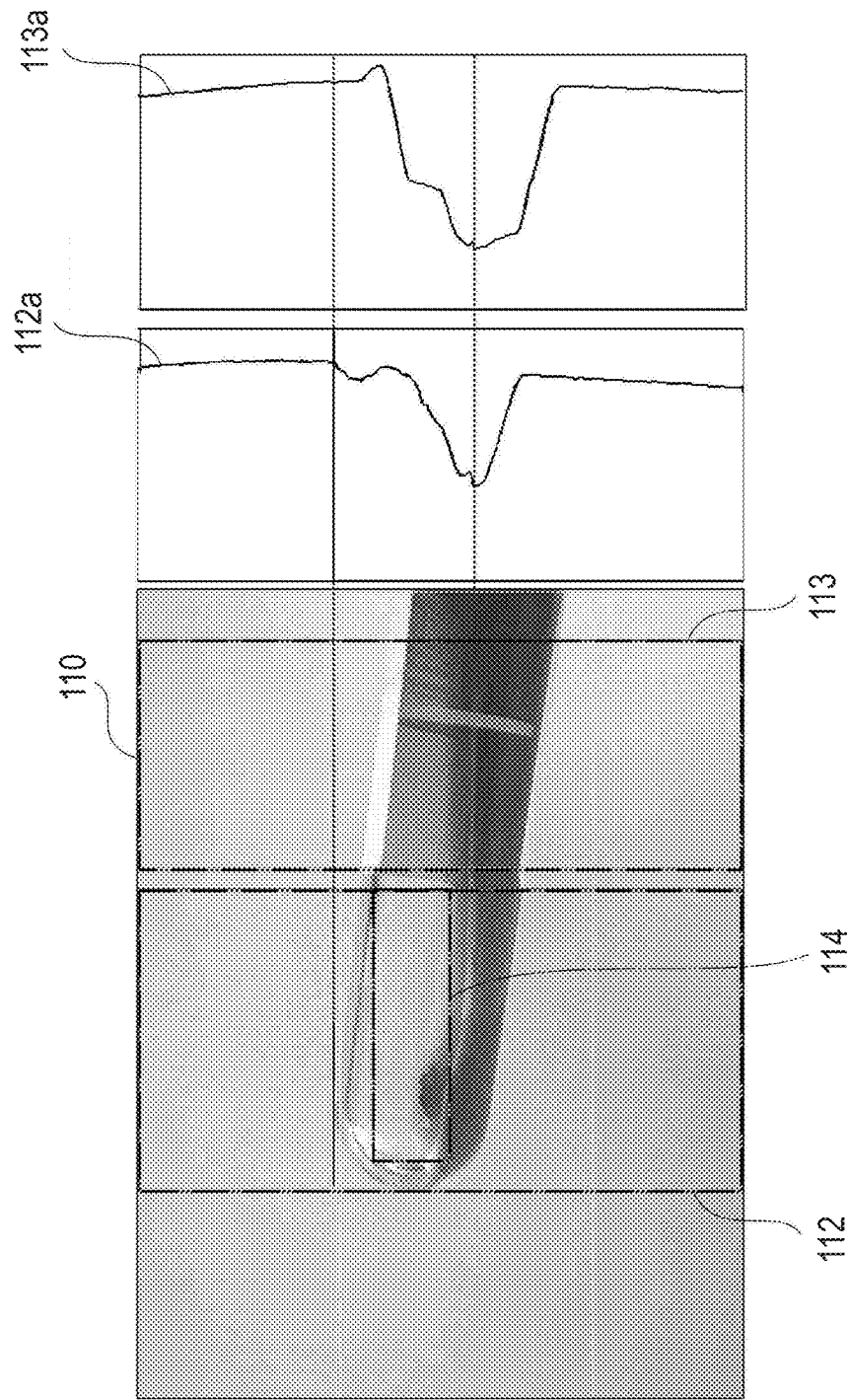
FIG. 29 is a schematic diagram for illustrating a process of detecting the position of the upper end of the bottom portion of the specimen container in the image.

Next, the CPU 81*a* detects the position of the upper end of the bottom portion of the specimen container (Step S234). This process will be described in detail. FIG. 29 is a schematic diagram for illustrating the process of detecting the position of the upper end of the bottom portion of the specimen container in the image. The CPU 81*a* determines a processing area 112 for detecting the position of the upper end of the bottom portion of the specimen container in the image 110. The processing area 112 is an area from the position of the left end of the specimen container detected in Step S233 to a position positioned on the right side thereof by a predetermined number of pixels. This is because, since the specimen container T is imaged in a state in which the bottom portion of the specimen container T is positioned higher than the cap section CP in the image, and it is required that the bottom portion of the specimen container is included in the processing area so that the bottom portion of the specimen container T becomes the upper end of the specimen container, the bottom portion of the specimen container T exists in an area on the right side of the position of the left end.

For each Y coordinate, the CPU 81*a* calculates a B luminance accumulation value in the X direction in the processing area 112. In the drawing, a graph of the B luminance accumulation value in the processing area 112 is denoted by reference numeral 112*a*. As shown by the graph 112*a*, the B luminance accumulation value related to the specimen container is lower than the B luminance accumulation value related to the background. Accordingly, the CPU 81*a* differentiates the B luminance accumulation value in the Y direction, and detects a position, where the B luminance accumulation value scanned from the upper side to the lower side is lowered, as the position of the upper end of the bottom portion of the specimen container.

Next, the CPU 81a detects the position of the liquid surface of the blood specimen (Step S235). This process will be described in detail. A processing area 113 (see FIG. 29 for reference) for detecting the position of the liquid surface of the blood specimen in the image 110 is subjected to the following process by the CPU 81a. The processing area 113 is a predetermined area, which is positioned at the right side in the image 110. When the blood specimen contains a clot formed by the aggregation of blood, the clot usually sinks to the bottom portion of the specimen container T due to the weight thereof. Accordingly, when the specimen container T is tilted to the second imaging position where the bottom portion of the specimen container T is positioned on the left side in a front view, the blood specimen in the specimen container T moves toward the cap section CP (right side) of the specimen container T and the blood specimen in the bottom portion of the specimen container T decreases. The clot, which has sunk to the bottom of the specimen container T, rides on the inner face of the bottom portion of the specimen container T and protrudes from the liquid surface of the shallow blood specimen. Thus, only the liquid blood exists in the area at the right side in the image 110. The processing area 113 is provided in this portion and thus the processing area 113 includes the liquid blood without the clot. Accordingly, the processing area 113 is suitable for the detection of the liquid surface which is the surface of liquid. For each Y coordinate value in the processing area 113, the CPU 81a calculates a B luminance accumulation value and an R luminance accumulation value. In the drawing, a graph of the B luminance accumulation value in the processing area 113 is denoted by reference numeral 113a. First, the CPU 81a sequentially checks an R/B accumulation luminance ratio toward the upper side from the lower end of the processing area 113 and determines whether the R/B accumulation luminance ratio is equal to or greater than a predetermined value. Herein, the R/B accumulation luminance ratio is large in the blood image. Accordingly, when the R/B accumulation luminance ratio is equal to or greater than the predetermined value, it can be judged that the blood is in the specimen container. When it can be judged that the blood is not in the specimen container, that is, when the R/B accumulation luminance ratio does not exceed the predetermined value in a direction of a Y axis of the entire processing area 113, it is regarded that the detection of the position of the liquid surface of the blood specimen has failed.

When it can be judged that blood exists, the CPU 81a checks the B luminance accumulation value toward the upper side from a position (position where the R/B accumulation luminance ratio is equal to or greater than the predetermined value) where it is considered that the blood exists so as to detect a position, where a differential value of the B luminance accumulation value is equal to or greater than a predetermined value and the R/B accumulation luminance ratio is equal to or less than a predetermined value, as the position of the blood surface. When there is no such position, it is regarded that the detection of the position of the blood surface has failed.

Next, the CPU 81a determines whether the detection of the position of the blood surface in Step S235 has succeeded (Step S236). When the detection of the position of the blood surface has succeeded (Yes in Step S236), a processing area for determining the presence or absence of blood coagulation is set based on the positions of the left and upper ends of the bottom portion of the specimen container and the position of the blood surface (Step S237). This processing area will be described with reference to FIG. 29. In the process of Step S237, a processing area 114 is set which is positioned on the right side of the left end of the bottom portion of the specimen container, on the lower side of the upper end of the image of the bottom portion of the specimen container, and on the upper side of the blood surface. As shown in FIG. 29, when the blood has coagulated, the clot protrudes upward from the liquid surface in some cases. In this case, the clot is in the processing area 114 positioned on the upper side of the liquid surface. The processing area 114 is subjected to image processing and thus the coagulation of the blood can be detected (S2370).

Figure 30:
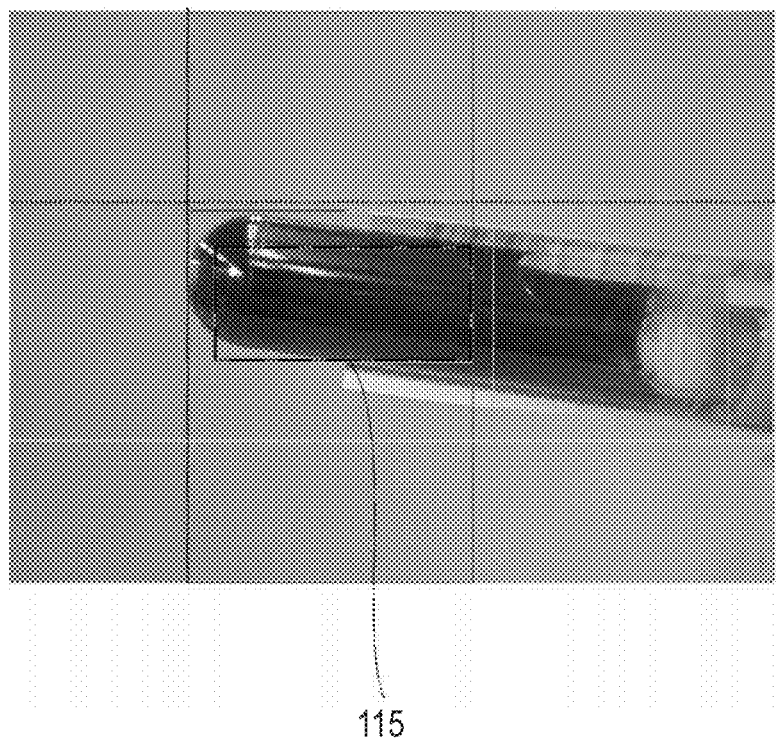
FIG. 30 is a schematic diagram for illustrating a processing area for determining blood coagulation when the detection of the position of a blood surface in the image fails.

On the other hand, when the detection of the position of the blood surface fails (No in Step S236), a processing area for determining the presence or absence of blood coagulation is set based on the positions of the left and upper ends of the bottom portion of the specimen container (Step S238). FIG. 30 is a schematic diagram for illustrating a processing area for determining blood coagulation when the detection of the position of the blood surface in the image fails. As shown in FIG. 30, in this case, a processing area 115 having a predetermined size is positioned on the right side of the left end of the bottom portion of the specimen container and on the lower side of the upper end of the bottom portion of the specimen container. When it can be judged that the blood exists and the position of the blood surface cannot be detected, the blood has viscosity due to coagulation and adheres to the inner face of the specimen container in some cases. In this case, the liquid surface cannot be confirmed even if the specimen container T is tilted, and the blood occupies a large portion of the processing area 115. The processing area 115 is subjected to image processing and thus the coagulation of the blood can be detected (S2370).

After setting the processing area for detecting blood coagulation, the CPU 81a determines the presence or absence of blood coagulation (Steps S239). This process will be described as follows. For each pixel included in the processing area 114 or 115, the CPU 81a calculates an R/B luminance ratio which is a ratio of an R value to a B value in a single pixel. In addition, the CPU 81a counts the number of pixels, each of which has the B value equal to or less than a predetermined value and the R/B luminance ratio equal to or less than a predetermined value, among all the pixels included in the processing area 114 or 115. When the number of pixels is equal to or greater than a predetermined value, it is determined that the blood is coagulated. When the number of pixels is less than the predetermined value, it is determined that the blood is not coagulated.

Figure 31A:
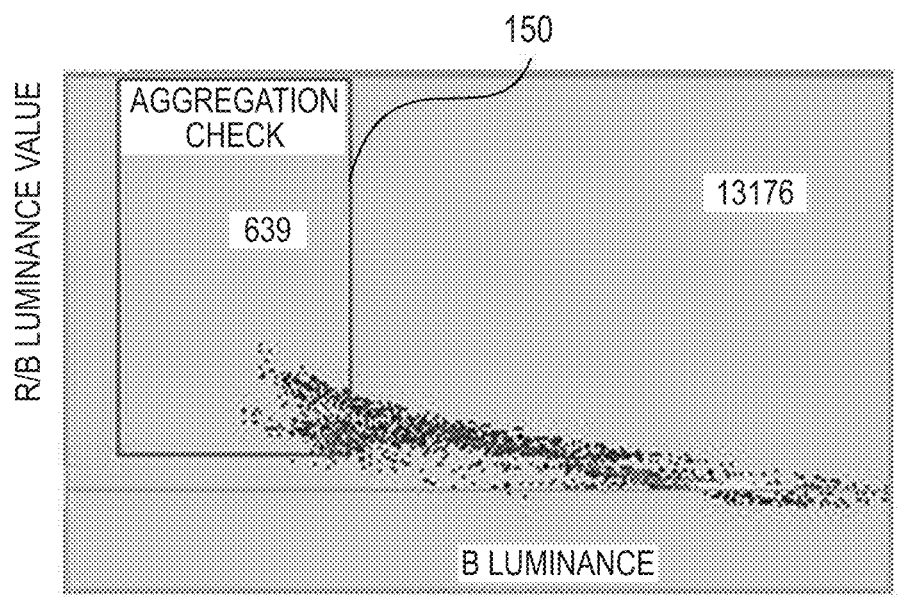
FIG. 31A is a scattergram showing a distribution state related to the B values and the R/B luminance ratios of pixels in the processing area in the image shown in FIG. 29.
Figure 31B:
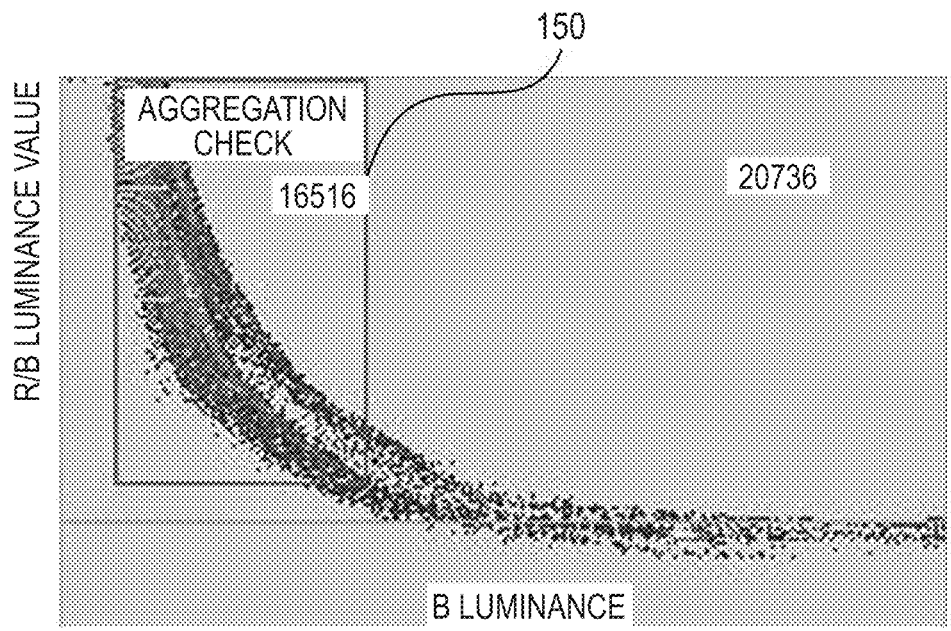
FIG. 31B is a scattergram showing a distribution state related to the B values and the R/B luminance ratios of pixels in the processing area in the image shown in FIG. 30.
Figure 31C:
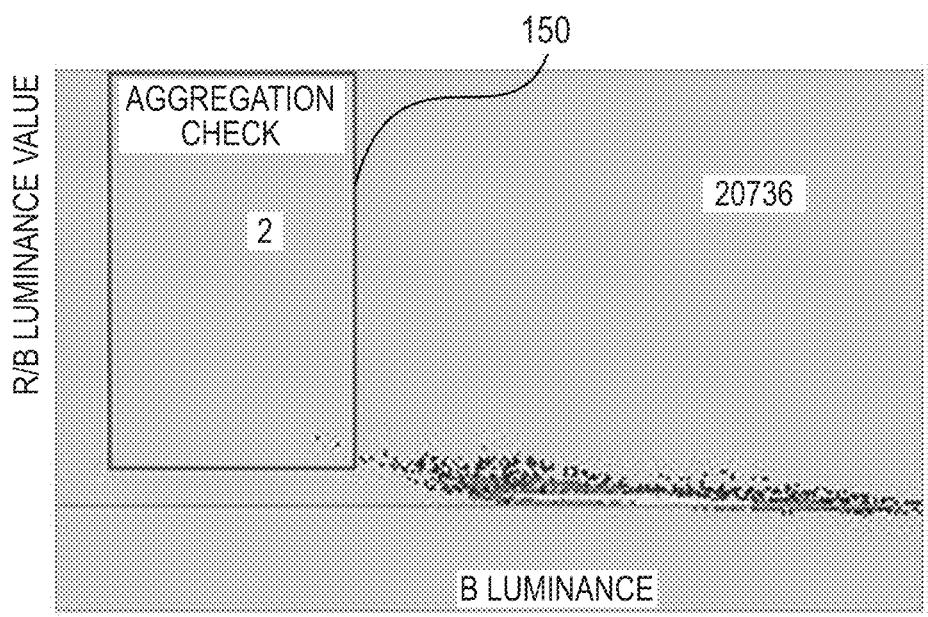
FIG. 31C is a scattergram showing a distribution state related to the B values and the R/B luminance ratios of pixels in the processing area for blood which is not coagulated.

FIG. 31A is a scattergram showing the distribution state related to the B values and the R/B luminance ratios of the pixels in the processing area 114 in the image shown in FIG. 29, FIG. 31B is a scattergram showing the distribution state related to the B values and the R/B luminance ratios of the pixels in the processing area 115 in the image shown in FIG. 29, and FIG. 31C is a scattergram showing the distribution state related to the B values and the R/B luminance ratios of the pixels in the processing area 114 for the blood which is not coagulated. In these drawings, a range satisfying the condition that the B value is equal to or less than a predetermined value and the R/B luminance ratio is equal to or less than a predetermined value is represented by a rectangular frame 150. As shown in FIG. 31A, when a clot protrudes on a blood surface, a large number of pixels (several hundreds of pixels or more when the image 100 has a size of 640×480 dots) in all the pixels included in the processing area 114 satisfy the above condition. In addition, as shown in FIG. 31B, when it can be judged that blood exists and a position of a blood surface cannot be detected, a very large number of pixels (10,000 pixels or more when the image 100 has a size of 640×480 dots) in all the pixels included in the processing area 115 satisfy the above condition. On the other hand, as shown in FIG. 31C, when a clot does not protrude on a blood surface, only a very small number of pixels (several pixels when the image 100 has a size of 640×480 dots) in all the pixels included in the processing area 114 does not satisfy the above condition. When a size of an image is 640×480 dots, the above threshold is set to about 100 and thus blood coagulation can be detected with a high degree of accuracy.

In Step S239, when it is determined that the blood is coagulated (No in Step S239), the CPU 81a stores in the hard disk 51d blood coagulation error information, indicating that the specimen accommodated in the specimen container is coagulated, which corresponds to the rack ID of the sample rack L and the holding position of the specimen container in the sample rack L (Step S2310), and completes the process. On the other hand, when it is determined that the blood is not coagulated (Yes in Step S239), the CPU 81a completes the process.

Sorting Instruction Process

The system control apparatus 8 instructs the specimen putting apparatus 2 to sort specimens into the specimens (sample rack L) to be transported to the following measuring unit 51 and the specimens (sample rack L) which are not to be transported to the measuring unit 51. Hereinafter, this process will be described in detail.

Figure 32:
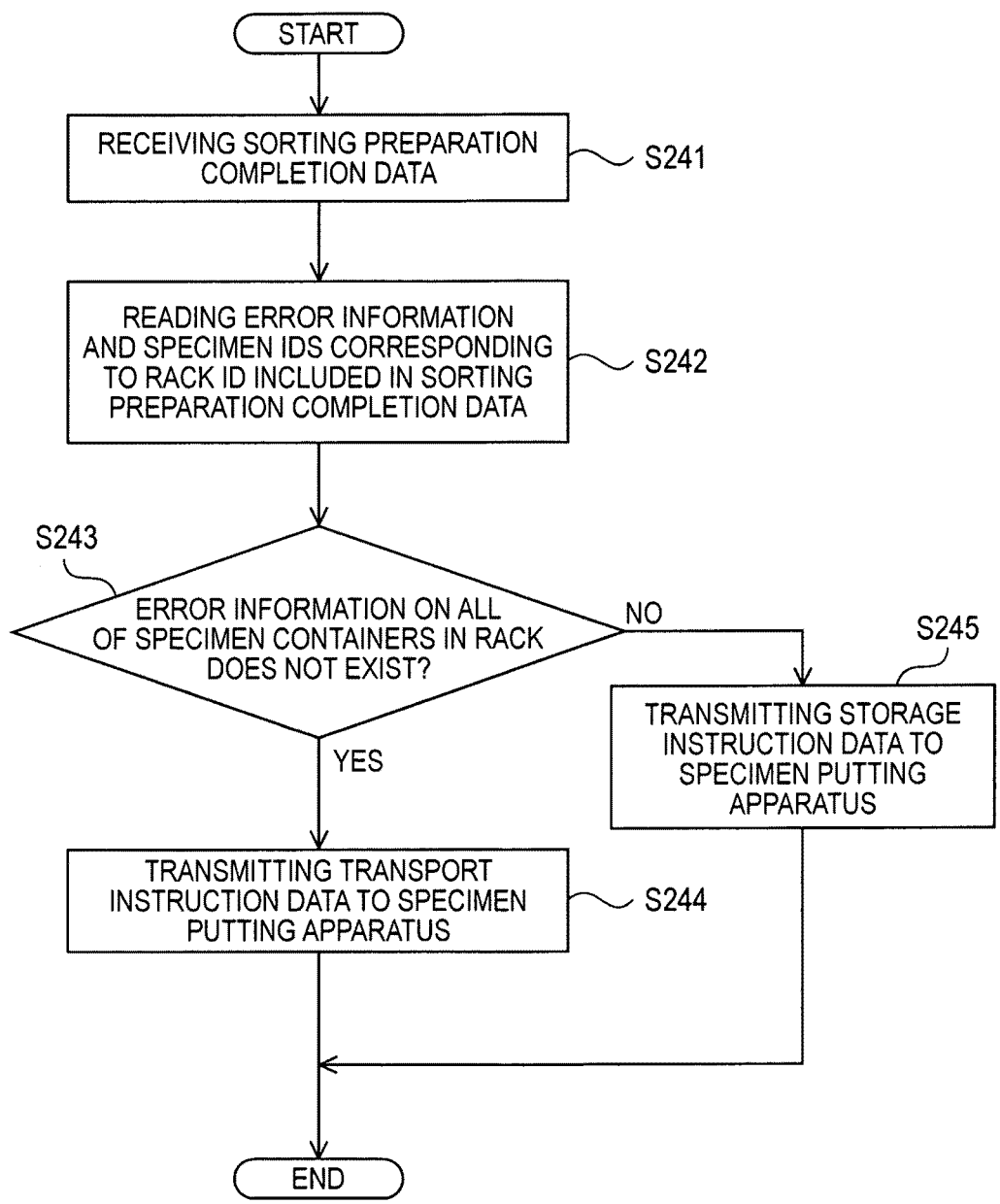
FIG. 32 is a flowchart showing the procedure of a sorting instruction process of the system control apparatus.

FIG. 32 is a flowchart showing the procedure of the sorting instruction process of the system control apparatus 8. As shown in FIG. 32, in the CPU 81a, a process of Step S242 is invoked when an event occurs in which the system control apparatus 8 receives the sorting preparation completion data transmitted from the specimen putting apparatus 2 (Step S241).

The sorting preparation completion data includes the rack ID. When receiving the sorting preparation completion data, the CPU 81a reads from the hard disk 51d the specimen IDs, the specimen bar-code reading error information (information indicating that the reading of the specimen ID has failed), the specimen container shape error information (information indicating that the shape of the specimen container is not suitable for measurement by the measuring unit 51), the measuring order obtaining error information (information indicating that the measuring order corresponding to the specimen ID does not exist), the specimen amount error information (information indicating that an insufficient amount of the specimen for measurement is accommodated in the specimen container), and the blood coagulation error information (information indicating that the specimen accommodated in the specimen container is coagulated), which correspond to the rack ID included in the sorting preparation completion data (Step S242). Then, the CPU 81a performs a determining operation on all the specimen containers for determining whether the error information exists (Step S243). When no error information exists on any of the specimen containers (Yes in Step S243), the CPU transmits the transport instruction data to the specimen putting apparatus 2 (Step S244) and completes the process. On the other hand, in Step S243, when the error information exists on at least one specimen container (No in Step S243), the CPU 81a transmits the storage instruction data D1 (see FIG. 15 for reference) including the above read error information to the specimen putting apparatus 2 (Step S245) and completes the process. In the sorting instruction process, even when the sorting preparation completion data does not include the rack ID (when the reading of the rack bar-code has failed), the storage instruction data including rack ID reading error information is transmitted.

Transport Instruction Process

The system control apparatus 8 receives the conveyance request data from the specimen putting apparatus 2, determines the transport destination of the sample rack L by using the specimen ID included in the conveyance request data and instructs the respective apparatuses to transport the sample rack to the determined transport destination. Hereinafter, this operation will be described in detail.

Figure 33A:
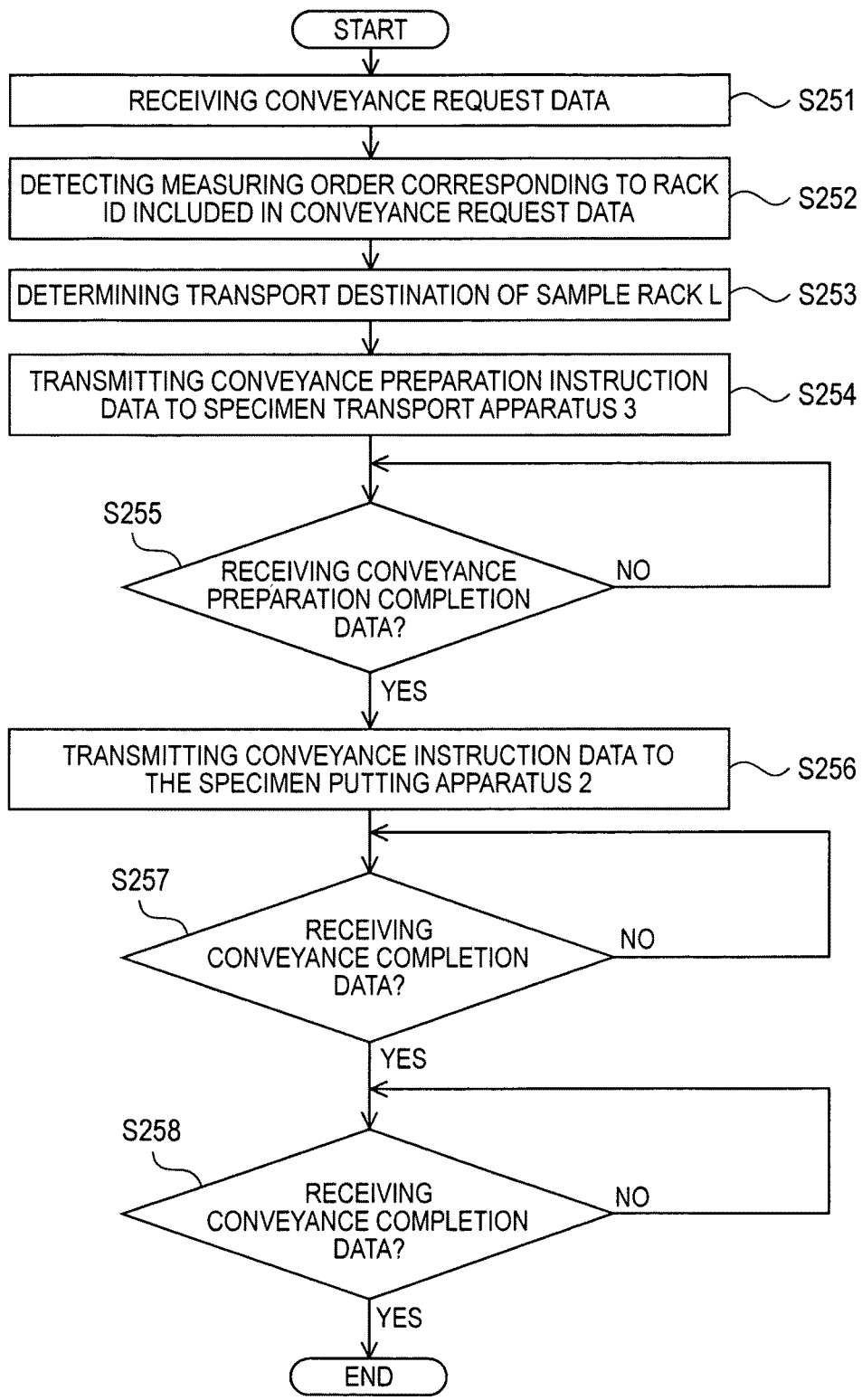
FIG. 33A is a flowchart showing the procedure of a first transport instruction process of the system control apparatus.

FIG. 33A is a flowchart showing the procedure of a first transport instruction process of the system control apparatus 8. In the first transport instruction process, the transport destination of the sample rack L is determined and a transport instruction is issued to the specimen transport apparatus 3 disposed in front of the measuring unit 51 on the uppermost-stream side in the transport direction. The conveyance request data transmitted from the specimen putting apparatus 2 is received by the communication interface 81g of the system control apparatus 8 (Step S251). In the CPU 81a, a process of Step S252 is invoked when an event occurs in which the conveyance request data is received.

In Step S252, the CPU 81a searches the measuring order stored in the hard disk 81d by using the rack ID, included in the received conveyance request data, as a key (Step S252). Next, the CPU 81a determines the transport destination of the sample rack L on the basis of the measuring items included in each received measuring order (Step S253). In this process, the measuring unit 51, capable of executing all the measuring items included in the measuring order, which is not performing a measurement or has the smallest number of planned measurements at that time point is determined as a measurement destination.

Next, on the basis of the determined transport destination, the CPU 81a transmits conveyance preparation instruction data of the sample rack L to the specimen transport apparatus 3 (that is, the rightmost specimen transport apparatus 3 in FIG. 1) adjacent to the specimen putting apparatus 2 (Step S254). The conveyance preparation instruction data includes data (hereinafter, referred to as "designated transport line instruction data") indicating the transport line (measuring line L1 or skip line L2) for transporting the sample rack L in the specimen transport apparatus 3 and the measuring orders of the specimens in the sample rack L. That is, when the transport destination of the sample rack L is the measuring unit 51 on the uppermost-stream side in the transport direction of the sample rack L, data indicating the measuring line L1 as the designated transport line instruction data is set in the conveyance preparation instruction data. On the other hand, when another measuring unit 51 is determined as the transport destination, data indicating the skip line L2 as the designated transport line instruction data is set in the conveyance preparation instruction data. The specimen transport apparatus 3 receiving the conveyance preparation instruction data performs an operation of preparing the transport mechanism indicated by the designated transport line instruction data included in the conveyance preparation instruction data (an operation to receive the sample rack L), and then transmits conveyance preparation completion data.

The CPU 81a stands by to receive the conveyance preparation completion data from the specimen transport apparatus 3 (No in Step S255). When the conveyance preparation completion data is transmitted from the specimen transport apparatus 3 and is received by the system control apparatus 8 (Yes in Step S255), the CPU 81a transmits conveyance instruction data of the sample rack L to the specimen putting apparatus 2 (Step S256). As described above, when receiving the conveyance instruction data, the specimen putting apparatus 2 conveys the sample rack L to the specimen transport apparatus 3 and transmits conveyance completion data. The CPU 81a stands by to receive the conveyance completion data from the specimen putting apparatus 2 (No in Step S257). When the conveyance completion data is transmitted from the specimen putting apparatus 2 and is received by the system control apparatus 8 (Yes in Step S257), the CPU 81a stands by to receive conveyance completion data from the specimen transport apparatus 3 (No in Step S258). When the conveyance completion data is transmitted from the specimen transport apparatus 3 and is received by the system control apparatus 8 (Yes in Step S258), the CPU 81a completes the process.

Figure 33B:
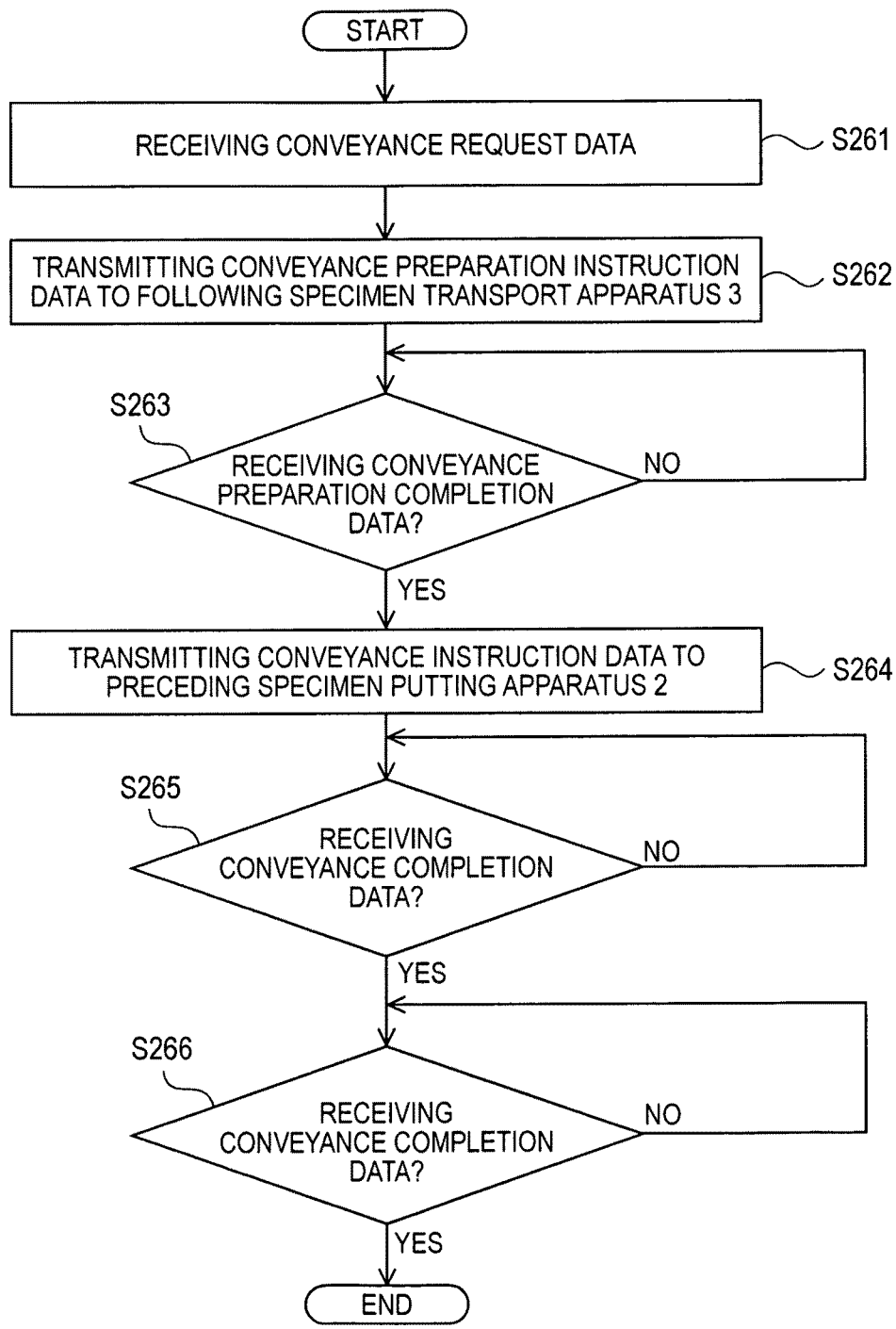
FIG. 33B is a flowchart showing the procedure of a second transport instruction process of the system control apparatus.

Next, a second transport instruction process of the system control apparatus 8 will be described. In the second transport instruction process, a transport instruction is issued to the specimen transport apparatus 3 disposed in front of the second or third measuring unit 51 in the transport direction of the sample rack L. FIG. 33B is a flowchart showing the procedure of the second transport instruction process. When the sample rack L transported by the specimen transport apparatus 3 reaches a conveyance position for conveying the sample rack L to the following specimen transport apparatus 3 (or specimen transport apparatus 301), conveyance request data including the rack ID of the sample rack L is transmitted from the specimen transport apparatus 3. The conveyance request data transmitted from the specimen transport apparatus 3 is received by the communication interface 81g of the system control apparatus 8 (Step S261). In the CPU 81a, a process of Step S262 is invoked when an event occurs in which the conveyance request data is received from the specimen transport apparatus 3.

In Step S262, the CPU 81a transmits conveyance preparation instruction data of the sample rack L to the specimen transport apparatus 3 following the present specimen transport apparatus 3 on the basis of the transport destination determined by the transport destination determining process (Step S262). Since the conveyance preparation instruction data is the same as the above-described conveyance preparation instruction data, a description thereof will be omitted.

Next, the CPU 81a stands by to receive conveyance preparation completion data from the specimen transport apparatus 3 (No in Step S263). When the conveyance preparation completion data is transmitted from the specimen transport apparatus 3 and is received by the system control apparatus 8 (Yes in Step S263), the CPU 81a transmits conveyance instruction data of the sample rack L to the preceding specimen transport apparatus 3 (conveyance side) (Step S264). When receiving the conveyance instruction data, the preceding specimen transport apparatus 3 conveys the sample rack L to the following specimen transport apparatus 3 and transmits conveyance completion data. The CPU 81a stands by to receive the conveyance completion data from the preceding specimen transport apparatus 3 (No in Step S265). When the conveyance completion data is transmitted from the preceding specimen transport apparatus 3 and is received by the system control apparatus 8 (Yes in Step S265), the CPU 81a stands by to receive conveyance completion data from the following specimen transport apparatus 3 (No in Step S266). When the conveyance completion data is transmitted from the following specimen transport apparatus 3 and is received by the system control apparatus 8 (Yes in Step S266), the CPU 81a completes the process.

<Operation of Control Section 32 of Specimen Transport Apparatus 3>

Figure 34A:
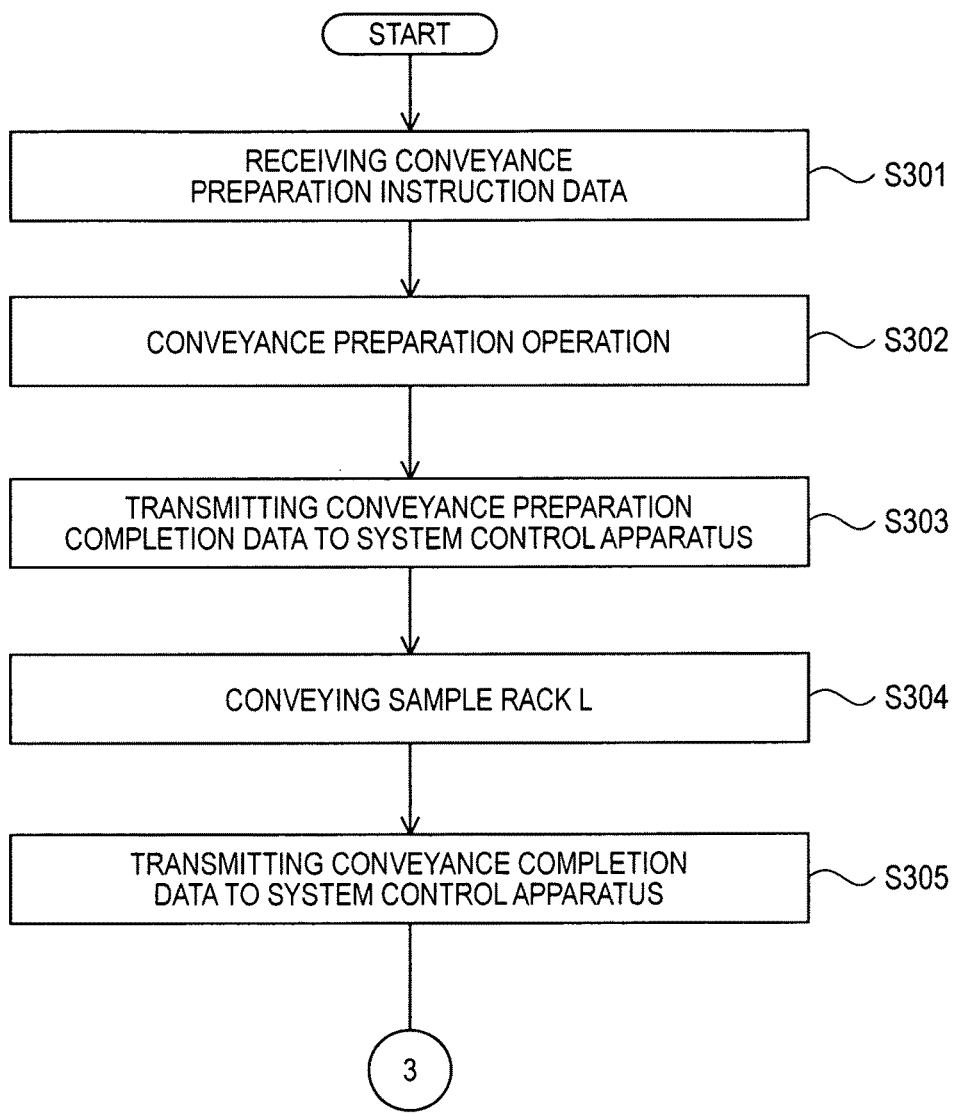
FIG. 34A is a flowchart (first half) showing the flow of a process of controlling a transport mechanism by a control section of the specimen transport apparatus.
Figure 34B:
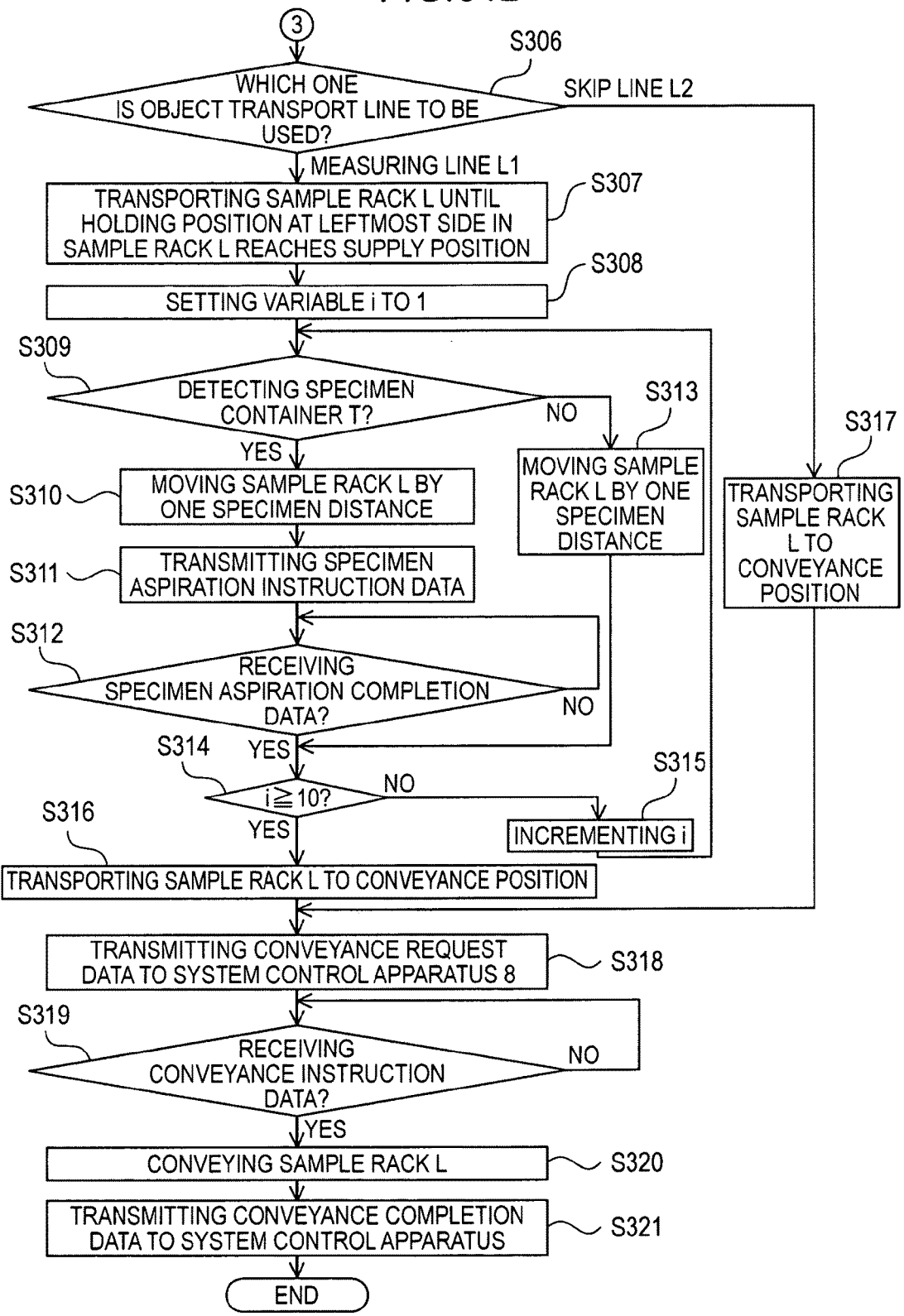
FIG. 34B is a flowchart (second half) showing the flow of the process of controlling the transport mechanism by the control section of the specimen transport apparatus.

Herein, an operation of the control section 32 of the specimen transport apparatus 3 disposed in front of the measuring unit 51 will be described. FIGS. 34A and 34B are flowcharts showing the flow of the process of controlling the transport mechanism 31 by the control section 32. The conveyance preparation instruction data transmitted from the system control apparatus 8 is received by the control section 32 (Step S301). A transport control program which is executed by the CPU of the control section 32 is an event-driven program, and in the control section 32, a process of Step S302 is invoked when an event occurs in which the conveyance preparation instruction data is received.

In Step S302, the control section 32 performs a conveyance preparation operation by driving the belt 321a of the transport mechanism 31 (Step S302). When the conveyance preparation is completed, the control section 32 transmits conveyance preparation completion data for notifying that the conveyance preparation is completed to the system control apparatus 8 (Step S303).

In response to the transmission of the conveyance preparation completion data, the sample rack L is conveyed from the preceding apparatus and is thus conveyed to the transport mechanism 31 (Step S304). When the conveyance of the sample rack L is completed, the control section 32 transmits conveyance completion data for notifying that the conveyance of the sample rack L is completed to the system control apparatus 8 (Step S305).

Next, the control section 32 determines whether designated transport line instruction data included in the conveyance preparation instruction data indicates the measuring line L1 or the skip line L2, that is, whether the object transport line to be used is the measuring line L1 or the skip line L2 (Step S306). In Step S306, when the designated transport line instruction data included in the conveyance preparation instruction data indicates the measuring line L1, that is, when the object transport line to be used is the measuring line L1 ("measuring line L1" in Step S306), the control section 32 controls the transport mechanism 31 so as to move the sample rack L until the holding section positioned at the leftmost side in FIG. 3 out of the holding sections for the specimen containers T in the sample rack L reaches the specimen container detection position (Step S307). Next, the control section 32 sets a variable i indicating the holding position of the specimen container T in the sample rack L to 1 (Step S308) and determines whether the specimen container sensor 38 detects the specimen container T at the specimen container detection position (Step S309). When the specimen container T is detected (Yes in Step S309), the control section moves the sample rack L to the left by one specimen distance (Step S310) and transmits specimen aspiration instruction data indicating a specimen aspiration instruction to the information processing unit 52 (Step S311). In this manner, the specimen container T detected by the specimen container sensor 38 is positioned at the specimen supply position 35c and the specimen is aspirated as described later. The control section 32 stands by to receive specimen aspiration completion data (No in Step S312). When receiving the specimen aspiration completion data (Yes in Step S312), the control section performs a process of Step S314.

On the other hand, when the specimen container T is not detected in Step S309 (No in Step S309), the control section 32 moves the sample rack L to the left by one specimen direction (Step S313) and performs the process of Step S314. In Step S314, the control section 32 determines whether i is equal to or greater than 10 (Step S314). When i is less than 10 (No in Step S314), the control section increments i by 1 (Step S315) and returns the process to Step S309.

In Step S314, when i is equal to or greater than 10 (Yes in Step S314), the control section 32 controls the transport mechanism 31 so as to bring the sample rack L to a conveyance position for conveying the sample rack L (Step S316). After that, the control section 32 performs a process of Step S318.

On the other hand, in Step S306, when the designated transport line instruction data included in the conveyance preparation instruction data indicates the skip line L2, that is, when the object transport line to be used is the skip line L2 ("skip line L2" in Step S306), the control section 32 controls the transport mechanism 31 so as to move the sample rack L on the skip line L2 to thereby bring the sample rack L to a conveyance position for conveying the sample rack L (Step S317). After that, the control section 32 performs the process of Step S318. In Step S318, the control section 32 transmits conveyance request data including the rack ID assigned to the sample rack L to the system control apparatus 8 (Step S318). Then, the control section 32 stands by to receive conveyance instruction data from the system control apparatus 8 (No in Step S319). When receiving the conveyance instruction data (Yes in Step S319), the control section drives the stepping motor 321b to convey the sample rack L to the adjacent specimen transport apparatus 3 (Step S320) and transmits conveyance completion data to the system control apparatus 8 (Step S321). In addition, the control section 32 completes the process.

<Operation of Blood Cell Analyzing Apparatus 5>

Next, an operation of the blood cell analyzing apparatus 5 will be described. The information processing unit 52 controls the operation of the measuring units 51, 51 and 51 so as to perform the specimen measurement and analyzes measuring data obtained by the measurement.

Figure 35A:
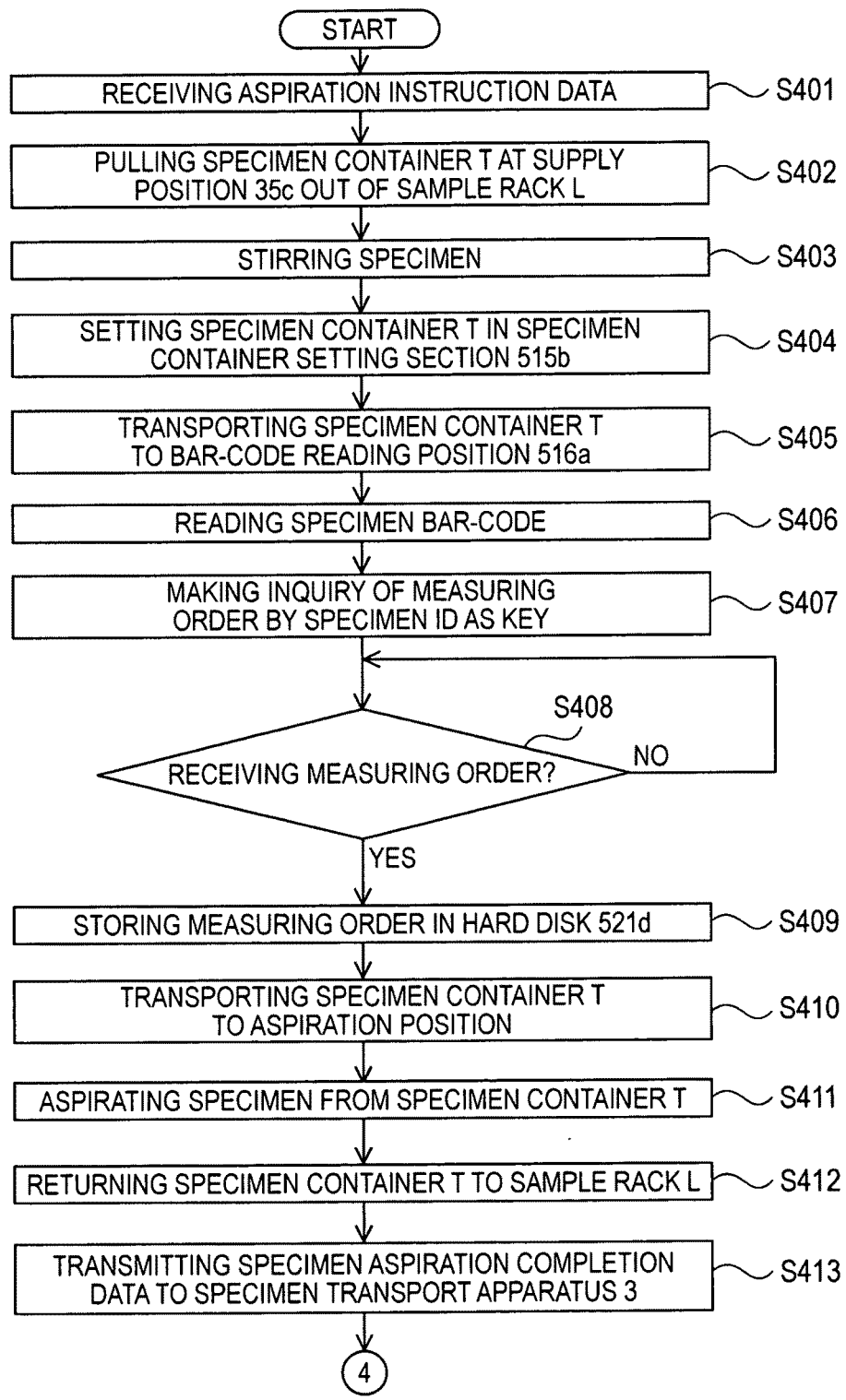
FIG. 35A is a flowchart (first half) showing the procedure of a specimen analyzing operation of the blood cell analyzing apparatus according to the embodiment.
Figure 35B:
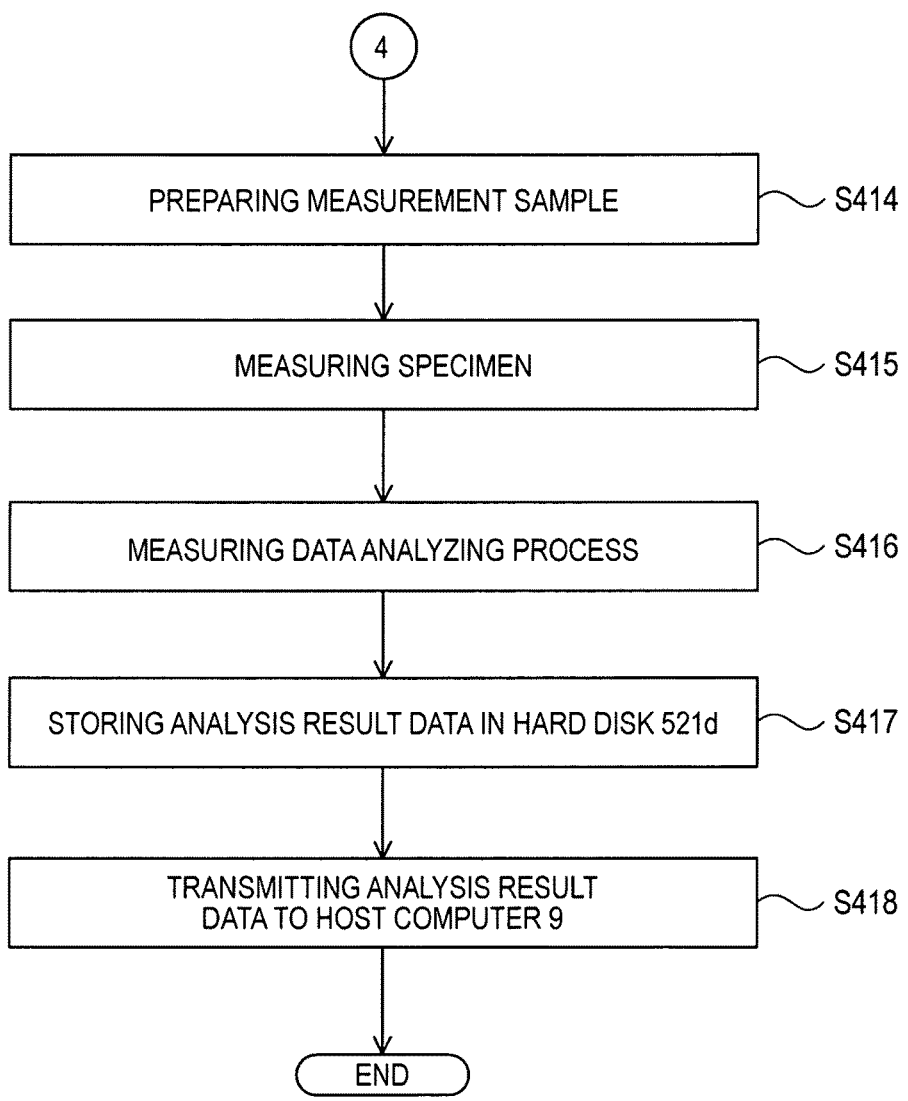
FIG. 35B is a flowchart (second half) showing the procedure of the specimen analyzing operation of the blood cell analyzing apparatus according to the embodiment.

FIGS. 35A and 35B are flowcharts showing the procedure of the specimen analyzing operation of the blood cell analyzing apparatus 5 according to this embodiment. First, the information processing unit 52 receives aspiration instruction data transmitted from the control section 32 of the specimen transport apparatus 3 (Step S401). In the CPU 521a, a process of Step S402 is invoked when an event occurs in which the aspiration instruction data is received. The aspiration instruction data includes a measuring unit ID of the measuring unit 51 which is the object to be operated.

In Step S402, the CPU 521a controls the specimen container transport section 515 so as to pull the specimen container T at the supply position 35c out of the sample rack L (Step S402) and controls the hand section 515a so as to oscillate the specimen container T to thereby stir the specimen in the specimen container (Step S403). Next, the CPU 521a controls the hand section 515a so as to set the specimen container T in the specimen container setting section 515b (Step S404) and further controls the specimen container transport section 515 so as to transport the specimen container T to the bar-code reading position 516a (Step S405). Next, the CPU 521a reads the specimen bar-code of the specimen container T by the bar-code reading section 516 to obtain the specimen ID (Step S406). Further, the CPU 521a transmits order request data including the specimen ID to the host computer 9 via the communication interface 521g (Step S407) so as to make an inquiry of measuring order. After that, the CPU 521a stands by to receive a measuring order (No in Step S408). When the measuring order transmitted from the host computer 9 is received by the communication interface 521g of the information processing unit 52 (Yes in Step S408), the received measuring order is stored in the hard disk 521d (Step S409).

Next, the CPU 521a controls the specimen container transport section 515 so as to transport the specimen container T to the aspiration position (Step S410) and controls the specimen aspirating section 511 so as to aspirate from the specimen container T a sufficient amount of the specimen for the measuring items included in the stored measuring order (Step S411). After the aspiration of the specimen is completed, the CPU 521a controls the specimen container transport section 515 so as to return the specimen container T to the sample rack L (Step S412) and transmits specimen aspiration completion data to the specimen transport apparatus 3 transporting the sample rack L (Step S413). In this manner, the sample rack L is transported by the rack transport section 35 as described above.

Moreover, the CPU 521a controls the sample preparing section 512 so as to prepare a measurement sample in accordance with the measuring items (Step S414) and supplies the measurement sample to the detecting section 513 so as to perform the specimen measurement by the detecting section 513 (Step S415). In this manner, the CPU 521a obtains measuring data output from the detecting section 513. The CPU 521a performs a process to analyze the measuring data (Step S416), classifies the blood cells included in the specimen and counts the number of blood cells for each type so as to create a scattergram in which the classified blood cells are color-coded for each type. The analysis result data generated by the measuring data analyzing process is stored together with the patient information and the like included in the measuring order in the hard disk 521d (Step S417) and is transmitted to the host computer 9 (Step S418). The host computer 9 integrates the analysis result data and the above-described measuring order and stores the result thereof in the hard disk. After the process of Step S418, the CPU 521a completes the process.

<Operation of Specimen Transport Apparatus 301>

The sample rack L delivered from the specimen transport apparatus 3 positioned on the downmost-stream side in the transport direction is introduced into the rack slider 303. Although a detailed description is omitted, the rack slider 303 receives an instruction from the system control apparatus 8 and delivers the sample rack L to the measuring line 302a or the skip line 302b of the conveyor 302. When the sample rack L is conveyed to the measuring line 302a, the control section of the conveyor 302 operates the measuring line 302a so as to transport the sample rack L so that the specimen container T as a smear preparing object is positioned at a supply position for supplying the specimen to the smear preparing apparatus 6. After the supply of the specimen to the smear preparing apparatus 6 is completed, the measuring line 302a is further driven so as to convey the sample rack L to the specimen accommodating apparatus 4. In addition, when the sample rack L is conveyed to the skip line 302b, the control section of the conveyor 302 operates the skip line 302b so as to transport the sample rack L on the skip line 302b to thereby convey the sample rack to the specimen accommodating apparatus 4.

<Operation of Specimen Accommodating Apparatus 4>

The sample rack L delivered from the specimen transport apparatus 301 is introduced into the specimen accommodating apparatus 4. The specimen accommodating apparatus 4 transports the sample rack L on the rack placing section and accommodates the sample rack.

By employing the above configuration, it is possible to sort the sample racks into the sample racks L accommodating the specimens with no abnormality which are to be provided for the measurement and the sample racks L accommodating the specimens which are not to be provided for the measurement, such as the specimens which are coagulated, the specimens with an insufficient amount for the measurement and the specimens which are not suitable because the shapes of the specimen containers are not suitable for the system. Accordingly, it is possible to prevent the operation stoppage of the specimen processing system 1 due to the transport of the specimens which are not to be provided for the measurement to the measuring unit 51.

In the past, the specimen which is not to be provided for the measurement as described above was supplied to the measuring unit and thus there was a specimen aspiration error in the measuring unit, so the operation of the specimen processing system 1 stopped. Accordingly, the operator was required to constantly monitor the specimen processing system against the possible of such an abnormality. On the other hand, in the specimen processing system 1 according to this embodiment, since the sample rack L accommodating the specimen which is not to be provided for the measurement is accommodated in the specimen container collect section 221, the operator is not required to constantly monitor the specimen putting apparatus 2. After the sample rack L in which the abnormality is detected is accommodated in the specimen container collect section 221, an appropriate action can be taken by taking out the sample rack L from the specimen container collect section 221 and this improves convenience for the operator.

In addition, when the abnormality is detected in the plural sample racks L, these sample racks L are stored in the specimen container collect section 221, so the operator is not required to take action in regard to each sample rack L every time an abnormality is generated, and can collectively process the plural sample racks L stored in the specimen container collect section 221. Accordingly, this improves convenience for the operator.

Furthermore, since the liquid crystal display section 227 performs a display operation so as to specify which specimen in the sample rack L is the specimen with an error (that is, which is judged not to be provided for the measurement), the operator can specify which specimen is the specimen requiring action with a simple confirmation of the detailed information screen displayed on the liquid crystal display section 227.

Since the detailed information screen performs a display operation so as to specify which kind of error is generated, the operator can specify which kind of abnormality was generated with a simple confirmation of the detailed information screen displayed on the liquid crystal display section 227. Accordingly, it is possible to easily and rapidly judge which kind of action is required.

Moreover, the rack re-putting section 231 is provided in the specimen feeding unit 23 following the specimen checking unit 22. Accordingly, when although the sample rack is determined not to be provided for the measurement for the moment, all the specimens accommodated in the sample rack L are made measurable with an operation of a user (for example, the replacement of specimen container and the removal of clot), the operator can put the sample rack L into the rack re-putting section 231 of the specimen feeding unit 23, not into the specimen setting section 21. Accordingly, it is not necessary to re-read the specimen IDs of the specimens in the sample rack L by the specimen bar-code reader 21*b* and thus this improves the system process efficiency.

In addition, by employing the above configuration, when a failure occurs in the reading of the specimen ID by the specimen bar-code reader 21*b*, the sample rack L accommodating the specimen container T is accommodated in the rack placing section 221. When re-putting the sample rack L into the specimen processing system 1, the operator takes out the sample rack L from the rack placing section 221, re-reads the specimen ID of the specimen in which the failure occurs in the reading of the specimen ID by using the handy bar-code reader 222*c*, and returns the specimen container T to its original position in the sample rack L. In this manner, it is not necessary to re-read other specimen IDs which have been normally read and it is possible to easily and rapidly re-put the sample rack L into the specimen processing system 1.

Since the specimen feeding unit 23 having the rack re-putting section 231 and capable of accommodating the plural sample racks L is provided to follow the specimen checking unit 22 sorting the sample racks into the sample racks L accommodating the specimen containers T in which a failure has occurred in the reading of the specimen ID and the sample racks L accommodating the specimen containers T in which no failure has occurred in the reading of the specimen ID, the operator places in the rack re-putting section 231 the sample rack L accommodating the specimen container of which the specimen ID is re-read by the handy bar-code reader 222*c* as described above. In this manner, it is possible to re-put the sample rack L into the specimen processing system 1. Accordingly, it is not necessary to re-read the specimen IDs of the specimens in the sample rack L by the specimen bar-code reader 21*b* and thus this improves the system process efficiency.

Since the bar-code reader 222*c* is a handy type, the operator can easily manually read the specimen bar-code.

Further, when a failure occurs in the reading of the specimen ID, the detailed information screen of the liquid crystal display section 227 displays bar-code reading error information associated with the holding position in the sample rack L. Accordingly, the operator can easily grasp which specimen has a bar-code reading failure with a simple confirmation of the detailed information screen. Thus, the operator can easily specify the position of the specimen container in which the failure has occurred in the reading of the bar-code in the sample rack L, take out the specimen container from the sample rack L, and easily re-read the specimen ID by the handy bar-code reader.

The operator takes out an arbitrary sample rack L from the plural sample racks L accommodated on the rack placing section 221 and reads the rack bar-code of the sample rack L by the handy bar-code reader 222*c*. In this manner, the detailed information screen relating to the sample rack L can be displayed. Moreover, the operator selects an arbitrary rack ID from the plural rack IDs displayed in the stored rack list screen and selects the display switching button B1. In this manner, the detailed information screen relating to the selected rack ID can be easily displayed.

When the operator re-reads the specimen bar-code of the specimen in which a failure has occurred in the reading of the bar-code by using the handy bar-code reader 222*c*, the specimen bar-code reading error information on the specimen is deleted from the stored rack information D2, so the error information on the specimen in which the bar-code reading error has been solved is also deleted in the liquid crystal display section 227. Accordingly, it becomes obvious which specimen is a specimen in which the error has been solved and which specimen is a specimen in which the error has not yet been solved.

(Other Embodiments)

In the above-described embodiments, the specimen processing system has been described which includes the plural measuring units 51, 51 and 51 and transports specimens to respective measuring units. However, the invention is not limited to this. A specimen analyzing apparatus may be used which includes one measuring unit and a specimen transport unit and transports specimens to the measuring unit by the specimen transport unit. In this case, the specimen transport unit may include a putting area in which the plural sample racks accommodating the before-analysis specimens can be placed and a storing area in which the plural sample racks accommodating the after-analysis specimens can be placed, may detect the shape of the specimen container accommodated in the sample rack L in the putting area and the amount and/or the coagulation of the specimen accommodated in the specimen container, and may transport the sample rack accommodating the specimen in which the abnormality is detected to a retreat area, provided separately from the putting area and the storing area, in which the plural sample racks can be placed.

Further, when the specimen analyzing apparatus is used which includes one measuring unit and the specimen transport unit and transports specimens to the measuring unit by the specimen transport unit, the specimen transport unit may include a putting area in which the plural sample racks accommodating the before-analysis specimens can be placed and a storing area in which the plural sample racks accommodating the after-analysis specimens can be placed, may read the specimen IDs of the specimen containers accommodated in the sample racks L in the putting area by a bar-code reader, and may transport the sample rack accommodating the specimen container in which a failure has occurred in the reading of the specimen ID to a retreat area, provided separately from the putting area and the storing area, in which the plural sample racks can be placed.

In the above-described embodiments, the configuration has been described in which the shape of a specimen container, the amount of the specimen accommodated in a specimen container and the coagulation of a specimen are each detected. However, the invention is not limited to this. A configuration may be employed in which one or two of the shape of a specimen container, the amount of the specimen accommodated in a specimen container and the coagulation of a specimen can be detected.

In the above-described embodiments, the configuration has been described in which an image obtained by imaging the specimen container in a vertical state is processed and the width of the specimen container, a position of the bottom of the specimen container and a position (height) of a blood surface are detected so as to detect a blood volume based on the detection results. However, the invention is not limited to this. A configuration also may be employed in which an image obtained by imaging the specimen container T in a vertical state is binarized to obtain an area of a blood portion specified by the binarized image and thus a blood volume is obtained from the area by, for example, a look-up table or a calculation formula.

In the above-described embodiments, the configuration has been described in which the blood coagulation is determined by performing image processing on the processing area 114 positioned higher than the position of the blood surface in the image. However, the invention is not limited to this. A configuration may be employed in which an image obtained by imaging a tilted specimen container is binarized to obtain the binarized image having a blood portion and the other portion as different values, a border between an area of "0" and an area of "1" of the binarized image is detected, and on the basis of the position (height of the liquid surface) of a linear portion of the border, it is determined whether a portion protruding upward from the linear portion, that is, a clot exists in the border.

In the above-described embodiments, the configuration has been described in which the number of pixels of which the B value is equal to or less than a predetermined value and the R/B luminance ratio is equal to or less than a predetermined value is counted out of all the pixels included in the processing area 114 positioned higher than the liquid surface of a specimen to determine the blood is coagulated when the number of pixels is equal to or greater than a predetermined value and to determine the blood is not coagulated when the number of pixels are less than the predetermined value. However, the invention is not limited to this. A configuration may be employed in which the processing area 114 in the image is binarized so that a blood portion is set to, for example "0" and the other portion is set to, for example "1", and an area of the blood portion obtained in this manner is compared with a predetermined reference value to determine that the blood is coagulated when the area is equal to or greater than a reference value and determine that the blood is not coagulated when the area is less than the reference value.

In the above-described embodiments, the configuration has been described in which an image process is performed using a value related to the B value of the R/B luminance ratio, the R/B accumulation luminance ratio, the B luminance accumulation value and the B value to perform the detection of a blood volume and the determination of blood coagulation. However, the invention is not limited to this. A G value may be used in place of the B value.

In the above-described embodiments, the configuration has been described in which the specimen processing system 1 includes the blood cell analyzing apparatus 5 classifying blood cells included in a specimen and counting the number of blood cells for each type of blood cell. However, the invention is not limited to this. A configuration may be employed in which the specimen processing system includes a specimen analyzing apparatus other than the blood cell analyzing apparatus, such as an immunity analyzing apparatus, a blood coagulation measuring apparatus, a biochemical analyzing apparatus and an urine analyzing apparatus and transports blood specimens or urine specimens to a measuring unit of the specimen analyzing apparatus.

In the above-described embodiments, the configuration has been described in which by executing the specimen container shape detecting process, the blood volume detecting process and the blood coagulation determining process of the computer program 84*a* with the computer, the computer serving as the system control apparatus 8 detects the shape of a specimen container and the blood volume in a specimen container and determines the coagulation of the blood specimen in a specimen container. However, the invention is not limited to this. A configuration may be employed in which the specimen container shape detecting process, the blood volume detecting process and the blood coagulation determining process are performed using a dedicated hardware such as FPGA, ASIC or the like capable of executing the same process as the computer program.

In the above-described embodiments, the configuration has been described in which the specimen checking unit 22 includes the handy bar-code reader 222*c*. However, the invention is not limited to this. A configuration may be employed in which the specimen checking unit 22 is provided with a bar-code reader for automatically reading a specimen bar-code from the specimen container T in the sample rack L accommodated on the rack placing section 221 of the specimen checking unit 22. Even in this case, it is not necessary to re-read the specimen bar-code of the specimen container in which a failure has occurred in the reading of the specimen bar-code by the bar-code reader 21*b* of the specimen setting section 21. Accordingly, it is possible to read the specimen bar-code of an unprocessed specimen put into the specimen setting section 21 by the bar-code reader 21*b* without standing by to re-read the specimen bar-code of the specimen in which a failure has occurred in the reading of the specimen bar-code and a specimen processing rate can thus be improved. It is obvious that such an effect is also achieved in the configuration of the embodiments in which the specimen checking unit 22 includes the handy bar-code reader 222c.

In the above-described embodiment, the configuration, in which all the processes of the computer program 84a are performed by the single computer 8a, has been described. However, the invention is not limited to this. A distribution system for distributing the same process as the above-described computer program 84a to plural apparatuses (computers) and performing the process also may be employed.

What is claimed is:

1. A specimen processing system comprising:
a specimen setting section;
a specimen re-putting section connected to the specimen setting section by a feed port, both configured for setting a specimen container thereon;
a transporting system that transports a specimen container set in the specimen setting section;
an imaging unit that obtains shape information on a specimen container transported by the transporting system by imaging the transported specimen container;
a specimen measuring section that measures a specimen accommodated in a specimen container imaged by the imaging unit and transported to the specimen measuring section by the transporting system;
an accommodating section configured for accommodating a specimen container accommodating a specimen measured by the specimen measuring section;
a collect section configured for collecting the specimen container that is imaged by the imaging unit and is not measured by the specimen measuring section, wherein the collect section is arranged nearer the specimen setting section than the specimen measuring section; and
a control system configured to determine whether or not the specimen container imaged by the imaging unit is to be supplied to the specimen measuring section for analysis based on the obtained shape information, to transport an accepted specimen container that is determined to be supplied to the specimen measuring section to the specimen measuring section, and to transport rejected specimen containers that are determined not to be supplied to the specimen measuring section to the collect section or the re-putting section;
a display;
a storing section configured for storing the information relating to the rejected specimen container, wherein
the control system is configured to control the display to display information relating to the rejected specimen container and an icon that receives a delete instruction for deleting information relating to the rejected specimen container, where the delete instruction is received by an operator to delete the information from the display and the storing section when the delete instruction is received by selecting the icon, and to transport operator-designated rejected specimen containers from the specimen re-putting section to the specimen measuring section after the information is deleted, wherein control system causes the specimen measuring section to measure the specimen in the operator-designated rejected specimen container transported to the specimen measuring section after the information relating to the rejected specimen container is deleted.

2. The specimen processing system according to claim 1, wherein the specimen measuring section comprises an aspirating section that aspirates blood accommodated in a capped specimen container as the specimen by penetrating into a cap of the capped specimen container with an aspirating tube and a detector configured to detect a blood cell included in blood aspirated by the aspirating section.

3. The specimen processing system according to claim 1, wherein the transporting system transports a specimen rack including a holding position for accommodating the specimen container, the imaging unit obtains an image of the specimen container that is accommodated in the specimen rack as the shape information, and the control system is configured to determine whether or not the specimen container imaged by the imaging unit is to be supplied to the specimen measuring section for analysis based on the image of the specimen container that is accommodated in the specimen rack.

4. The specimen processing system according to claim 1, wherein the transporting system comprises a transport section configured for transporting specimen containers to the specimen measuring section and a delivery section, and wherein the control system is configured to control the delivery section to deliver an accepted specimen container that is determined to be supplied to the specimen measuring section to the transport section, and to deliver a rejected specimen container that is determined not to be supplied to the specimen measuring section to the collect section or the specimen re-putting section.

5. The specimen processing system according to claim 4, wherein
the imaging unit includes a white light source and at least one camera, the white light source positioned relative to the at least one camera, such that reflected white light does not directly enter the at least one camera,
and
the delivery section is configured for alternatively delivering specimen containers to the transport section that are determined by the controller to be suitable for analysis, and delivering rejected specimen containers that are determined by the controller not to be suitable for analysis to the collect section or specimen-reputting section.

6. The specimen processing system according to claim 5, wherein the transport section is configured for transporting a specimen rack capable of accommodating a plurality of said specimen containers,
the collect section is configured for collecting the specimen rack, and the imaging unit is configured for obtaining the shape information on specimen containers accommodated in the specimen rack, and
wherein the display is coupled to the imaging unit, and the control system is configured to control the display to distinguishably display the shape information on the rejected specimen containers from other specimen containers accommodated in the same specimen rack.

7. The specimen processing system according to claim 6, further comprising:
an input device,
wherein the control system is configured to control the display to selectably display the specimen rack, and
when the selection of the specimen rack is accepted via the input device, the shape information on the rejected specimen container is distinguishably displayed from other specimen containers accommodated in the selected specimen rack.

8. The specimen processing system according to claim 7, wherein
the specimen setting section on which a specimen rack is set, wherein the specimen rack includes a specimen rack information section in which specifying information for the specimen rack is recorded, and the specimen processing system further comprises a reader configured for reading the specimen rack information from the specimen rack information section of the specimen rack set on the specimen setting section, and the control system is configured to control the display to display the specimen rack information, which is read by the reader, of the specimen rack collected by the collect section.

9. The specimen processing system according to claim 6 wherein the display comprises a touch sensitive display.

* * * * *